US012679901B2

(12) United States Patent
Oida et al.

(10) Patent No.: US 12,679,901 B2
(45) Date of Patent: Jul. 14, 2026

(54) ANTI-TLR7 AGENTS AND COMPOSITIONS AND METHODS FOR MAKING AND USING THE SAME

(71) Applicant: BIOLEGEND, INC., San Diego, CA (US)

(72) Inventors: Takatoku Oida, San Diego, CA (US); Anagha Ashok Divekar, San Diego, CA (US); Shawna Ann Shirley, San Diego, CA (US); Nicole Vivienne Acuff, San Diego, CA (US)

(73) Assignee: BioLegend, Inc., San Diego, CA (US)

( * ) Notice: Subject to any disclaimer, the term of this patent is extended or adjusted under 35 U.S.C. 154(b) by 989 days.

(21) Appl. No.: 17/861,196

(22) Filed: Jul. 9, 2022

(65) Prior Publication Data

US 2023/0054169 A1 Feb. 23, 2023

Related U.S. Application Data

(63) Continuation of application No. PCT/US2021/013378, filed on Jan. 14, 2021.

(60) Provisional application No. 62/962,457, filed on Jan. 17, 2020.

(51) Int. Cl.
| | |
|---|---|
| *C07K 16/28* | (2006.01) |
| *G01N 33/68* | (2006.01) |
| *A61K 39/395* | (2006.01) |

(52) U.S. Cl.
CPC ..... *C07K 16/2896* (2013.01); *G01N 33/6872* (2013.01); *C07K 2317/24* (2013.01); *C07K 2317/565* (2013.01); *C07K 2317/567* (2013.01); *C07K 2317/76* (2013.01)

(58) Field of Classification Search
CPC ............... C07K 16/28; C07K 2317/56; C07K 2317/565; C07K 2317/76; C07K 2317/24; A61K 2039/505; A61K 39/3955
See application file for complete search history.

(56) References Cited

U.S. PATENT DOCUMENTS

2018/0346601 A1 12/2018 Dettling et al.

FOREIGN PATENT DOCUMENTS

| | | |
|---|---|---|
| CN | 102197306 A | 9/2011 |
| CN | 102471382 A | 5/2012 |
| EP | 2990419 A1 | 3/2016 |
| WO | 0222809 A2 | 3/2002 |
| WO | 2014174704 A1 | 10/2014 |
| WO | 2019230869 A1 | 12/2019 |

OTHER PUBLICATIONS

Brorson et al. Mutational analysis of avidity and fine specificity of anti-levan antibodies. J Immunol 163: 6694-6701, 1999.*
Brummell et al. Probing the combining site of an anti-carbohydrate antibody by saturation-mutagenesis: role of the heavy-chain CDR3 residues. Biochem 32(4): 1180-1187, 1993 (abstract).*
Burks et al. In vitro scanning saturation mutagenesis of an antibody binding pocket. Proc Natl Acad Sci USA 94: 412-417, 1997.*
Cassett et al. A peptide mimetic of an anti-CD4 monoclonal antibody by rationale design. Biochem Biophys Res Comm 307: 198-205, 2003.*
Chen et al. J Mol Biol 293: 865-881, 1999.*
Colman Research in Immunol. 145:33-36, 1994.*
Herold et al. Determinants of the assembly and function of antibody variable domains. Sci Reports 7: 12276, 2017; DOI: 10.1038/s41598-017-12519-9.*
Holm et al. Functional mapping and single chain construction of the anti-cytokeratin 8 monoclonal antibody TS1. Mol Immunol 44: 1075-1084, 2007.*
Jang et al. The structural basis for DNA binding by an anti-DNA autobody. Mol Immunol 35: 1207-1217, 1998.*
Kobayashi et al. Tryptophan H33 plays an important role in pyrimidine (6-4) pyrimidone photoproduct binding by a high-affinity antibody. Protein Engineering 12(10): 879-884, 1999.*
Kranz et al. Restricted reassociation of heavy and light chains from hapten-specific monoclonal antibodies. Proc Natl Acad Sci USA 78(9): 5807-5811, 1981.*
MacCallum et al. Antibody-antigen interactions: contact analysis and binding site topography. J Mol Biol 262: 732-745, 1996.*
Nezlin, R.S. Biochemistry of Antibodies. New York: Plenum Press, 1970, p. 160.*
Paul, William E., Fundamental Immunology, 3rd Edition, Raven Press, New York, Chapt. 8, pp. 292-295 (1993).*
Rudikoff et al. Single amino acid substitution altering antigen-binding specificity. Proc Natl Acad Sci USA 79: 1979-1983, 1982.*
Vasudevan et al. A single amino acid change in the binding pocket alters specificity of an anti-integrin antibody AP7.4 as revealed by its crystal structure. Blood Cell Mol Dis 32: 176-181, 2004.*
Zhang et al. Comprehensive optimization of a single-chain variable domain antibody fragment as a targeting ligand for a cytotoxic nanoparticle. mAbs 7(1): 42-52, 2015.*
Application No. CN202180021763.2 , Office Action, Mailed on Apr. 25, 2024, 10 pages. English Translation on pp. 1-3.
Luo et al., "Research on TLR7 Gene in Different Animals", Progress in Veterinary Medicine, vol. 40, No. 11, Dec. 31, 2019, pp. 130-133. English Abstract on p. 1.
Kanno et al., Essential Role for Toll-Like receptor 7 (TLR7)-Unique Cysteines in an Intramolecular Disulfide Bond, Proteolytic Cleavage and RNA Sensing, International Immunology, vol. 25, No. 7, Feb. 26, 2013, pp. 413-422.

(Continued)

*Primary Examiner* — Bridget E Bunner
(74) *Attorney, Agent, or Firm* — Kilpatrick Townsend & Stockton LLP

(57) ABSTRACT

Compositions and methods for making and using anti-TLR7 agents, for example, monoclonal antibodies, TLR7-binding antibody fragments, and derivatives are described, as are kits, nucleic acids encoding such molecules, diagnostic reagents and kits that include anti-TLR7 agents, and methods of making and using the same.

19 Claims, 10 Drawing Sheets

Specification includes a Sequence Listing.

(56)         References Cited

OTHER PUBLICATIONS

Kanno et al., Targeting Cell Surface TLR7 for Therapeutic Intervention in Autoimmune Diseases, Nature Communications, vol. 6, Feb. 4, 2015, 12 pages.

Karlsen et al., Expression of Toll-Like Receptors in Peripheral Blood Mononuclear Cells of Patients with Primary Sjogren's Syndrome, Scandinavian Journal of Immunology, vol. 85, No. 3, Mar. 1, 2017, pp. 220-226.

International Application No. PCT/US2021/013378, International Preliminary Report on Patentability mailed on Mailed on Jul. 28, 2022, 11 pages.

International Application No. PCT/US2021/013378, International Search Report and Written Opinion mailed on May 10, 2021, 17 pages.

Petes et al., The Toll for Trafficking: Toll-Like Receptor 7 Delivery to the Endosom, Frontiers in Immunology, vol. 8, Sep. 4, 2017, 9 pages.

Suthers et al., TLR7/TLR9- and B Cell Receptor-Signaling Crosstalk: Promotion of Potentially Dangerous B Cells, Frontiers in Immunology, vol. 8, Jul. 13, 2017, 8 pages.

\* cited by examiner

Full-length Human TLR7 Amino Acid Sequence (SEQ ID NO:48)

```
   1 mvfpmwtlkr qililfniil iskllgarwf pktlpcdvtl dvpknhvivd ctdkhlteip
  61 ggiptnttnl tltinhipdi spasfhrldh lveidfrcnc vpiplgsknn mcikriqikp
 121 rsfsgltyik slyldgnqll eipqglppsl qlisleanni fsirkenlte lanieilylg
 181 qncyyrnpcy vsysiekdaf lnltkikvls lkdnnvtavp tvlpstitel ylynmiaki
 241 qeddfnning lqildlsgnc prcynapfpc apcknnsplq ipvnafdalt elkvlrlhsn
 301 slqhvpprwf kninklqeld lsqnflakei gdakflhflp sliqldlsfn felqvyrasm
 361 nlsqafsslk sikilrirgy vfkelksfnl spihnlqnle vldlgtnfik ianlsmfkqf
 421 krikvidlsv nkispsgdss evgfcsnart svesyepqvl eqlhyfrydk yarscrfknk
 481 easfmsvnes cykyggqtldi sknsiffvks sdfqhisflk clnlsgnlis qtlngsefqp
 541 laelryldfs nnrldilhst afeelhklev ldlssnshyf qsegithmln ftknlkvlqk
 601 lmmndndiss stsrtmeses lrtlefrgnh ldvlwregdn rylqlfknll kleeldiskn
 661 slsflpsgvf dgmppnlkni slaknglksf swkklqcikn letidlshnq lttvperlsn
 721 csrslkniil knnqirsltk yflqdafqir yldlssnkiq miqktsfpen vlnnlkmlll
 781 hhnrflctcd avwfvwwvnh tevtlpylat dvtcvgpgah kgqsvisidl ytceldltnl
 841 ilfslsisvs lflmvmmtas hlyfwdvwyi yhfckakikg yqrlispdcc ydafivydtk
 901 dpavtewvla elvakledpr ekhfniclee rdwlpgqpvl enlsqsiqls kktvfvmtdk
 961 yaktenfkia fylshqrlmd ekvdviilif lekpfqkskf lqlrkrlcgs svlewptnpq
1021 ahpyfwqclk nalatdnhva ysqvfketv
```

FIG. 1

Anti-TLR7 Antibody Heavy and Light Chain Variable Region and CDR
Amino Acid Sequence Alignments
Heavy Chain Variable Region: FRH1-CDRH1-FRH2-CDRH2-FRH3-CDRH3-FRH4
AB

```
1    ELQLVESGGGLVKPGASLKLSCVASGFTFSDYWMSWVRQTPGKTMEWIGDIKYDGSFIDY
2    ELQLVESGGGLVKPGASLKLSCVASGFTFSDYWMSWVRQTPGKTMEWIGDIKYDGSFIDY
3    ELQLVESGGGLLQPGRSLKLSCAASGFTFTNYYMAWVRQAPTKGLEWVASITNSGRTTYY
4    EVQLVESGGGLVQPGRSLKLSCAASGFTFRDYYMAWVRQAPKKGLEWVASISYEGSSTHY
5    QVNLLQSGAALVKPGASVKLSCKASGYTFTDYCVHWVKQSHGKSLEWIGYINPYSGYTNY
6    QVNLLQSGAALVKPGASVKLSCKASGYTFTDYYIHWVKQSHVKSLEWFGFINPDSGYTNY
     ::::*::**..*::** *:**** ***:** :* : **:*:   * :**.. *.  .      *

1    APSLKNRFTISRDNAKNTLYLQMSNVRSEDTATYYCARDLTT--VVDG----FAYWGQGT
2    APSLKNRFTISRDNAKNTLYLQMSNVRSEDTATYYCARDLTT--VVDG----FAYWGHGT
3    RDSVKGRFTISRDNAKSTLYLQMDSLRSEDTATYYCTREGGDLYYSNYNYVRFAYWGQGT
4    GDSVKARFTVSRDDAKSTLYLQMNSLRSEDTATYYCGRHGG---YPNW---YFDFWGPGT
5    NEKFKSKATLTVDTSTNTAYMELSRLTSDDSATCYCTRGPYGGYSGDG----FDYWGQGV
6    NEKFKTKATLTVDKSTNTAYMELSRLTSEGSATYYCTRGPYGGYSGDG----FDYWGQGV
     ..* : *:: * :..* *:::. : *:.:** ** *        :      * :** *.

1    LVTVSS  (SEQ ID NO:36)
2    LVTVSS  (SEQ ID NO:37)
3    LVTVSS  (SEQ ID NO:38)
4    MVTVSS  (SEQ ID NO:39)
5    MVTVSS  (SEQ ID NO:40)
6    MVTVSS  (SEQ ID NO:41)
     :*****
```

Light Chain Variable Region: FRL1-CDRL1-FRL2-CDRL2-FRL3-CDRL3-FRL4

AB

```
5    DIQMTQSPASLSASLGETVTIECRASEDIYNVLAWYQQKPGKSPQLLISNANRLHNGVPS
6    DIQMTQSPASLSASLGETVTIECRASEDIYNVLAWYQQKPGKSPQLLISNANNLHTGVPS
3    DIQMTQSPASLSASLGETVSIECLPSEDIYNNLAWYQQKPGKSPQLLIHYASNLQDGVPS
4    DIQMTQSPASLSASLGETVTIECRASEDIYNELAWYQQKPGKSPQLLIYNANSLHTGVPS
2    NIVLTQSPATLSVTPGESVSLSCRASQSLSTSIHWYQQKPNESPRLLIRYASQPISGIPS
1    NIVLTQSPATLSVTPGESVSLSCRASQSLSTSIHWYQQMPNESPRLLIRYASQPISGIPS
     :* :*****:**.: **:*::.* .*:.: . : **** *.:**:*** *.    *:**

5    RFSGSGSGTQYLSKINSLQSEDVASYFCQQYYDYPNTFGAGTKLELK (SEQ ID NO:46)
6    RFSGSGSGTQYSLKINSLQSEDVASYFCQQYYDYPHTFGAGTKLELK (SEQ ID NO:47)
3    RFSGSGSGTQYSLKIKSLESEDAATYFCLQDSDYPFTFGSGTKLEIK (SEQ ID NO:44)
4    RFSGSGSGTQYSLKINSLQSEDVASYFCQQYYDYPWTFGGGTKLELK (SEQ ID NO:45)
2    RFSFSFSFTDFTLSINRVESEDFSIYYCQQSYSSPYTFGAGTRLELK (SEQ ID NO:43)
1    RFSGSGSGTDFTLSINRVESEDFSIYYCQQSYSSPYTFGAGTKLELK (SEQ ID NO:42)
     *****.***::*.*: ::*** : *:* * . * ***.**:**:*
```

FIG. 2

Clone Information

| ID | Source | Clone | Isotype | Format | Yield |
|---|---|---|---|---|---|
| AB1 | BioLegend | 1 | Rat IgG1, k | PE | 43.48 |
| AB2 | BioLegend | 2 | Rat IgG1, k | PE | 43.1 |
| AB3 | BioLegend | 3 | Rat IgG1, k | PE | 42.58 |
| AB4 | BioLegend | 4 | Rat IgG1, k | PE | 6.45 |
| AB5 | BioLegend | 5 | Rat IgG1, k | PE | 46.52 |
| AB6 | BioLegend | 6 | Rat IgG2a, k | PE | 39.72 |
| Commercial ABl | Commercially available | N/A | Mouse IgG1, κ | APC | |

*FIG. 3*

Gating Strategy

Surface Staining

Intracellular Staining

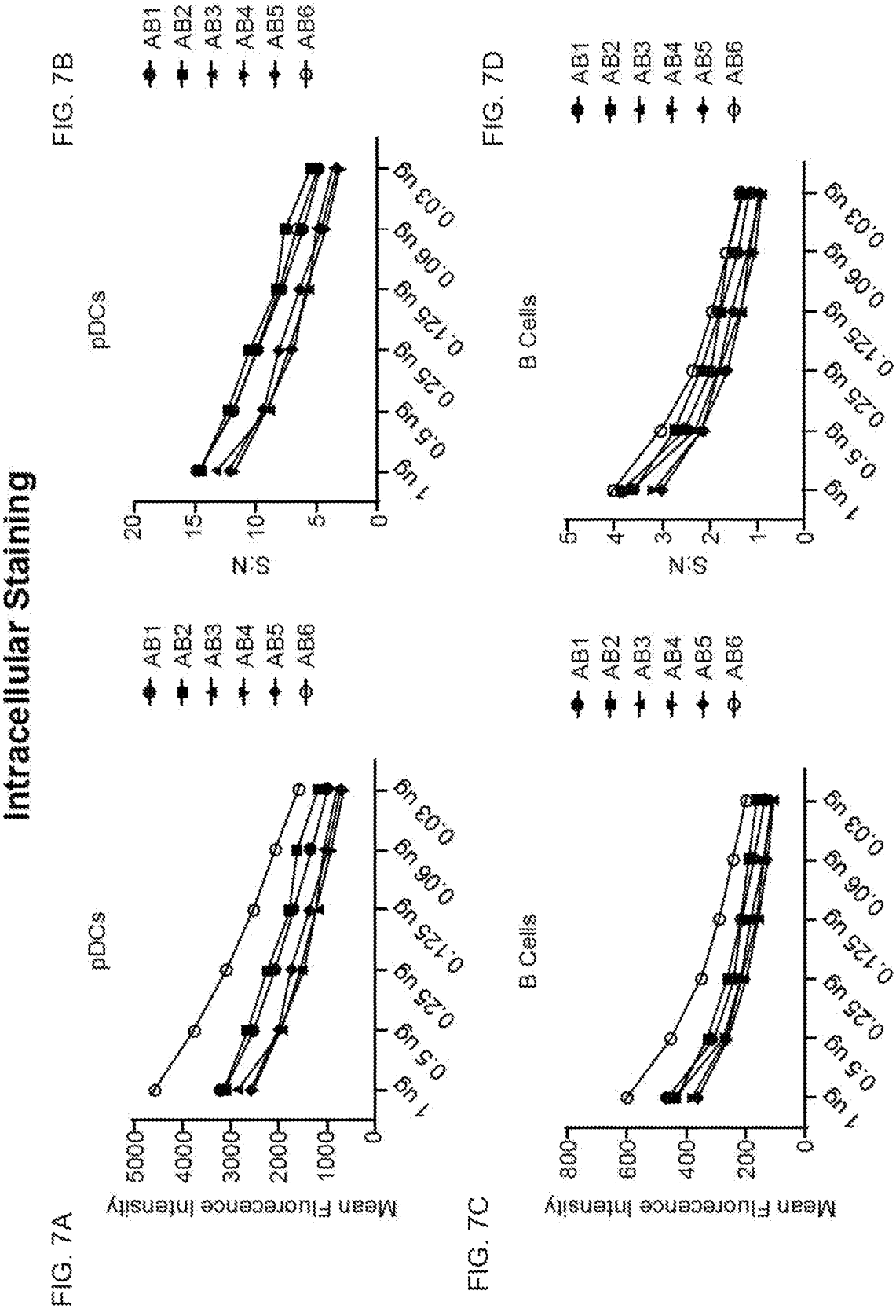

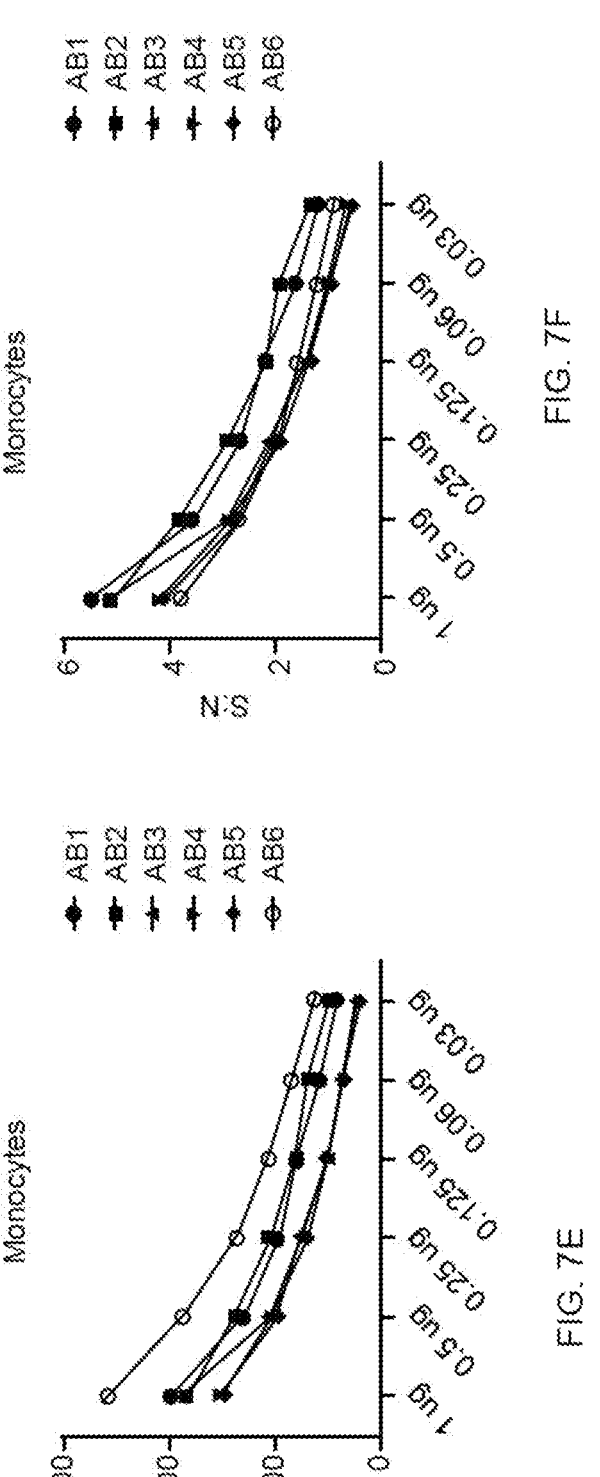

SEQUENCE LISTING

```
Sequence total quantity: 55
SEQ ID NO: 1            moltype = AA  length = 5
FEATURE                 Location/Qualifiers
REGION                  1..5
```

-continued

```
                          note = Description of Artificial Sequence: Synthetic peptide
source                    1..5
                          mol_type = protein
                          organism = synthetic construct
SEQUENCE: 1
DYWMS                                                                         5

SEQ ID NO: 2              moltype = AA   length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 2
NYYMA                                                                         5

SEQ ID NO: 3              moltype = AA   length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 3
DYYMA                                                                         5

SEQ ID NO: 4              moltype = AA   length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 4
DYCVH                                                                         5

SEQ ID NO: 5              moltype = AA   length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 5
DYYIH                                                                         5

SEQ ID NO: 6              moltype = AA   length = 17
FEATURE                   Location/Qualifiers
REGION                    1..17
                          note = Description of Artificial Sequence: Synthetic peptide
source                    1..17
                          mol_type = protein
                          organism = synthetic construct
SEQUENCE: 6
DIKYDGSFID YAPSLKN                                                           17

SEQ ID NO: 7              moltype = AA   length = 17
FEATURE                   Location/Qualifiers
REGION                    1..17
                          note = Description of Artificial Sequence: Synthetic peptide
source                    1..17
                          mol_type = protein
                          organism = synthetic construct
SEQUENCE: 7
DIKYDGTFID YAPSLKN                                                           17

SEQ ID NO: 8              moltype = AA   length = 17
FEATURE                   Location/Qualifiers
REGION                    1..17
                          note = Description of Artificial Sequence: Synthetic peptide
source                    1..17
                          mol_type = protein
                          organism = synthetic construct
SEQUENCE: 8
SITNSGRTTY YRDSVKG                                                           17

SEQ ID NO: 9              moltype = AA   length = 17
FEATURE                   Location/Qualifiers
```

```
REGION                   1..17
                         note = Description of Artificial Sequence: Synthetic peptide
source                   1..17
                         mol_type = protein
                         organism = synthetic construct
SEQUENCE: 9
SISYEGSSTH YGDSVKA                                                      17

SEQ ID NO: 10            moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 10
YINPYSGYTN YNEKFKS                                                      17

SEQ ID NO: 11            moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 11
FINPDSGYTN YNEKFKT                                                      17

SEQ ID NO: 12            moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 12
DLTTVVDGFA Y                                                            11

SEQ ID NO: 13            moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 13
EGGDLYYSNY NYVRFAY                                                      17

SEQ ID NO: 14            moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 14
HGGYPNWYFD F                                                            11

SEQ ID NO: 15            moltype = AA  length = 13
FEATURE                  Location/Qualifiers
REGION                   1..13
                         note = Description of Artificial Sequence: Synthetic peptide
source                   1..13
                         mol_type = protein
                         organism = synthetic construct
SEQUENCE: 15
GPYGGYSGDG FDY                                                          13

SEQ ID NO: 16            moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 16
RASEDIYNVL A                                                            11

SEQ ID NO: 17            moltype = AA  length = 11
```

```
FEATURE               Location/Qualifiers
REGION                1..11
                      note = Description of Artificial Sequence: Synthetic peptide
source                1..11
                      mol_type = protein
                      organism = synthetic construct
SEQUENCE: 17
RASEDIYNEL A                                                              11

SEQ ID NO: 18         moltype = AA  length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 18
LPSEDIYNNL A                                                              11

SEQ ID NO: 19         moltype = AA  length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 19
RASQSLSTSI H                                                             11

SEQ ID NO: 20         moltype = AA  length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 20
NANRLHN                                                                   7

SEQ ID NO: 21         moltype = AA  length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 21
NANNLHT                                                                   7

SEQ ID NO: 22         moltype = AA  length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 22
NANSLHT                                                                   7

SEQ ID NO: 23         moltype = AA  length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 23
YASNLQD                                                                   7

SEQ ID NO: 24         moltype = AA  length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 24
YASQPIS                                                                   7
```

```
SEQ ID NO: 25          moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct SEQUENCE: 25
QQYYDYPNT                                                          9

SEQ ID NO: 26          moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct SEQUENCE: 26
QQYYDYPHT                                                          9

SEQ ID NO: 27          moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct SEQUENCE: 27
QQYYDYPWT                                                          9

SEQ ID NO: 28          moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct SEQUENCE: 28
LQDSDYPFT                                                          9

SEQ ID NO: 29          moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct SEQUENCE: 29
QQSYSSPYT                                                          9

SEQ ID NO: 30          moltype = AA   length = 5
FEATURE                Location/Qualifiers
REGION                 1..5
                       note = Description of Artificial Sequence: Synthetic peptide
VARIANT                1
                       note = replace=N
VARIANT                3
                       note = replace=Y or C
VARIANT                4
                       note = replace=V or I
VARIANT                5
                       note = replace=A or H
SITE                   1..5
                       note = Note: Variant residues given in the sequence have no
                        preference with respect to those in the annotations for
                        variant positions
source                 1..5
                       mol_type = protein
                       organism = synthetic construct SEQUENCE: 30
DYWMS                                                              5

SEQ ID NO: 31          moltype = AA   length = 17
FEATURE                Location/Qualifiers
REGION                 1..17
                       note = Description of Artificial Sequence: Synthetic peptide
VARIANT                1
                       note = replace=S or Y or F
VARIANT                3
```

```
                         note = replace=T or S or N
VARIANT                  4
                         note = replace=N or P
VARIANT                  5
                         note = replace=S or E or Y
VARIANT                  6
                         note = replace=S
VARIANT                  7
                         note = replace=T or R or G
VARIANT                  8
                         note = replace=T or S or Y
VARIANT                  9
                         note = replace=T
VARIANT                  10
                         note = Replace with Y or H or N
VARIANT                  12
                         note = Replace with R or G or N
VARIANT                  13
                         note = Replace with D or E
VARIANT                  14
                         note = Replace with K
VARIANT                  15
                         note = Replace with V or F
VARIANT                  17
                         note = Replace with G or A or S or T
SITE                     1..17
                         note = Note: Variant residues given in the sequence have no
                          preference with respect to those in the annotations for
                          variant positions
source                   1..17
                         mol_type = protein
                         organism = synthetic construct
SEQUENCE: 31
DIKYDGSFID YAPSLKN                                                        17

SEQ ID NO: 32            moltype = AA  length = 17
FEATURE                  Location/Qualifiers
REGION                   1..17
                         note = Description of Artificial Sequence: Synthetic peptide
VARIANT                  1
                         note = Replace with E or H or G
VARIANT                  2
                         note = Replace with G or P
VARIANT                  3
                         note = Replace with G or Y
VARIANT                  4
                         note = Replace withor D or G
VARIANT                  5
                         note = Replace withor G
VARIANT                  6
                         note = Replace with
VARIANT                  7
                         note = Replace with Y or S
VARIANT                  8
                         note = Replace with S or P or G
VARIANT                  9
                         note = Replace with N
VARIANT                  10
                         note = Replace with Y or W
VARIANT                  11
                         note = Replace with
VARIANT                  12
                         note = Replace with
VARIANT                  13
                         note = Replace with
VARIANT                  14
                         note = Replace withor Y
VARIANT                  16
                         note = Replace with D
VARIANT                  17
                         note = Replace with F
SITE                     1..17
                         note = Note: Variant residues given in the sequence have no
                          preference with respect to those in the annotations for
                          variant positions
source                   1..17
                         mol_type = protein
                         organism = synthetic construct
SEQUENCE: 32
```

```
DLTTLYVVDG NYVRFAY                                                      17

SEQ ID NO: 33         moltype = AA   length = 11
FEATURE               Location/Qualifiers
REGION                1..11
                      note = Description of Artificial Sequence: Synthetic peptide
VARIANT               1
                      note = Replace with L
VARIANT               2
                      note = Replace with P
VARIANT               4
                      note = Replace with Q
VARIANT               5
                      note = Replace with S
VARIANT               6
                      note = Replace with L
VARIANT               7
                      note = Replace with S
VARIANT               8
                      note = Replace with T
VARIANT               9
                      note = Replace with E or N or S
VARIANT               10
                      note = Replace with I
VARIANT               11
                      note = Replace with H
SITE                  1..11
                      note = Note: Variant residues given in the sequence have no
                       preference with respect to those in the annotations for
                       variant positions
source                1..11
                      mol_type = protein
                      organism = synthetic construct
SEQUENCE: 33
RASEDIYNVL A                                                            11

SEQ ID NO: 34         moltype = AA   length = 7
FEATURE               Location/Qualifiers
REGION                1..7
                      note = Description of Artificial Sequence: Synthetic peptide
VARIANT               1
                      note = Replace with Y
VARIANT               3
                      note = Replace with S
VARIANT               4
                      note = Replace with N or S or Q
VARIANT               5
                      note = Replace with P
VARIANT               6
                      note = Replace with Q or I
VARIANT               7
                      note = Replace with T or D or S
SITE                  1..7
                      note = Note: Variant residues given in the sequence have
                       nopreference with respect to those in the annotationsfor
                       variant positions
source                1..7
                      mol_type = protein
                      organism = synthetic construct
SEQUENCE: 34
NANRLHN                                                                 7

SEQ ID NO: 35         moltype = AA   length = 9
FEATURE               Location/Qualifiers
REGION                1..9
                      note = Description of Artificial Sequence: Synthetic peptide
VARIANT               1
                      note = Replace with L
VARIANT               3
                      note = Replace with D or S
VARIANT               4
                      note = Replace with S
VARIANT               5
                      note = Replace with S
VARIANT               6
                      note = Replace with S
VARIANT               8
                      note = Replace with H or W or F or Y
SITE                  1..9
```

```
                        note = Note: Variant residues given in the sequence have no
                         preference with respect to those in the annotations for
                         variant positions
source                  1..9
                        mol_type = protein
                        organism = synthetic construct
SEQUENCE: 35
QQYYDYPNT                                                              9

SEQ ID NO: 36           moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 36
ELQLVESGGG LVKPGASLKL SCVASGFTFS DYWMSWVRQT PGKTMEWIGD IKYDGSFIDY  60
APSLKNRFTI SRDNAKNTLY LQMSNVRSED TATYYCARDL TTVVDGFAYW GQGTLVTVSS  120

SEQ ID NO: 37           moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 37
ELQLVESGGG LVKPGASLKL SCVASGFTFS DYWMSWVRQT PGKTMEWIGD IKYDGTFIDY  60
APSLKNRFTI SRDNAKNTLY LQMSNVRSED TATYYCARDL TTVVDGFAYW GHGTLVTVSS  120

SEQ ID NO: 38           moltype = AA  length = 126
FEATURE                 Location/Qualifiers
REGION                  1..126
                        note = Description of Artificial Sequence: Synthetic
                         polypeptide
source                  1..126
                        mol_type = protein
                        organism = synthetic construct
SEQUENCE: 38
EVQLVESGGG LLQPGRSLKL SCAASGFTFT NYYMAWVRQA PTKGLEWVAS ITNSGRTTYY  60
RDSVKGRFTI SRDNAKSTLY LQMDSLRSED TATYYCTREG GDLYYSNYNY VRFAYWGQGT  120
LVTVSS                                                                126

SEQ ID NO: 39           moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 39
EVQLVESGGG LVQPGRSLKL SCAASGFTFR DYYMAWVRQA PKKGLEWVAS ISYEGSSTHY  60
GDSVKARFTV SRDDAKSTLY LQMNSLRSED TATYYCGRHG GYPNWYFDFW GPGTMVTVSS  120

SEQ ID NO: 40           moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 40
QVNLLQSGAA LVKPGASVKL SCKASGYTFT DYCVHWVKQS HGKSLEWIGY INPYSGYTNY  60
NEKFKSKATL TVDTSTNTAY MELSRLTSDD SATCYCTRGP YGGYSGDGFD YWGQGVMVTV  120
SS                                                                    122

SEQ ID NO: 41           moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
```

```
SEQUENCE: 41
QVNLLQSGAA LVKPGASVKL SCKASGYTFT DYYIHWVKQS HVKSLEWFGF INPDSGYTNY   60
NEKFKTKATL TVDKSTNTAY MELSRLTSEG SATYYCTRGP YGGYSGDGFD YWGQGVMVTV  120
SS                                                                 122

SEQ ID NO: 42              moltype = AA   length = 107
FEATURE                    Location/Qualifiers
REGION                     1..107
                           note = Description of Artificial Sequence: Synthetic
                            polypeptide
source                     1..107
                           mol_type = protein
                           organism = synthetic construct
SEQUENCE: 42
NIVLTQSPAT LSVTPGESVS LSCRASQSLS TSIHWYQQKP NESPRLLIRY ASQPISGIPS   60
RFSGSGSGTD FTLSINRVES EDFSIYYCQQ SYSSPYTFGA GTKLELK               107

SEQ ID NO: 43              moltype = AA   length = 107
FEATURE                    Location/Qualifiers
REGION                     1..107
                           note = Description of Artificial Sequence: Synthetic
                            polypeptide
source                     1..107
                           mol_type = protein
                           organism = synthetic construct
SEQUENCE: 43
NIVLTQSPAT LSVTPGESVS LSCRASQSLS TSIHWYQQMP NESPRLLIRY ASQPISGIPS   60
RFSGSGSGTD FTLSINRVES EDFSIYYCQQ SYSSPYTFGA GTRLELK               107

SEQ ID NO: 44              moltype = AA   length = 107
FEATURE                    Location/Qualifiers
REGION                     1..107
                           note = Description of Artificial Sequence: Synthetic
                            polypeptide
source                     1..107
                           mol_type = protein
                           organism = synthetic construct
SEQUENCE: 44
DIQMTQSPAS LSASLGETVS IECLPSEDIY NNLAWYQQKP GKSPQLLIHY ASNLQDGVPS   60
RFSGSGSGTQ YSLKIKSLES EDAATYFCLQ DSDYPFTFGS GTKLEIK               107

SEQ ID NO: 45              moltype = AA   length = 107
FEATURE                    Location/Qualifiers
REGION                     1..107
                           note = Description of Artificial Sequence: Synthetic
                            polypeptide
source                     1..107
                           mol_type = protein
                           organism = synthetic construct
SEQUENCE: 45
DIQMTQSPAS LSASLGETVT IECRASEDIY NELAWYQQKP GKSPQLLIYN ANSLHTGVPS   60
RFSGSGSGTQ YSLKINSLQS EDVASYFCQQ YYDYPWTFGG GTKLELK               107

SEQ ID NO: 46              moltype = AA   length = 107
FEATURE                    Location/Qualifiers
REGION                     1..107
                           note = Description of Artificial Sequence: Synthetic
                            polypeptide
source                     1..107
                           mol_type = protein
                           organism = synthetic construct
SEQUENCE: 46
DIQMTQSPAS LSASLGETVT IECRASEDIY NVLAWYQQKP GKSPQLLISN ANRLHNGVPS   60
RFSGSGSGTQ YSLKINSLQS EDVASYFCQQ YYDYPNTFGA GTKLELK               107

SEQ ID NO: 47              moltype = AA   length = 107
FEATURE                    Location/Qualifiers
REGION                     1..107
                           note = Description of Artificial Sequence: Synthetic
                            polypeptide
source                     1..107
                           mol_type = protein
                           organism = synthetic construct
SEQUENCE: 47
DIQMTQSPAS LSASLGETVT IECRASEDIY NVLAWYQQKP GKSPQLLISN ANNLHTGVPS   60
RFSGSESGTQ YSLKINSLQS EDVASYFCQQ YYDYPHTFGA GTKLELK               107

SEQ ID NO: 48              moltype = AA   length = 1049
FEATURE                    Location/Qualifiers
```

```
source                 1..1049
                       mol_type = protein
                       organism = Homo sapiens
SEQUENCE: 48
MVFPMWTLKR QILILFNIIL ISKLLGARWF PKTLPCDVTL DVPKNHVIVD CTDKHLTEIP   60
GGIPTNTTNL TLTINHIPDI SPASFHRLDH LVEIDFRCNC VPIPLGSKNN MCIKRLQIKP   120
RSFSGLTYLK SLYLDGNQLL EIPQGLPPSL QLLSLEANNI FSIRKENLTE LANIEILYLG   180
QNCYYRNPCY VSYSIEKDAF LNLTKLKVLS LKDNNVTAVP TVLPSTLTEL YLYNNMIAKI   240
QEDDFNNLNQ LQILDLSGNC PRCYNAPFPC APCKNNSPLQ IPVNAFDALT ELKVLRLHSN   300
SLQHVPPRWF KNINKLQELD LSQNFLAKEI GDAKFLHFLP SLIQLDLSFN FELQVYRASM   360
NLSQAFSSLK SLKILRIRGY VFKELKSFNL SPLHNLQNLE VLDLGTNFIK IANLSMFKQF   420
KRLKVIDLSV NKISPSGDSS EVGFCSNART SVESYEPQVL EQLHYFRYDK YARSCRFKNK   480
EASFMSVNES CYKYGQTLDL SKNSIFFVKS SDFQHLSFLK CLNLSGNLIS QTLNGSEFQP   540
LAELRYLDFS NNRLDLLHST AFEELHKLEV LDISSNSHYF QSEGITHMLN FTKNLKVLQK   600
LMMNDNDISS STSRTMESES LRTLEFRGNH LDVLWREGDN RYLQLFKNLL KLEELDISKN   660
SLSFLPSGVF DGMPPNLKNL SLAKNGLKSF SWKKLQCLKN LETLDLSHNQ LTTVPERLSN   720
CSRSLKNLIL KNNQIRSLTK YFLQDAFQLR YLDLSSNKIQ MIQKTSFPEN VLNNLKMLLL   780
HHNRFLCTCD AVWFVWWVNH TEVTIPYLAT DVTCVGPGAH KGQSVISLDL YTCELDLTNL   840
ILFSLSISVS LFLMVMMTAS HLYFWDVWYI YHFCKAKIKG YQRLISPDCC YDAFIVYDTK   900
DPAVTEWVLA ELVAKLEDPR EKHFNLCLEE RDWLPGQPVL ENLSQSIQLS KKTVFVMTDK   960
YAKTENFKIA FYLSHQRLMD EKVDVIILIF LEKPFQKSKF LQLRKRLCGS SVLEWPTNPQ   1020
AHPYFWQCLK NALATDNHVA YSQVFKETV                                    1049

SEQ ID NO: 49          moltype = AA  length = 26
FEATURE                Location/Qualifiers
source                 1..26
                       mol_type = protein
                       organism = Homo sapiens
SEQUENCE: 49
MVFPMWTLKR QILILFNIIL ISKLLG                                       26

SEQ ID NO: 50          moltype = AA  length = 1023
FEATURE                Location/Qualifiers
source                 1..1023
                       mol_type = protein
                       organism = Homo sapiens
SEQUENCE: 50
ARWFPKTLPC DVTLDVPKNH VIVDCTDKHL TEIPGGIPTN TTNLTLTINH IPDISPASFH   60
RLDHLVEIDF RCNCVPIPLG SKNNMCIKRL QIKPRSFSGL TYLKSLYLDG NQLLEIPQGL   120
PPSLQLLSLE ANNIFSIRKE NLTELANIEI LYLGQNCYYR NPCYVSYSIE KDAFLNLTKL   180
KVLSLKDNNV TAVPTVLPST LTELYLYNNM IAKIQEDDFN NLNQLQILDL SGNCPRCYNA   240
PFPCAPCKNN SPLQIPVNAF DALTELKVLR LHSNSLQHVP PRWFKNINKL QELDLSQNFL   300
AKEIGDAKFL HFLPSLIQLD LSFNFELQVY RASMNLSQAF SSLKSLKILR IRGYVFKELK   360
SFNLSPLHNL QNLEVLDLGT NFIKIANLSM FKQFKRLKVI DLSVNKISPS GDSSEVGFCS   420
NARTSVESYE PQVLEQLHYF RYDKYARSCR FKNKEASFMS VNESCYKYGQ TLDLSKNSIF   480
FVKSSDFQHL SFLKCLNLSG NLISQTLNGS EFQPLAELRY LDFSNNRLDL LHSTAFEELH   540
KLEVLDISSN SHYFQSEGIT HMLNFTKNLK VLQKLMMNDN DISSSTSRTM ESESLRTLEF   600
RGNHLDVLWR EGDNRYLQLF KNLLKLEELD ISKNSLSFLP SGVFDGMPPN LKNLSLAKNG   660
LKSFSWKKLQ CLKNLETLDL SHNQLTTVPE RLSNCSRSLK NLILKNNQIR SLTKYFLQDA   720
FQLRYLDLSS NKIQMIQKTS FPENVLNNLK MLLLHHNRFL CTCDAVWFVW WVNHTEVTIP   780
YLATDVTCVG PGAHKGQSVI SLDLYTCELD LTNLILFSLS ISVSLFLMVM MTASHLYFWD   840
VWYIYHFCKA KIKGYQRLIS PDCCYDAFIV YDTKDPAVTE WVLAELVAKL EDPREKHFNL   900
CLEERDWLPG QPVLENLSQS IQLSKKTVFV MTDKYAKTEN FKIAFYLSHQ RLMDEKVDVI   960
ILIFLEKPFQ KSKFLQLRKR LCGSSVLEWP TNPQAHPYFW QCLKNALATD NHVAYSQVFK   1020
ETV                                                                1023

SEQ ID NO: 51          moltype = AA  length = 217
FEATURE                Location/Qualifiers
REGION                 1..217
                       note = Description of Artificial Sequence: Synthetic
                       polypeptide
source                 1..217
                       mol_type = protein
                       organism = synthetic construct
SEQUENCE: 51
APELLGGPSV FLFPPKPKDT LMISRTPEVT CVVVDVSHED PEVKFNWYVD GVEVHNAKTK   60
PREEQYNSTY RVVSVLTVLH QDWLNGKEYK CKVSNKALPA PIEKTISKAK GQPREPQVYT   120
LPPSREEMTK NQVSLTCLVK GFYPSDIAVE WESNGQPENN YKTTPPVLDS DGSFFLYSKL   180
TVDKSRWQQG NVFSCSVMHE ALHNHYTQKS LSLSPGK                           217

SEQ ID NO: 52          moltype = AA  length = 214
FEATURE                Location/Qualifiers
REGION                 1..214
                       note = Description of Artificial Sequence: Synthetic
                       polypeptide
source                 1..214
                       mol_type = protein
                       organism = synthetic construct
SEQUENCE: 52
```

-continued

```
DIQMTQSPAS LSASLGETVT IECRASEDIY NVLAWYQQKP GKSPQLLISN ANRLHNGVPS   60
RFSGSGSGTQ YSLKINSLQS EDVASYFCQQ YYDYPNTFGA GTKLELKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 53          moltype = AA  length = 452
FEATURE                Location/Qualifiers
REGION                 1..452
                       note = Description of Artificial Sequence: Synthetic
                        polypeptide
source                 1..452
                       mol_type = protein
                       organism = synthetic construct
SEQUENCE: 53
QVNLLQSGAA LVKPGASVKL SCKASGYTFT DYYIHWVKQS HVKSLEWFGF INPDSGYTNY   60
NEKFKTKATL TVDKSTNTAY MELSRLTSEG SATYYCTRGP YGGYSGDGFD YWGQGVMVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                               452

SEQ ID NO: 54          moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 54
DIQMTQSPAS LSASLGETVT IECRASEDIY NVLAWYQQKP GKSPQLLISN ANNLHTGVPS   60
RFSGSESGTQ YSLKINSLQS EDVASYFCQQ YYDYPHTFGA GTKLELKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 55          moltype = AA  length = 452
FEATURE                Location/Qualifiers
REGION                 1..452
                       note = Description of Artificial Sequence: Synthetic
                        polypeptide
source                 1..452
                       mol_type = protein
                       organism = synthetic construct
SEQUENCE: 55
QVNLLQSGAA LVKPGASVKL SCKASGYTFT DYCVHWVKQS HGKSLEWIGY INPYSGYTNY   60
NEKFKSKATL TVDTSTNTAY MELSRLTSDD SATCYCTRGP YGGYSGDGFD YWGQGVMVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                               452
```

ANTI-TLR7 AGENTS AND COMPOSITIONS AND METHODS FOR MAKING AND USING THE SAME

CROSS-REFERENCE TO RELATED APPLICATIONS

The present application is a continuation of PCT/US2021/013378, filed Jan. 14, 2021, which claims priority to U.S. Provisional Patent Application No. 62/962,457, filed on Jan. 17, 2020, the disclosures of each of which are incorporated herein by reference in their entireties for all purposes.

REFERENCE TO SEQUENCE LISTING

A Sequence Listing conforming to the rules of WIPO Standard ST.26 is hereby incorporated by reference. The Sequence Listing has been filed as an electronic document via EFS-Web in ASCII format. The electronic document, created on Aug. 29, 2022, is entitled "102738-000910US-1339202_ST26.xml", and is 98,914 bytes in size.

FIELD

The technology relates in part to agents that bind Toll-like Receptor 7, i.e., TLR7, and its variants, particularly to monoclonal antibodies, antibody fragments, and antibody derivatives specifically reactive to TLR7 under physiological and/or in vitro conditions. Such agents can be useful for laboratory/research purposes (e.g., flow cytometry), and may be used in the treatment and/or prevention of various diseases or disorders through the delivery of pharmaceutical or other compositions that contain such agents.

BACKGROUND

The following description includes information that may be useful in understanding the present technology. It is not an admission that any of the information provided herein, or any publication specifically or implicitly referenced herein, is prior art, or even particularly relevant, to the presently claimed technology.

Toll-like receptors (TLRs) are present as membrane spanning proteins on many cells, and inside certain cells, of the immune system, and are generally involved in the innate immune response by recognizing pathogen-associated molecular patterns derived from various bacteria, fungi, parasites, and viruses. The innate immune system promptly responds to the invasion of microbes and acts as the first line of defense, whereby innate immune cells such as macrophages or dendritic cells (DCs) play a central role in the production of proinflammatory cytokines or nitric oxide. TLRs also are involved in the efficient establishment of acquired immunity against pathogens by directly detecting molecules from microbes. The adaptive immune system exerts highly specific responses to microbes by producing antibodies from B cells or through the generation of killer or helper T lymphocytes, resulting in life-long immunological memory. This process may take weeks, or even months, to establish sufficient levels of immunity. Some TLR types are located on the cell surface (e.g., to detect and initiate a response to extracellular pathogens), while other TLR types are located inside the cell (e.g., to detect and initiate a response to intracellular pathogens).

Pattern recognition receptors (PRRs), which recognize pathogen-associated molecular patterns (PAMPs) specific to each pathogen, generally are expressed on innate immune cells and discriminate self or non-self structures. More than 10 members of the TLR family are present in mammals and function as PRRs, recognizing a variety of PAMPs, such as lipopolysaccharide, lipoprotein, nucleic acids, and the like. In humans, 10 different TLR types have been identified, designated TLR1-10, while in mice, 13 TLR types have been identified. TLR1-TLR10 are conserved between humans and mice, although TLR10 is not functional in mice because of a retroviral insertion. TLR11-TLR13 are not present in humans.

TLRs are type I transmembrane proteins that consist of three major domains: (1) a leucine rich binding domain; (2) a transmembrane domain; and (3) a cytoplasmic TIR (i.e., Toll-IL-1R) domain. The TIR domain is a highly conserved intracellular domain found in IL-1R and various TLRs. For certain TLRs (e.g., TLR1, TLR2, TLR4, TLR5, TLR6, TLR10), ligand recognition by TLRs is mediated by the binding domain that harbors a leucine rich repeat (LRR) composed of 19-25 tandem copies of the "xLxxLxLxx" motif.

TLRs can be divided into extracellular and intracellular varieties. TLR1, TLR2, TLR4, TLR5, TLR6, and TLR11 recognize their ligands on the cell surface. In contrast, TLR3, TLR7, TLR8, and TLR9 are intracellularly localized on the endoplasmic reticulum (ER) membrane in resting cells.

Ligand binding typically causes dimerization of the cytoplasmic TIR domains, culminating in activation of downstream intracellular signaling mediated by TLR domain-containing adaptor proteins. Similar to mammalian IL-1R signaling, TLR signaling also activates NF-κB as well as mitogen-activated protein kinases (MAPKs) to stimulate gene expression, including pro-inflammatory cytokines and co-stimulatory molecules.

Genomic nucleic acids from bacteria and viruses, or their analogs, stimulate the production of proinflammatory cytokines and type I IFN. Among them, immunostimulatory bacterial DNA was first identified in Calmette-Guerin bacilli, which are capable of promoting antitumor activity and inducing type I IFN (IFN-α/β) and type II IFN (IFN-γ) in human peripheral blood leukocytes.

TLR7 is an intracellular receptor expressed on endosomal membranes. TLR7 is closely related to TLR8, which also recognizes nucleosides and nucleotides from intracellular pathogens. There are two ligand-binding sites in TLR7. The first site for binding of small ligands is conserved in both TLR7 and TLR8. The second site differs from that of TLR8, and is used to bind with single-stranded RNA (ssRNA) to enhance activation of the first site. Activation of TLR7 can induce Type 1 interferon and inflammatory response.

Described herein are particular monoclonal antibodies to TLR7 that provide superior target specificity, signal-to-noise ratios, and the like as compared to other reported anti-TLR antibodies, as well as antigen-binding fragments of such antibodies that also bind TLR7.

SUMMARY

Provided herein, in some aspects, are anti-TLR7 agents that bind Toll-like Receptor 7 (TLR7), including anti-TLR7 antibodies, TLR7-binding antibody fragments, derivatives, and variants of such antibodies and antibody fragments (including immunoconjugates, labeled antibodies and antigen-binding antibody fragments, and the like), diagnostic reagents that comprise such agents, containers and kits that include an anti-TLR7 agent provided herein, and methods of making and using the same.

Provided herein, in certain aspects, is an anti-TLR7 agent that binds TLR7 under laboratory or physiological conditions, where the agent comprises at least one immunoglobulin heavy chain variable domain and at least one immunoglobulin light chain variable domain, where a) each immunoglobulin heavy chain variable domain of the anti-TLR7 agent comprises first, second, and third heavy chain complementarity determining regions (CDRs), where the first heavy chain CDR (CDRH1) comprises an amino acid sequence that is at least 80 percent identical (e.g., 85, 87, 90, 91, 92, 93, 94, 95, 96, 97, 98, 99, or 100 percent identical) to the amino acid sequence $X_1YX_2X_3X_4$ (SEQ ID NO:30), where $X_1$ is D or N, $X_2$ is W, Y, or C, $X_3$ is M, V, or I, and $X_4$ is S, A, or H; the second heavy chain CDR (CDRH2) comprises an amino acid sequence that is at least 80 percent identical (e.g., 85, 87, 90, 91, 92, 93, 94, 95, 96, 97, 98, 99, or 100 percent identical) to the amino acid sequence $X_1IX_2X_3X_4X_5X_6X_7X_8X_9YX_{10}X_{11}X_{12}X_{13}KX_{14}$ (SEQ ID NO: 31), where $X_1$ is D, S, Y, or F, $X_2$ is K, T, S, or N, $X_3$ is Y, N, or P, $X_4$ is D, S, E, or Y, $X_5$ is G or S, $X_6$ is S, T, R, or G, $X_7$ is F, T, S, or Y, $X_8$ is I or T, $X_9$ is D, Y, H, or N, $X_{10}$ is A, R, G, or N, $X_{11}$ is P, D, or E, $X_{12}$ is S or K, $X_{13}$ is L, V, or F, and $X_{14}$ is N, G, A, S, or T; and the third heavy chain CDR (CDRH3) comprises an amino acid sequence that is at least 80 percent identical (e.g., 85, 87, 90, 91, 92, 93, 94, 95, 96, 97, 98, 99, or 100 percent identical) to the amino acid sequence $X_1X_2X_3X_4X_5X_6X_7X_8X_9X_{10}X_{11}X_{12}X_{13}X_{14}FX_{15}X_{16}$ (SEQ ID NO:32), where $X_1$ is D, E, H, or G, $X_2$ is L, G, or P, $X_3$ is T, G, or Y, $X_4$ is no amino acid, T, D, or G, $X_5$ is no amino acid, L or G, $X_6$ is no amino acid or Y, $X_7$ is V, Y, or S, $X_8$ is V, S, P, or G, $X_9$ is D or N, $X_{10}$ is G, Y, or W, $X_{11}$ is no amino acid or N, $X_{12}$ is no amino acid or Y, $X_{13}$ is no amino acid or V, $X_{14}$ is no amino acid, R or Y, $X_{15}$ is A or D, and $X_{16}$ is Y or F; and b) each immunoglobulin light chain variable domain of the anti-TLR7 agent comprises first, second, and third light chain CDRs, where the first light chain CDR (CDRL1) comprises an amino acid sequence that is at least 80 percent identical (e.g., 85, 87, 90, 91, 92, 93, 94, 95, 96, 97, 98, 99, or 100 percent identical) to the amino acid sequence $X_1X_2SX_3X_4X_5X_6X_7X_8X_9X_{10}$ (SEQ ID NO:33), where $X_1$ is R or L, $X_2$ is A or P, $X_3$ is E or Q, $X_4$ is D or S, $X_5$ is I or L, $X_6$ is Y or S, $X_7$ is N or T, $X_8$ is V, E, N, or S, $X_9$ is L or I, and $X_{10}$ is A or H; the second light chain CDR (CDRL2) comprises an amino acid sequence that is at least 80 percent identical (e.g., 85, 87, 90, 91, 92, 93, 94, 95, 96, 97, 98, 99, or 100 percent identical) to the amino acid sequence $X_1AX_2X_3X_4X_5X_6$ (SEQ ID NO:34), where $X_1$ is N or Y, $X_2$ is N or S, $X_3$ is R, N, S, or Q, $X_4$ is L or P, $X_5$ is H, Q, or I, and $X_6$ is N, T, D, or S; and the third light chain CDR (CDRL3) comprises an amino acid sequence that is at least 80 percent identical (e.g., 85, 87, 90, 91, 92, 93, 94, 95, 96, 97, 98, 99, or 100 percent identical) to the amino acid sequence $X_1QX_2X_3X_4X_5PX_6T$ (SEQ ID NO:35), where $X_1$ is Q or L, $X_2$ is Y, D, or S, $X_3$ is Y or S, $X_4$ is D or S, $X_5$ is Y or S, and $X_6$ is N, H, W, F, or Y.

Also provided in certain aspects is a first anti-TLR7 agent that binds TLR7 under laboratory or physiological conditions, where the first agent competitively binds with a second anti-TLR7 agent, which the second agent comprises at least one immunoglobulin heavy chain variable domain and at least one immunoglobulin light chain variable domain, where a) each immunoglobulin heavy chain variable domain of the second agent comprises first, second, and third heavy chain complementarity determining regions (CDRs), where the first heavy chain CDR (CDRH1) comprises an amino acid sequence that is at least 80 percent identical (e.g., 85, 87, 90, 91, 92, 93, 94, 95, 96, 97, 98, 99, or 100 percent identical) to the amino acid sequence $X_1YX_2X_3X_4$ (SEQ ID NO:30), where $X_1$ is D or N, $X_2$ is W, Y, or C, $X_3$ is M, V, or I, and $X_4$ is S, A, or H; the second heavy chain CDR (CDRH2) comprises an amino acid sequence that is at least 80 percent identical (e.g., 85, 87, 90, 91, 92, 93, 94, 95, 96, 97, 98, 99, or 100 percent identical) to the amino acid sequence $X_1IX_2X_3X_4X_5X_6X_7X_8X_9YX_{10}X_{11}X_{12}X_{13}KX_{14}$ (SEQ ID NO:31), where $X_1$ is D, S, Y, or F, $X_2$ is K, T, S, or N, $X_3$ is Y, N, or P, $X_4$ is D, S, E, or Y, $X_5$ is G or S, $X_6$ is S, T, R, or G, $X_7$ is F, T, S, or Y, $X_8$ is I or T, $X_9$ is D, Y, H, or N, $X_{10}$ is A, R, G, or N, $X_{11}$ is P, D, or E, $X_{12}$ is S or K, $X_{13}$ is L, V, or F, and $X_{14}$ is N, G, A, S, or T; and the third heavy chain CDR (CDRH3) comprises an amino acid sequence that is at least 80 percent identical (e.g., 85, 87, 90, 91, 92, 93, 94, 95, 96, 97, 98, 99, or 100 percent identical) to the amino acid sequence $X_1X_2X_3X_4X_5X_6X_7X_8X_9X_{10}X_{11}X_{12}X_{13}X_{14}FX_{15}X_{16}$ (SEQ ID NO:32), where $X_1$ is D, E, H, or G, $X_2$ is L, G, or P, $X_3$ is T, G, or Y, $X_4$ is no amino acid, T, D, or G, $X_5$ is no amino acid, L or G, $X_6$ is no amino acid or Y, $X_7$ is V, Y, or S, $X_8$ is V, S, P, or G, $X_9$ is D or N, $X_{10}$ is G, Y, or W, $X_{11}$ is no amino acid or N, $X_{12}$ is no amino acid or Y, $X_{13}$ is no amino acid or V, $X_{14}$ is no amino acid, R or Y, $X_{15}$ is A or D, and $X_{16}$ is Y or F; and b) each immunoglobulin light chain variable domain of the anti-TLR7 agent comprises first, second, and third light chain CDRs, where the first light chain CDR (CDRL1) comprises an amino acid sequence that is at least 80 percent identical (e.g., 85, 87, 90, 91, 92, 93, 94, 95, 96, 97, 98, 99, or 100 percent identical) to the amino acid sequence $X_1X_2SX_3X_4X_5X_6X_7X_8X_9X_{10}$ (SEQ ID NO:33), where $X_1$ is R or L, $X_2$ is A or P, $X_3$ is E or Q, $X_4$ is D or S, $X_5$ is I or L, $X_6$ is Y or S, $X_7$ is N or T, $X_8$ is V, E, N, or S, $X_9$ is L or I, and $X_{10}$ is A or H; the second light chain CDR (CDRL2) comprises an amino acid sequence that is at least 80 percent identical (e.g., 85, 87, 90, 91, 92, 93, 94, 95, 96, 97, 98, 99, or 100 percent identical) to the amino acid sequence $X_1AX_2X_3X_4X_5X_6$ (SEQ ID NO:34), where $X_1$ is N or Y, $X_2$ is N or S, $X_3$ is R, N, S, or Q, $X_4$ is L or P, $X_5$ is H, Q, or I, and $X_6$ is N, T, D, or S; and the third light chain CDR (CDRL3) comprises an amino acid sequence that is at least 80 percent identical (e.g., 85, 87, 90, 91, 92, 93, 94, 95, 96, 97, 98, 99, or 100 percent identical) to the amino acid sequence $X_1QX_2X_3X_4X_5PX_6T$ (SEQ ID NO:35), where $X_1$ is Q or L, $X_2$ is Y, D, or S, $X_3$ is Y or S, $X_4$ is D or S, $X_5$ is Y or S, and $X_6$ is N, H, W, F, or Y.

Also provided in certain aspects is a first anti-TLR7 agent that binds Toll-like Receptor 7 (TLR7) under laboratory or physiological conditions, where the first agent binds to the same epitope as a second anti-TLR7 agent, which the second agent comprises at least one immunoglobulin heavy chain variable domain and at least one immunoglobulin light chain variable domain, where a) each immunoglobulin heavy chain variable domain of the second agent comprises first, second, and third heavy chain complementarity determining regions (CDRs), where the first heavy chain CDR (CDRH1) comprises an amino acid sequence that is at least 80 percent identical (e.g., 85, 87, 90, 91, 92, 93, 94, 95, 96, 97, 98, 99, or 100 percent identical) to the amino acid sequence $X_1YX_2X_3X_4$ (SEQ ID NO:30), where $X_1$ is D or N, $X_2$ is W, Y, or C, $X_3$ is M, V, or I, and $X_4$ is S, A, or H; the second heavy chain CDR (CDRH2) comprises an amino acid sequence that is at least 80 percent identical (e.g., 85, 87, 90, 91, 92, 93, 94, 95, 96, 97, 98, 99, or 100 percent identical) to the amino acid sequence $X_1IX_2X_3X_4X_5X_6X_7X_8X_9YX_{10}X_{11}X_{12}X_{13}KX_{14}$ (SEQ ID NO:31), where $X_1$ is D, S, Y, or F, $X_2$ is K, T, S, or N, $X_3$ is Y, N, or P, $X_4$ is D, S, E, or Y, $X_5$ is G or S, $X_6$ is S, T, R, or G, $X_7$ is F, T, S, or Y, $X_8$ is I or T, $X_9$ is D, Y, H, or N, $X_{10}$ is A, R, G, or N, $X_{11}$ is P, D, or E, $X_{12}$ is S or K, $X_{13}$ is L, V, or F, and $X_{14}$ is N, G, A, S, or T; and the third heavy chain CDR (CDRH3) comprises an amino acid sequence that is at least 80 percent identical (e.g., 85, 87, 90, 91, 92, 93, 94, 95, 96, 97, 98, 99, or 100 percent identical) to the amino acid sequence $X_1X_2X_3X_4X_5X_6X_7X_8X_9X_{10}X_{11}X_{12}X_{13}X_{14}FX_{15}X_{16}$ (SEQ ID NO:32), where $X_1$ is D, E, H, or G, $X_2$ is L, G, or P, $X_3$ is T, G, or Y, $X_4$ is no amino acid, T, D, or G, $X_5$ is no amino acid, L or G, $X_6$ is no amino acid or Y, $X_7$ is V, Y, or S, $X_8$ is V, S, P, or G, $X_9$ is D or N, $X_{10}$ is G, Y, or W, $X_{11}$ is no amino acid or N, $X_{12}$ is no amino acid or Y, $X_{13}$ is no amino acid or V, $X_{14}$ is no amino acid, R or Y, $X_{15}$ is A or D, and $X_{16}$ is Y or F; and b) each immunoglobulin light chain variable domain of the anti-TLR7 agent comprises first, second, and third light chain CDRs, where the first light chain CDR (CDRL1) comprises an amino acid sequence that is at least 80 percent identical (e.g., 85, 87, 90, 91, 92, 93, 94, 95, 96, 97, 98, 99, or 100 percent identical) to the amino acid sequence $X_1X_2SX_3X_4X_5X_6X_7X_8X_9X_{10}$ (SEQ ID NO:33), where $X_1$ is R or L, $X_2$ is A or P, $X_3$ is E or Q, $X_4$ is D or S, $X_5$ is I or L, $X_6$ is Y or S, $X_7$ is N or T, $X_8$ is V, E, N, or S, $X_9$ is L or I, and $X_{10}$ is A or H; the second light chain CDR (CDRL2) comprises an amino acid sequence that is at least 80 percent identical (e.g., 85, 87, 90, 91, 92, 93, 94, 95, 96, 97, 98, 99, or 100 percent identical) to the amino acid sequence $X_1AX_2X_3X_4X_5X_6$ (SEQ ID NO:34), where $X_1$ is N or Y, $X_2$ is N or S, $X_3$ is R, N, S, or Q, $X_4$ is L or P, $X_5$ is H, Q, or I, and $X_6$ is N, T, D, or S; and the third light chain CDR (CDRL3) comprises an amino acid sequence that is at least 80 percent identical (e.g., 85, 87, 90, 91, 92, 93, 94, 95, 96, 97, 98, 99, or 100 percent identical) to the amino acid sequence $X_1QX_2X_3X_4X_5PX_6T$ (SEQ ID NO:35), where $X_1$ is Q or L, $X_2$ is Y, D, or S, $X_3$ is Y or S, $X_4$ is D or S, $X_5$ is Y or S, and $X_6$ is N, H, W, F, or Y.

Also provided in certain aspects are anti-TLR7 agents for detecting TLR7 in a heterogeneous population of immune cells, where TLR7 is detected at a significant level in plasmacytoid dendritic cells (pDCs) and/or B cells in the population, and TLR7 is not significantly detected in other immune cells in the population.

Also provided in certain aspects are methods of detecting TLR7 in a heterogeneous population of immune cells, comprising contacting the population with an anti-TLR7 agent provided herein, where TLR7 is not significantly detected in other immune cells in the population.

In one aspect, provided herein are isolated, non-naturally occurring anti-TLR7 agents, particularly antibodies, or antigen-binding fragments or derivatives thereof, that bind Toll-like receptor 7 (TLR7) under physiological conditions. In the context of anti-TLR7 antibodies or antigen-binding fragments, such molecules generally comprise two immunoglobulin heavy chain variable domains and two immunoglobulin light chain variable domains. In such molecules, each of the immunoglobulin heavy and light chain variable domains comprise first, second, and third chain complementarity determining regions (CDRs) arrayed as follows: FR1-CDR1-FR2-CDR2-FR3-CDR3-FR4.

In the heavy chain variable domain portions, the first heavy chain CDR (CDRH1) comprises an amino acid sequence that has a sequence identity of at least 65 percent, optionally a sequence identity of at least 80 percent, at least 90 percent, at least 95 percent, and 100 percent identity with the amino acid sequence DYWMS, NYYMA, DYYMA, DYCVH, or DYYIH (SEQ ID NOS: 1-5, respectively), the second heavy chain CDR (CDRH2) comprises an amino acid sequence that has a sequence identity of at least 65 percent, optionally a sequence identity of at least 80 percent, at least 90 percent, at least 95 percent, and 100 percent identity with the amino acid sequence DIKYDGSFIDY-APSLKN, DIKYDGTFIDYAPSLKN, SITNSGRT-TYYRDSVKG, SISYEGSSTHYGDSVKA, YINPYSGYTNYNEKFKS, or FINPDSGYTNYNEKFKT (SEQ ID NOS: 6-11, respectively), and the third heavy chain CDR (CDRH3) comprises an amino acid sequence that has a sequence identity of at least 65 percent, optionally a sequence identity of at least 80 percent, at least 90 percent, at least 95 percent, and 100 percent identity with the amino acid sequence DLTTVVDGFAY, DLTTVVDGFAY, EGGD-LYYSNYNYVRFAY, HGGYPNWYFDF, or GPYG-GYSGDGFDY (SEQ ID NOS: 12-15, respectively).

In the light chain variable domain portions, the first light chain CDR (CDRL1) comprises an amino acid sequence that has a sequence identity of at least 65 percent, optionally a sequence identity of at least 80 percent, at least 90 percent, at least 95 percent, and 100 percent identity with the amino acid sequence RASEDIYNVLA, RASEDIYNELA, LPSEDIYNNLA, or RASQSLSTSIH (SEQ ID NOS: 16-19, respectively), the second light chain CDR (CDRL2) comprises an amino acid sequence that has a sequence identity of at least 65 percent, optionally a sequence identity of 100 percent identity with the amino acid sequence NANRLHN, NANNLHT, NANSLHT, YASNLQD, or YASQPIS (SEQ ID NOS: 20-24, respectively), and the third light chain CDR (CDRL3) comprises an amino acid sequence that has a sequence identity of at least 65 percent, optionally a sequence identity of at least 80 percent, at least 90 percent, at least 95 percent, and 100 percent identity with the amino acid sequence QQYYDYPNT, QQYYDYPHT, QQYYDYPWT, LQDSDYPFT, or QQSYSSPYT (SEQ ID NOS: 25-29, respectively).

In some embodiments, the isolated, non-naturally occurring anti-TLR7 antibodies, or TLR7-binding fragments thereof, including a first heavy chain CDR having the amino acid sequence DYYIH (SEQ ID NO:5), the second heavy chain CDR has the amino acid sequence FINPDSGYTNYNEKFKT (SEQ ID NO:11), the third heavy chain CDR has the amino acid sequence GPYG-GYSGDGFDY (SEQ ID NO:15), the first light chain CDR has the amino acid sequence RASQSLSTSIH (SEQ ID NO:19), the second light chain CDR has the amino acid sequence YASQPIS (SEQ ID NO:24), and the third light chain CDR has the amino acid sequence QQSYSSPYT (SEQ ID NO:29).

In some embodiments, the isolated anti-TLR7 agent comprises a non-naturally occurring anti-TLR7 antibody (mAb) comprising two immunoglobulin heavy chain variable domains comprising first, second, and third heavy chain complementarity determining regions (CDRH1-3, respectively) and two immunoglobulin light chain variable domains comprising first, second, and third light chain complementarity determining regions (CDRL1-3, respectively), where the antibody comprises immunoglobulin heavy chain variable domains and immunoglobulin light chain variable domains having sets of CDRH1-3 and CDRL1-3 selected from the group consisting of:

TABLE 1

| | | | | | | |
|---|---|---|---|---|---|---|
| mAb | CDRH1 (SEQ ID NO:) | CDRH2 (SEQ ID NO:) | CDRH3 (SEQ ID NO:) | CDRL1 (SEQ ID NO:) | CDRL2 (SEQ ID NO:) | CDRL3 (SEQ ID NO:) |
| 1 | DYWMS (1) | DIKYDGSFIDYA PSLKN (6) | DLTTVVDGFAY (12) | RASQSLSTSIH (19) | YASQPIS (24) | QQSYSSPYT (29) |
| 2 | DYWMS (1) | DIKYDGTFIDYA PSLKN (7) | DLTTVVDGFAY (12) | RASQSLSTSIH (19) | YASQPIS (24) | QQSYSSPYT (29) |
| 3 | NYYMA (2) | SITNSGRTTYY RDSVKG (8) | EGGDLYYSNYN YVRFAY (13) | LPSEDIYNNLA (18) | YASNLQD (23) | LQDSDYPFT (28) |
| 4 | DYYMA (3) | SISYEGSSTHY GDSVKA (9) | HGGYPNWYFD F (14) | RASEDIYNELA (17) | NANSLHT (22) | QQYYDYPWT (27) |
| 5 | DYCVH (4) | YINPYSGYTNY NEKFKS (10) | GPYGGYSGDG FDY (15) | RASEDIYNVLA (16) | NANRLHN (20) | QQYYDYPNT (25) |
| 6 | DYYIH (5) | FINPDSGYTNY NEKFKT (11) | GPYGGYSGDG FDY (15) | RASEDIYNVLA (16) | NANNLHT (21) | QQYYDYPHT (26) |

CDR Sequences of anti-TLR7 antibodies (Kabat numbering scheme)

In some embodiments, the isolated anti-TLR7 agent comprises a non-naturally occurring anti-TLR7 antibody (mAb) comprising two immunoglobulin heavy chain variable domains and two immunoglobulin light chain variable domains, where the immunoglobulin heavy chain variable domains have an amino acid sequence selected from among SEQ ID NOS:36-41 or an amino acid sequence having at least 65%-95% or more sequence identity with any such heavy chain variable domain sequence and the immunoglobulin light chain variable domains are selected from am on SEQ ID NOS:42-47 or an amino acid sequence having at least 65%-95% or more sequence identity with any such light chain variable domain sequence.

In some embodiments, where the anti-TLR7 agents are antibodies, or antigen-binding antibody fragments thereof, the antibodies (or fragments thereof) are monoclonal antibodies, and may be camel, human, humanized, mouse, rabbit, or other mammalian antibodies or antigen-binding antibody fragments. In some embodiments, the antibody (antigen-binding antibody fragment) is an IgG. In other embodiments, the IgG is an IgG1, IgG2a or IgG2b, or IgG3, or IgG4.

In certain embodiments of anti-TLR7 antibodies and antigen-binding antibody fragments that are other than fully human antibodies (i.e., antibodies produced or derived from a mammal capable of producing all or a portion of the human antibody repertoire), the molecules are chimeric or humanized anti-TLR7 antibodies and antigen-binding antibody fragments.

In some embodiments, the anti-TLR7 antibody, antigen-binding antibody fragment, or derivative or variant thereof includes a detectable label.

In some embodiments, the anti-TLR7 agent, for example, an anti-TLR7 antibody, antigen-binding antibody fragment, or derivative or variant thereof, is part of an immunoconjugate that further includes a cytotoxic agent, for example, a nucleic acid, a peptide, a polypeptide, a small molecule, or an aptamer.

A related aspect of technology described herein concerns compositions that include an anti-TLR7 agent that is an isolated, non-naturally occurring anti-TLR7 antibody or antigen-binding antibody fragment according to the technology described herein. In addition to containing an anti-TLR7 antibody or an antigen-binding antibody fragment described herein, such compositions typically also include a carrier, for example, a pharmaceutically acceptable carrier. Such compositions may be packaged in containers, which in some embodiments, are further packaged into kits that also include instructions for use. In the context of pharmaceutical compositions, such kits instructions are a package insert containing not only instructions or use but also information about the pharmaceutically active ingredient (e.g., the anti-TLR7 antibody, antigen-binding antibody fragment, or derivative or variant thereof).

Another related aspect concerns diagnostics configured to detect TLR7 in a biological sample, often a biological sample taken from a subject. Such kits include a diagnostic reagent that includes an anti-TLR7 agent described herein, for example, an anti-TLR7 antibody, antigen-binding antibody fragment, or derivative or variant thereof conjugated with detectable reagents such as fluorophores or enzyme substrates and/or immobilized on a solid support.

Still other aspects of technology provided herein concern the manufacture of an anti-TLR7 agent described herein. In the context of anti-TLR7 antibodies (or antigen-binding antibody fragments or derivatives or variants thereof), one such aspect concerns isolated nucleic acid molecules that encode polypeptides provided herein. In some embodiments, such nucleic acids encode an immunoglobulin heavy chain variable domain having a first heavy chain CDR (CDRH1) that includes an amino acid sequence that has a sequence identity of at least 65%, optionally a sequence identity of at least 70%, at least 75%, at least 80%, at least 85%, at least 87%, at least 90%, at least 91%, at least 93%, at least 95%, at least 97%, at least 99%, or 100% identity with the amino acid sequence DYWMS, NYYMA, DYYMA, DYCVH, or DYYIH (SEQ ID NOS: 1-5, respectively), a second heavy chain CDR (CDRH2) that includes an amino acid sequence that has a sequence identity of at least 65%, optionally a sequence identity of at least 70%, at least 75%, at least 80%, at least 85%, at least 87%, at least 90%, at least 91%, at least 93%, at least 95%, at least 97%, at least 99%, or 100% identity with the amino acid sequence DIKYDGSFIDYAPSLKN, DIKYDGTFIDYAPSLKN, SITNSGRTTYYRDSVKG, SISYEGSSTHYGDSVKA, YINPYSGYTNYNEKFKS, or FINPDSGYTNYNEKFKT (SEQ ID NOS: 6-11, respectively), and a third heavy chain CDR (CDRH3) that includes an amino acid sequence that has a sequence identity of at least 65%, optionally a sequence identity of at least 70%, at least 75%, at least 80%, at least 85%, at least 87%, at least 90%, at least 91%, at least 93%, at least 95%, at least 97%, at least 99%, or 100% identity with the amino acid sequence DLTTVVDGFAY, DLTTVVDGFAY, EGGDLYYSNYNYVRFAY, HGGYPNWYFDF, or GPYGGYSGDGFDY (SEQ ID NOS: 12-15, respectively). Such nucleic acids may also encode an immunoglobulin light chain variable domain where a first light chain CDR (CDRL1) that includes an amino acid sequence that has a sequence identity of at last 65%, optionally a sequence identity of at least 70%, at least 75%, at least 80%, at least 85%, at least 87%, at least 90%, at least 91%, at least 93%, at least 95%, at least 97%, at least 99%, or 100% identity with the amino acid sequence RASEDIYNVLA, RASEDIYNELA, LPSEDIYNNLA, or RASQSLSTSIH (SEQ ID NOS: 16-19, respectively), a second light chain CDR (CDRL2) that includes an amino acid sequence that has a sequence identity of at least 65%, optionally a sequence identity of at least 70%, at least 75%, at least 80%, at least 85%, at least 87%, at least 90%, at least 91%, at least 93%, at least 95%, at least 97%, at least 99%, or 100% identity with the amino acid sequence NANRLHN, NANNLHT, NANSLHT, YASNLQD, or YASQPIS (SEQ ID NOS: 20-24, respectively), and a third light chain CDR (CDRL3) that includes an amino acid sequence that has a sequence identity of at least 65%, optionally a sequence identity of at least 70%, at least 75%, at least 80%, at least 85%, at least 87%, at least 90%, at least 91%, at least 93%, at least 95%, at least 97%, at least 99%, or 100% identity with the amino acid sequence QQYYDYPNT, QQYYDYPHT, QQYYDYPWT, LQDSDYPFT, or QQSYSSPYT (SEQ ID NOS: 25-29, respectively).

In certain embodiments, nucleic acid molecules provided herein encode an immunoglobulin heavy chain variable domain having an amino acid sequence selected from among SEQ ID NOS:36-41 or an amino acid sequence having at least 65%-95% or more sequence identity with any such heavy chain variable domain sequence and an immunoglobulin light chain variable domain having an amino acid sequence selected from among SEQ ID NOS:42-47 or an amino acid sequence having at least 65%-95% or more sequence identity with any such light chain variable domain sequence.

Related aspects concern plasmids, and expression cassettes and vectors, that carry nucleic acids provided herein, as well as recombinant host cells transfected with such nucleic acid molecules.

Still other aspects of the technology provided herein concern methods of treating or preventing a disease or disorder associated with aberrant levels of TLR7 (e.g., cancer, infection, tissue damage, autoimmune disease, inflammation, and the like). Such methods include administering to a subject in need of such treatment an anti-TLR7 agent provided herein (e.g., an anti-TLR7 antibody or antigen-binding fragment, derivative, or variant thereof) in an amount sufficient to effect treatment, thereby treating or preventing the disease or disorder. Such diseases and disorders that can be so treated include non-viral cancers (e.g., breast, glioma, prostate, non-small cell lung cancer, ovarian, and the like), virus-associated cancers such as cervical cancer associated with human papilloma virus (HPV) infection, cancers associated with HBV infection (e.g., hepatocellular carcinoma), cancers associated with Epstein-Barr virus (EBV) infection, cancers associated with polyomavirus infection, erythema nodosum leprosum (ENL), autoimmune diseases (e.g., systemic lupus erythematosus), autoimmune inflammation, autoimmune thyroid diseases associated with increased TLR7 expression, B-cell lymphoma, T-cell lymphoma, acute myeloid leukemia, Hodgkin's Disease, acute myelogenous leukemia, acute myelomonocytic leukemia, acute lymphoblastic leukemia, chronic myelogenous leukemia, chronic lymphocytic leukemia, B cell large cell lymphoma, malignant lymphoma, acute leukemia, lymphosarcoma cell leukemia, B-cell leukemias, myelodysplastic syndromes, solid phase cancer, herpes viral infections, and rejection of transplanted tissues or organs, and the like. In certain instances, an anti-TLR7 agent provided herein (e.g., an anti-TLR7 antibody or antigen-binding fragment, derivative, or variant thereof) may be used as an adjuvant or in conjunction with an adjuvant (e.g., for vaccines).

Further aspects of the technology provided herein concern diagnostic methods of using an anti-TLR7 agent provided herein, for example, in vitro or in vivo diagnostic assays to detect the presence of TLR7.

Certain embodiments are described further in the following description, examples, claims and drawings.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

FIG. 1 shows the amino acid sequence of a representative full-length human TLR7 precursor (SEQ ID NO:48). In the sequence, the amino acid residues that make up the signal peptide (residues 1-26) are underlined. Residues 27-1,049 comprise the mature, processed form of the protein. See, e.g., NCBI Reference Sequence: NP_057646.1.

FIG. 2 shows the amino acid sequences of the variable domains of the immunoglobulin heavy (SEQ ID NOS:36-41) and light (SEQ ID NOS:42-47) chains of 6 different anti-TLR7 antibodies (AB 1-6) provided herein. The CDR regions of each of the heavy and light chains are shown in bold and are underlined. In each of the alignments, three characters ("*", ":", and ".") are used: "*" indicates positions that have a single, fully conserved residue; ":" indicates that one of the following "strong" residue groups is fully conserved: STA; NEQK; NHQK; NDEQ; QHRK; MILV; MILF; HY; and FYW; and "." indicates that one of the following "weaker" residue groups is fully conserved: CSA; ATV; SAG; STNK; STPA; SGND; SNDEQK; NDEQHK; NEQHRK; FVLIM; and HFY. These are all the positively scoring residue groups that occur in the Gonnet Pam250 matrix. The "strong" and "weak" residue groups are defined as "strong" score>0.5 and "weak" score<0.5, respectively.

FIG. 3 lists information for anti-TLR7 antibodies used in the experiments described in the Examples, below.

FIG. 5, panels A-D show histograms plotting results of experiments described in the Example 3, below.

FIG. 6, panels A-D, show histograms plotting results of experiments described in Example 3, below.

FIGS. 7A-7F show mean fluorescence intensities (MFI) (FIGS. 7A, 7C, and 7E) and signal to noise ratios (S:N;

FIGS. 7B, 7D, and 7F) of the results presented in FIG. 6 for pDCs, B cells, and monocytes.

FIGS. 8A and 8B show IL-8 secretion by 293XL-hTLR7 cells following treatment with R848 and hTLR7 antibody provided herein. Dotted line shows cells treated with R848 only. FIG. 8A shows a representative plot showing IL-8 secretion. FIG. 8B shows fold change in IL-8 secretion with antibody treatment relative to R848 treatment with isotype antibody.

DETAILED DESCRIPTION

Figures 4A, 4B, 4C:
FIGS. 4A-4C are scatter plots showing the results of the gating strategy used for the flow cytometry experiments described in Example 3, below.

Provided herein are agents that bind TLR7. In some aspects, antibodies, and fragments thereof, that bind to TLR7 are provided herein. For example, particular monoclonal antibodies to TLR7 that provide superior target specificity, signal-to-noise ratios, and the like as compared to other reported anti-TLR7 antibodies, as well as antigen-binding fragments of such antibodies that bind TLR7, are described herein. Also provided herein are methods for producing anti-TLR7 agents, particularly anti-TLR7 antibodies, with desirable properties including affinity and/or specificity for TLR7 and/or its variants.

Antibody Generation and Characterization

Anti-TLR7 agents (e.g., anti-TLR7 antibodies) provided herein may have a strong binding affinity and/or specificity for TLR7. In some embodiments, anti-TLR7 agents may be chimeric antibodies. In some embodiments, anti-TLR7 agents may be humanized antibodies. In some embodiments, anti-TLR7 agents may be variant antibodies. Antibodies, for example, may have beneficial properties from a therapeutic perspective. Assays for determining the activity of anti-TLR7 antibodies provided herein include, for example, cell-based ELISA (e.g., to measure relative avidity of the antibody for the target on cells), flow cytometry (e.g., to measure cell specificity of the antibody), and cytotoxicity (e.g., to measure potential to mediate direct or indirect killing of TLR7-expressing target cells). In certain instances, a humanized or variant antibody fails to elicit an immunogenic response upon administration of a therapeutically effective amount of the antibody to a human patient. In certain instances, if an immunogenic response is elicited, the response may be such that the antibody still provides a therapeutic benefit to the patient treated therewith.

In some embodiments, anti-TLR7 agents (e.g., anti-TLR7 antibodies, humanized anti-TLR7 antibodies) herein bind the same epitope. To screen for antibodies that bind to an epitope on TLR7 bound by an antibody of interest (e.g., those that block binding of the antibody to TLR7), a cross-blocking assay such as that described in Antibodies, A Laboratory Manual, Cold Spring Harbor Laboratory, Ed Harlow and David Lane (1988), can be performed. In certain instances, epitope mapping, e.g. as described in Champe et al., J. Biol. Chem. 270:1388-1394 (1995), in Cunningham and Wells, Science 244:1081-1085 (1989) or in Davidson and Doranz, Immunology 143: 13-20 (2014), can be performed to determine whether the antibody binds an epitope of interest.

Antibodies herein generally have a heavy chain variable domain comprising an amino acid sequence represented by the formula: FRH1-CDRH1-FRH2-CDRH2-FRH3-CDRH3-FRH4, where "FRH1-4" represents the four heavy chain framework regions and "CDRH1-3" represents the three hypervariable regions of an anti-TLR7 antibody variable heavy domain. FRH1-4 may be derived from a consensus sequence (for example the most common amino acids of a class, subclass or subgroup of heavy or light chains of human immunoglobulins) or may be derived from an individual human antibody framework region or from a combination of different framework region sequences. Many human antibody framework region sequences are compiled in Kabat et al. (1992) SEQUENCES OF PROTEINS OF IMMUNOLOGICAL INTEREST, National Institutes of Health Publication No. 91-3242, for example. In one embodiment, the variable heavy FR is provided by a consensus sequence of a human immunoglobulin subgroup as compiled by Kabat et al., supra.

The human variable heavy FR sequence may have substitutions therein, e.g. where the human FR residue is replaced by a corresponding nonhuman residue (by "corresponding nonhuman residue" is meant the nonhuman residue with the same Kabat positional numbering as the human residue of interest when the human and nonhuman sequences are aligned), but replacement with the nonhuman residue is not necessary. For example, a replacement FR residue other than the corresponding nonhuman residue may be selected by phage display.

Antibodies herein may have a light chain variable domain comprising an amino acid sequence represented by the formula: FRL1-CDRL1-FRL2-CDRL2-FRL3-CDRL3-FRL4, where "FRL1-4" represents the four framework regions and "CDRL1-3" represents the three hypervariable regions of an anti-TLR7 antibody variable light domain. FRL1-4 may be derived from a consensus sequence (for example the most common amino acids of a class, subclass or subgroup of heavy or light chains of human immunoglobulins) or may be derived from an individual human antibody framework region or from a combination of different framework region sequences. In one embodiment, the variable light FR is provided by a consensus sequence of a human immunoglobulin subgroup as compiled by Kabat et al., supra.

The human variable light FR sequence may have substitutions therein, e.g. where the human FR residue is replaced by a corresponding mouse residue, but replacement with the nonhuman residue is not necessary. For example, a replacement residue other than the corresponding nonhuman residue may be selected by phage display. Methods for generating humanized anti-TLR7 antibodies of interest herein are elaborated in more detail below.

Anti-TLR7 Agents

Provided herein are agents that bind Toll-like Receptor 7 (TLR7). Such agents may be referred to as anti-TLR7 agents and may include anti-TLR7 antibodies, anti-TLR7 antibody fragments (e.g., antigen binding fragments), and anti-TLR7 antibody derivatives. In some embodiments, the agent is isolated (e.g., separated from a component of its natural environment (e.g. an animal, a biological sample)). In some embodiments, the agent is non-naturally occurring (e.g., produced by human intervention). In some embodiments, the agent is a humanized antibody, or an antigen binding fragment thereof. In some embodiments, the agent is a derivative of a humanized antibody that binds TLR7. In some embodiments, the agent binds TLR7 under laboratory conditions (e.g., binds TLR7 in vitro, binds TLR7 in a flow cytometry assay, binds TLR7 in an ELISA). In some embodiments, the agent binds TLR7 under physiological conditions (e.g., binds TLR7 in a cell in a subject).

Generally, the anti-TLR7 agent provided herein comprises at least one immunoglobulin heavy chain variable domain and at least one immunoglobulin light chain variable domain. In some embodiments, an anti-TLR7 agent herein comprises two immunoglobulin heavy chain variable domains and two immunoglobulin light chain variable domains. Typically, each immunoglobulin heavy chain variable domain of the anti-TLR7 agent comprises first, second, and third heavy chain complementarity determining regions (CDRs; CDRH1, CDRH2, CDRH3), and each immunoglobulin light chain variable domain of the anti-TLR7 agent comprises first, second, and third light chain CDRs (DCRL1, CDRL2, CDRL3).

CDRH1

In some embodiments, the first heavy chain CDR (CDRH1) of an anti-TLR7 agent provided herein comprises an amino acid sequence that is at least 80% identical to the amino acid sequence $X_1YX_2X_3X_4$ (SEQ ID NO:30), where $X_1$ is D or N; $X_2$ is W, Y, or C; $X_3$ is M, V, or I; and $X_4$ is S, A, or H. In some embodiments, the CDRH1 comprises an amino acid sequence that is at least 90% identical to the amino acid sequence of SEQ ID NO:30. In some embodiments, the CDRH1 comprises an amino acid sequence that is at least 95% identical to the amino acid sequence of SEQ ID NO:30. In some embodiments, the CDRH1 comprises an amino acid sequence that is 100% identical to the amino acid sequence of SEQ ID NO:30.

The amino acid $X_1$ of SEQ ID NO:30 may be substituted with any amino acid. In some embodiments, the amino acid $X_1$ of SEQ ID NO:30 is substituted with a conservative amino acid (e.g., conservative to D and/or N). In some embodiments, the amino acid $X_1$ of SEQ ID NO:30 is substituted with an acidic amino acid. In some embodiments, the amino acid is substituted with a basic amino acid.

The amino acid $X_2$ of SEQ ID NO:30 may be substituted with any amino acid. In some embodiments, the amino acid of SEQ ID NO:30 is substituted with a conservative amino acid (e.g., W, Y and/or C). In some embodiments, the amino acid $X_2$ of SEQ ID NO:30 is substituted with an aromatic amino acid. In some embodiments, the amino acid $X_2$ of SEQ ID NO:30 is substituted with a neutral hydrophilic amino acid.

The amino acid $X_3$ of SEQ ID NO:30 may be substituted with any amino acid. In some embodiments, the amino acid of $X_3$ of SEQ ID NO:30 is substituted with a conservative amino acid (e.g., conservative to M, V, and/or I). In some embodiments, the amino acid $X_3$ of SEQ ID NO:30 is substituted with a hydrophobic amino acid.

The amino acid $X_4$ of SEQ ID NO:30 may be substituted with any amino acid. In some embodiments, the amino acid of $X_4$ of SEQ ID NO:30 is substituted with a conservative amino acid (e.g., conservative to S, A, and/or H). In some embodiments, the amino acid $X_4$ of SEQ ID NO:30 is substituted with a neutral hydrophilic amino acid. In some embodiments, the amino acid $X_4$ of SEQ ID NO:30 is substituted with a hydrophobic amino acid. In some embodiments, the amino acid $X_4$ of SEQ ID NO:30 is substituted with a basic amino acid.

In some embodiments, the CDRH1 of anti-TLR7 agent provided herein comprises an amino acid sequence chosen from DYWMS (SEQ ID NO: 1), NYYMA (SEQ ID NO: 2), DYYMA (SEQ ID NO: 3), DYCVH (SEQ ID NO: 4), and DYYIH (SEQ ID NO: 5).

CDRH2

In some embodiments, the second heavy chain CDR (CDRH2) of an anti-TLR7 agent provided herein comprises an amino acid sequence that is at least 80 percent identical (e.g., 85, 87, 90, 91, 92, 93, 94, 95, 96, 97, 98, 99, or 100 percent identical) to the amino acid sequence $X_1IX_2X_3X_4X_5X_6X_7X_8X_9YX_{10}X_{11}X_{12}X_{13}KX_{14}$ (SEQ ID NO:31), where $X_1$ is D, S, Y, or F; $X_2$ is K, T, S, or N; $X_3$ is Y, N, or P; $X_4$ is D, S, E, or Y; $X_5$ is G or S; $X_6$ is S, T, R, or G; $X_7$ is F, T, S, or Y; $X_8$ is I or T; $X_9$ is D, Y, H, or N; $X_{10}$ is A, R, G, or N; $X_{11}$ is P, D, or E; $X_{12}$ is S or K; $X_{13}$ is L, V, or F; and $X_{14}$ is N, G, A, S, or T. In some embodiments, the CDRH2 comprises an amino acid sequence that is at least 90 percent identical to the amino acid sequence of SEQ ID NO: 31. In some embodiments, the CDRH2 comprises an amino acid sequence that is at least 95 percent identical to the amino acid sequence of SEQ ID NO:31. In some embodiments, the CDRH2 comprises an amino acid sequence that is 100 percent identical to the amino acid sequence of SEQ ID NO:31.

The amino acid $X_1$ of SEQ ID NO:31 may be substituted with any amino acid. In some embodiments, the amino acid $X_1$ of SEQ ID NO:31 is substituted with a conservative amino acid (e.g., conservative to D, S, Y, and/or F). In some embodiments, the amino acid $X_1$ of SEQ ID NO:31 is substituted with an acidic amino acid. In some embodiments, the amino acid $X_1$ of SEQ ID NO:31 is substituted with a neutral hydrophilic amino acid. In some embodiments, the amino acid $X_1$ of SEQ ID NO:31 is substituted with an aromatic amino acid.

The amino acid $X_2$ of SEQ ID NO:31 may be substituted with any amino acid. In some embodiments, the amino acid $X_2$ of SEQ ID NO:31 is substituted with a conservative amino acid (e.g., conservative to K, T, S, and/or N). In some embodiments, the amino acid $X_2$ of SEQ ID NO:31 is substituted with a basic amino acid. In some embodiments, the amino acid $X_2$ of SEQ ID NO:31 is substituted with a neutral hydrophilic amino acid. In some embodiments, the amino acid $X_2$ of SEQ ID NO:31 is substituted with a basic amino acid.

The amino acid $X_3$ of SEQ ID NO: 31 may be substituted with any amino acid. In some embodiments, the amino acid $X_3$ of SEQ ID NO:31 is substituted with a conservative amino acid (e.g., conservative to Y, N, and/or P). In some embodiments, the amino acid $X_3$ of SEQ ID NO:31 is substituted with an aromatic amino acid. In some embodiments, the amino acid $X_3$ of SEQ ID NO:31 is substituted with a basic amino acid. In some embodiments, the amino acid $X_3$ of SEQ ID NO:31 is substituted with an amino acid residue that influences chain orientation.

The amino acid $X_4$ of SEQ ID NO:31 may be substituted with any amino acid. In some embodiments, the amino acid $X_4$ of SEQ ID NO:31 is substituted with a conservative amino acid (e.g., conservative to D, S, E, and/or Y). In some embodiments, the amino acid $X_4$ of SEQ ID NO:31 is substituted with an acidic amino acid. In some embodiments, the amino acid $X_4$ of SEQ ID NO:31 is substituted with a neutral hydrophilic amino acid. In some embodiments, the amino acid $X_4$ of SEQ ID NO:31 is substituted with an aromatic amino acid.

The amino acid $X_5$ of SEQ ID NO:31 may be substituted with any amino acid. In some embodiments, the amino acid $X_5$ of SEQ ID NO:31 is substituted with a conservative amino acid (e.g., conservative to G and/or S). In some embodiments, the amino acid $X_5$ of SEQ ID NO:31 is substituted with an amino acid residue that influences chain orientation. In some embodiments, the amino acid $X_5$ of SEQ ID NO:31 is substituted with a neutral hydrophilic amino acid.

The amino acid $X_6$ of SEQ ID NO:31 may be substituted with any amino acid. In some embodiments, the amino acid $X_6$ of SEQ ID NO:31 is substituted with a conservative amino acid (e.g., conservative to S, T, R, and/or G). In some embodiments, the amino acid $X_6$ of SEQ ID NO:31 is substituted with a neutral hydrophilic amino acid. In some embodiments, the amino acid $X_6$ of SEQ ID NO:31 is substituted with a basic amino acid. In some embodiments, the amino acid $X_6$ of SEQ ID NO:31 is substituted with an amino acid that influences chain orientation.

The amino acid $X_7$ of SEQ ID NO:31 may be substituted with any amino acid. In some embodiments, the amino acid $X_7$ of SEQ ID NO:31 is substituted with a conservative amino acid (e.g., conservative to F, T, S, and/or Y). In some embodiments, the amino acid $X_7$ of SEQ ID NO:31 is substituted with an aromatic amino acid. In some embodiments, the amino acid $X_7$ of SEQ ID NO:31 is substituted with a neutral hydrophilic amino acid.

The amino acid $X_8$ of SEQ ID NO:31 may be substituted with any amino acid. In some embodiments, the amino acid $X_8$ of SEQ ID NO:31 is substituted with a conservative amino acid (e.g., conservative to I and/or T). In some embodiments, the amino acid $X_8$ of SEQ ID NO:31 is substituted with a hydrophobic amino acid. In some embodiments, the amino acid $X_8$ of SEQ ID NO:31 is substituted with a neutral hydrophilic amino acid.

The amino acid $X_9$ of SEQ ID NO:31 may be substituted with any amino acid. In some embodiments, the amino acid $X_9$ of SEQ ID NO:31 is substituted with a conservative amino acid (e.g., conservative to D, Y, H, and/or N). In some embodiments, the amino acid $X_9$ of SEQ ID NO:31 is substituted with an acidic amino acid. In some embodiments, the amino acid $X_9$ of SEQ ID NO:31 is substituted with an aromatic amino acid. In some embodiments, the amino acid $X_9$ of SEQ ID NO:31 is substituted with a basic amino acid.

The amino acid $X_{10}$ of SEQ ID NO:31 may be substituted with any amino acid. In some embodiments, the amino acid $X_{10}$ of SEQ ID NO:31 is substituted with a conservative amino acid (e.g., conservative to A, R, G, and/or N). In some embodiments, the amino acid $X_{10}$ of SEQ ID NO:31 is substituted with a hydrophobic amino acid. In some embodiments, the amino acid $X_{10}$ of SEQ ID NO:31 is substituted with a basic amino acid. In some embodiments, the amino acid $X_{10}$ of SEQ ID NO:31 is substituted with an amino acid residue that influences chain orientation.

The amino acid $X_{11}$ of SEQ ID NO:31 may be substituted with any amino acid. In some embodiments, the amino acid $X_{11}$ of SEQ ID NO:31 is substituted with a conservative amino acid (e.g., conservative to P, D, and/or E). In some embodiments, the amino acid $X_{11}$ of SEQ ID NO:31 is substituted with an amino acid residue that influences chain orientation. In some embodiments, the amino acid $X_{11}$ of SEQ ID NO:31 is substituted with an acidic amino acid.

The amino acid $X_{12}$ of SEQ ID NO:31 may be substituted with any amino acid. In some embodiments, the amino acid $X_{12}$ of SEQ ID NO:31 is substituted with a conservative amino acid (e.g., conservative to S and/or K). In some embodiments, the amino acid $X_{12}$ of SEQ ID NO:31 is substituted with a neutral hydrophilic amino acid. In some embodiments, the amino acid $X_{12}$ of SEQ ID NO:31 is substituted with a basic amino acid.

The amino acid $X_{13}$ of SEQ ID NO:31 may be substituted with any amino acid. In some embodiments, the amino acid $X_{13}$ of SEQ ID NO:31 is substituted with a conservative amino acid (e.g., conservative to L, V, and/or F). In some embodiments, the amino acid $X_{13}$ of SEQ ID NO:31 is substituted with a hydrophobic amino acid. In some embodiments, the amino acid $X_{13}$ of SEQ ID NO:31 is substituted with an aromatic amino acid.

The amino acid $X_{14}$ of SEQ ID NO:31 may be substituted with any amino acid. In some embodiments, the amino acid $X_{14}$ of SEQ ID NO:31 is substituted with a conservative amino acid (e.g., conservative to N, G, A, S, and/or T). In some embodiments, the amino acid $X_{14}$ of SEQ ID NO:31 is substituted with a basic amino acid. In some embodiments, the amino acid $X_{14}$ of SEQ ID NO:31 is substituted with an amino acid that influences chain residue. In some embodiments, the amino acid $X_{14}$ of SEQ ID NO:31 is substituted with a hydrophobic amino acid. In some embodiments, the amino acid $X_{14}$ of SEQ ID NO: 31 is substituted with a neutral hydrophilic amino acid.

In some embodiments, the CDRH2 of anti-TLR7 agent provided herein comprises an amino acid sequence chosen from DIKYDGSFIDYAPSLKN (SEQ ID NO: 6), DIKYDGTFIDYAPSLKN (SEQ ID NO: 7), SITNSGRT-TYYRDSVKG (SEQ ID NO: 8), SISYEGSSTHYGDSVKA (SEQ ID NO: 9), YINPYSGYTNYNEKFKS (SEQ ID NO: 10), and FINPDSGYTNYNEKFKT (SEQ ID NO: 11).

CDRH3

In some embodiments, the third heavy chain CDR (CDRH3) of an anti-TLR7 agent provided herein comprises an amino acid sequence that is at least 80 percent identical (e.g., 85, 87, 90, 91, 92, 93, 94, 95, 96, 97, 98, 99, or 100 percent identical) to the amino acid sequence $X_1X_2X_3X_4X_5X_6X_7X_8X_9X_{10}X_{11}X_{12}X_{13}X_{14}FX_{15}X_{16}$ (SEQ ID NO:32), where $X_1$ is D, E, H, or G; $X_2$ is L, G, or P; $X_3$ is T, G, or Y; $X_4$ is no amino acid, T, D, or G; $X_5$ is no amino acid, L or G; $X_6$ is no amino acid or Y; $X_7$ is V, Y, or S; $X_8$ is V, S, P, or G; $X_9$ is D or N; $X_{10}$ is G, Y, or W; $X_{11}$ is no amino acid or N; $X_{12}$ is no amino acid or Y; $X_{13}$ is no amino acid or V; $X_{14}$ is no amino acid, R or Y; $X_{15}$ is A or D; and $X_{16}$ is Y or F. In some embodiments, the third heavy chain CDR (CDRH3) of an anti-TLR7 agent provided herein comprises an amino acid sequence that is at least 90 percent identical to the amino acid sequence of SEQ ID NO:32. In some embodiments, the CDRH3 comprises an amino acid sequence that is at least 95 percent identical to the amino acid sequence of SEQ ID NO:32. In some embodiments, the CDRH3 comprises an amino acid sequence that is 100 percent identical to the amino acid sequence of SEQ ID NO:32.

The amino acid $X_1$ of SEQ ID NO:32 may be substituted with any amino acid. In some embodiments, the amino acid $X_1$ of SEQ ID NO:32 is substituted with a conservative amino acid (e.g., conservative to D, E, H, and/or G). In some embodiments, the amino acid $X_1$ of SEQ ID NO:32 is substituted with an acidic amino acid. In some embodiments, the amino acid $X_1$ of SEQ ID NO:32 is substituted with a basic amino acid. In some embodiments, the amino acid $X_1$ of SEQ ID NO:32 is substituted with an amino acid residue that influences chain orientation.

The amino acid $X_2$ of SEQ ID NO:32 may be substituted with any amino acid. In some embodiments, the amino acid $X_2$ of SEQ ID NO:32 is substituted with a conservative amino acid (e.g., conservative to L, G, and/or P). In some embodiments, the amino acid $X_2$ of SEQ ID NO:32 is substituted with a hydrophobic amino acid. In some embodiments, the amino acid $X_2$ of SEQ ID NO: 32 is substituted with an amino acid residue that influences chain orientation.

The amino acid $X_3$ of SEQ ID NO:32 may be substituted with any amino acid. In some embodiments, the amino acid $X_3$ of SEQ ID NO:32 is substituted with a conservative amino acid (e.g., conservative to T, G, and/or Y). In some embodiments, the amino acid $X_3$ of SEQ ID NO:32 is substituted with a neutral hydrophilic amino acid. In some embodiments, the amino acid $X_3$ of SEQ ID NO:32 is substituted with an amino acid that influences chain orientation. In some embodiments, the amino acid $X_3$ of SEQ ID NO:32 is substituted with an aromatic amino acid.

The amino acid $X_4$ of SEQ ID NO:32 may be substituted with any amino acid. In some embodiments, the amino acid $X_4$ of SEQ ID NO:32 is substituted with a conservative amino acid (e.g., conservative to T, D, and/or G). In some embodiments, the amino acid $X_4$ of SEQ ID NO:32 is substituted with a neutral hydrophilic amino acid. In some embodiments, the amino acid $X_4$ of SEQ ID NO:32 is substituted with an acidic amino acid. In some embodiments, the amino acid $X_4$ of SEQ ID NO:32 is substituted with an amino acid residue that influences chain orientation.

The amino acid $X_5$ of SEQ ID NO:32 may be substituted with any amino acid. In some embodiments, the amino acid $X_5$ of SEQ ID NO:32 is substituted with a conservative amino acid (e.g., conservative to L and/or G). In some embodiments, the amino acid $X_5$ of SEQ ID NO:32 is substituted with a hydrophobic amino acid. In some embodiments, the amino acid $X_5$ of SEQ ID NO:32 is substituted with an amino acid residue that influences chain orientation.

The amino acid $X_6$ of SEQ ID NO:32 may be substituted with any amino acid. In some embodiments, the amino acid $X_6$ of SEQ ID NO:32 is substituted with a conservative amino acid (e.g., conservative to Y). In some embodiments, the amino acid $X_6$ of SEQ ID NO:32 is substituted with an aromatic amino acid.

The amino acid $X_7$ of SEQ ID NO:32 may be substituted with any amino acid. In some embodiments, the amino acid $X_7$ of SEQ ID NO:32 is substituted with a conservative amino acid (e.g., conservative to V, Y, and/or S). In some embodiments, the amino acid $X_7$ of SEQ ID NO:32 is substituted with a hydrophobic amino acid. In some embodiments, the amino acid $X_7$ of SEQ ID NO:32 is substituted with an aromatic amino acid. In some embodiments, the amino acid $X_7$ of SEQ ID NO:32 is substituted with a neutral hydrophilic amino acid.

The amino acid $X_8$ of SEQ ID NO:32 may be substituted with any amino acid. In some embodiments, the amino acid $X_8$ of SEQ ID NO:32 is substituted with a conservative amino acid (e.g., conservative to V, S, P, and/or G). In some embodiments, the amino acid $X_8$ of SEQ ID NO:32 is substituted with a hydrophobic amino acid. In some embodiments, the amino acid $X_8$ of SEQ ID NO:32 is substituted with a neutral hydrophilic amino acid. In some embodiments, the amino acid $X_8$ of SEQ ID NO:32 is substituted with an amino acid residue that influences chain orientation.

The amino acid $X_9$ of SEQ ID NO:32 may be substituted with any amino acid. In some embodiments, the amino acid $X_9$ of SEQ ID NO:32 is substituted with a conservative amino acid (e.g., conservative to D and/or N). In some embodiments, the amino acid $X_9$ of SEQ ID NO:32 is substituted with an acidic amino acid. In some embodiments, the amino acid $X_9$ of SEQ ID NO:32 is substituted with a basic amino acid.

The amino acid $X_{10}$ of SEQ ID NO:32 may be substituted with any amino acid. In some embodiments, the amino acid $X_{10}$ of SEQ ID NO:32 is substituted with a conservative amino acid (e.g., conservative to G, Y, and/or W). In some embodiments, the amino acid $X_{10}$ of SEQ ID NO:32 is substituted with an amino acid residue that influences chain orientation. In some embodiments, the amino acid $X_{10}$ of SEQ ID NO:32 is substituted with an aromatic amino acid.

The amino acid $X_{11}$ of SEQ ID NO:32 may be substituted with any amino acid. In some embodiments, the amino acid $X_{11}$ of SEQ ID NO:32 is substituted with a conservative amino acid (e.g., conservative to N). In some embodiments, the amino acid $X_{11}$ of SEQ ID NO:32 is substituted with a basic amino acid.

The amino acid $X_{12}$ of SEQ ID NO:32 may be substituted with any amino acid. In some embodiments, the amino acid $X_{12}$ of SEQ ID NO:32 is substituted with a conservative amino acid (e.g., conservative to Y). In some embodiments, the amino acid $X_{12}$ of SEQ ID NO:32 is substituted with an aromatic amino acid.

The amino acid $X_{13}$ of SEQ ID NO:32 may be substituted with any amino acid. In some embodiments, the amino acid $X_{13}$ of SEQ ID NO:32 is substituted with a conservative amino acid (e.g., conservative to V). In some embodiments, the amino acid $X_{13}$ of SEQ ID NO:32 is substituted with a hydrophobic amino acid.

The amino acid $X_{14}$ of SEQ ID NO:32 may be substituted with any amino acid. In some embodiments, the amino acid $X_{14}$ of SEQ ID NO:32 is substituted with a conservative amino acid (e.g., conservative to R and/or Y). In some embodiments, the amino acid $X_{14}$ of SEQ ID NO:32 is substituted with a basic amino acid. In some embodiments, the amino acid $X_{14}$ of SEQ ID NO:32 is substituted with an aromatic amino acid.

The amino acid $X_{15}$ of SEQ ID NO:32 may be substituted with any amino acid. In some embodiments, the amino acid $X_{15}$ of SEQ ID NO:32 is substituted with a conservative amino acid (e.g., conservative to A and/or D). In some embodiments, the amino acid $X_{15}$ of SEQ ID NO:32 is substituted with a hydrophobic amino acid. In some embodiments, the amino acid $X_{15}$ of SEQ ID NO:32 is substituted with an acidic amino acid.

The amino acid $X_{16}$ of SEQ ID NO:32 may be substituted with any amino acid. In some embodiments, the amino acid $X_{16}$ of SEQ ID NO:32 is substituted with a conservative amino acid (e.g., conservative to Y and/or F). In some embodiments, the amino acid $X_{16}$ of SEQ ID NO:32 is substituted with an aromatic amino acid.

In some embodiments, the CDRH3 of anti-TLR7 agents provided herein comprises an amino acid sequence chosen from DLTTVVDGFAY (SEQ ID NO:12), EGGD-LYYSNYNYVRFAY (SEQ ID NO:13), HGGYPNWYFDF (SEQ ID NO:14), and GPYGGYSGDGFDY (SEQ ID NO:15).

CDRL1

In some embodiments, the first light chain CDR (CDRL1) of an anti-TLR7 agent provided herein comprises an amino acid sequence that is at least 80 percent identical (e.g., 85, 87, 90, 91, 92, 93, 94, 95, 96, 97, 98, 99, or 100 percent identical) to the amino acid sequence $X_1X_2SX_3X_4X_5X_6X_7X_8X_9X_{10}$ (SEQ ID NO:33), where $X_1$ is R or L, $X_2$ is A or P; $X_3$ is E or Q; $X_4$ is D or S; $X_5$ is I or L; $X_6$ is Y or S; $X_7$ is N or T; $X_8$ is V, E, N, or S; $X_9$ is L or I; and $X_{10}$ is A or H. In some embodiments, the CDRL1 comprises an amino acid sequence that is at least 90 percent identical to the amino acid sequence of SEQ ID NO:33. In some embodiments, the CDRL1 comprises an amino acid sequence that is at least 95 percent identical to the amino acid sequence of SEQ ID NO:33. In some embodiments, the CDRL1 comprises an amino acid sequence that is 100 percent identical to the amino acid sequence of SEQ ID NO:33.

The amino acid $X_1$ of SEQ ID NO:33 may be substituted with any amino acid. In some embodiments, the amino acid $X_1$ of SEQ ID NO:33 is substituted with a conservative amino acid (e.g., conservative to R and/or L). In some embodiments, the amino acid $X_1$ of SEQ ID NO:33 is substituted with a basic amino acid. In some embodiments, the amino acid $X_1$ of SEQ ID NO:33 is substituted with a hydrophobic amino acid.

The amino acid $X_2$ of SEQ ID NO:33 may be substituted with any amino acid. In some embodiments, the amino acid $X_2$ of SEQ ID NO:33 may be substituted with a conservative amino acid (e.g., conservative to A and/or P). In some embodiments, the amino acid $X_2$ of SEQ ID NO:33 is substituted with a hydrophobic amino acid. In some embodiments, the amino acid $X_2$ of SEQ ID NO:33 is substituted with an amino acid that influences chain orientation.

The amino acid $X_3$ of SEQ ID NO:33 may be substituted with any amino acid. In some embodiments, the amino acid $X_3$ of SEQ ID NO:33 may be substituted with a conservative amino acid (e.g., conservative to E and/or Q). In some embodiments, the amino acid $X_3$ of SEQ ID NO:33 is substituted with an acidic amino acid. In some embodiments, the amino acid $X_3$ of SEQ ID NO:33 is substituted with a basic amino acid.

The amino acid $X_4$ of SEQ ID NO:33 may be substituted with any amino acid. In some embodiments, the amino acid $X_4$ of SEQ ID NO:33 may be substituted with a conservative amino acid (e.g., conservative to D and/or S). In some embodiments, the amino acid $X_4$ of SEQ ID NO:33 is substituted with an acidic amino acid. In some embodiments, the amino acid $X_4$ of SEQ ID NO:33 is substituted with a neutral hydrophilic amino acid.

The amino acid $X_5$ of SEQ ID NO:33 may be substituted with any amino acid. In some embodiments, the amino acid $X_5$ of SEQ ID NO:33 may be substituted with a conservative amino acid (e.g., conservative to I and/or L). In some embodiments, the amino acid $X_5$ of SEQ ID NO:33 is substituted with a hydrophobic amino acid.

The amino acid $X_6$ of SEQ ID NO:33 may be substituted with any amino acid. In some embodiments, the amino acid $X_6$ of SEQ ID NO:33 may be substituted with a conservative amino acid (e.g., conservative to Y and/or S). In some embodiments, the amino acid $X_6$ of SEQ ID NO:33 is substituted with an aromatic amino acid. In some embodiments, the amino acid $X_6$ of SEQ ID NO:33 is substituted with a neutral hydrophilic amino acid.

The amino acid $X_7$ of SEQ ID NO:33 may be substituted with any amino acid. In some embodiments, the amino acid $X_7$ of SEQ ID NO:33 may be substituted with a conservative amino acid (e.g., conservative to N and/or T). In some embodiments, the amino acid $X_7$ of SEQ ID NO:33 is substituted with a basic amino acid. In some embodiments, the amino acid $X_7$ of SEQ ID NO:33 is substituted with a neutral hydrophilic amino acid.

The amino acid $X_8$ of SEQ ID NO:33 may be substituted with any amino acid. In some embodiments, the amino acid $X_8$ of SEQ ID NO:33 may be substituted with a conservative amino acid (e.g., conservative to V, E, N, and/or S). In some embodiments, the amino acid $X_8$ of SEQ ID NO:33 is substituted with a hydrophobic amino acid. In some embodiments, the amino acid $X_8$ of SEQ ID NO:33 is substituted with an acidic amino acid. In some embodiments, the amino acid $X_8$ of SEQ ID NO:33 is substituted with a basic amino acid. In some embodiments, the amino acid $X_8$ of SEQ ID NO:33 is substituted with a neutral hydrophilic amino acid.

The amino acid $X_9$ of SEQ ID NO:33 may be substituted with any amino acid. In some embodiments, the amino acid $X_9$ of SEQ ID NO:33 may be substituted with a conservative amino acid (e.g., conservative to L and/or I). In some embodiments, the amino acid $X_9$ of SEQ ID NO:33 is substituted with a hydrophobic amino acid.

The amino acid $X_{10}$ of SEQ ID NO:33 may be substituted with any amino acid. In some embodiments, the amino acid $X_{10}$ of SEQ ID NO:33 may be substituted with a conservative amino acid (e.g., conservative to A and/or H). In some embodiments, the amino acid $X_{10}$ of SEQ ID NO:33 is substituted with a hydrophobic amino acid. In some embodiments, the amino acid $X_{10}$ of SEQ ID NO:33 is substituted with a basic amino acid.

In some embodiments, the CDRL1 of an anti-TLR7 agent provided herein comprises an amino acid sequence chosen from RASEDIYNVLA (SEQ ID NO:16), RASEDIYNELA (SEQ ID NO:17), LPSEDIYNNLA (SEQ ID NO:18), and RASQSLSTSIH (SEQ ID NO:19).

CDRL2

In some embodiments, the second light chain CDR (CDRL2) of an anti-TLR7 agent provided herein comprises an amino acid sequence that is at least 80 percent identical (e.g., 85, 87, 90, 91, 92, 93, 94, 95, 96, 97, 98, 99, or 100 percent identical) to the amino acid sequence $X_1AX_2X_3X_4X_5X_6$ (SEQ ID NO:34), where $X_1$ is N or Y, $X_2$ is N or S, $X_3$ is R, N, S, or Q, $X_4$ is L or P, $X_5$ is H, Q, or I, and $X_6$ is N, T, D, or S. In some embodiments, the CDRL2 comprises an amino acid sequence that is at least 90 percent identical to the amino acid sequence of SEQ ID NO:34. In some embodiments, the CDRL2 comprises an amino acid sequence that is at least 95 percent identical to the amino acid sequence of SEQ ID NO:34. In some embodiments, the CDRL2 comprises an amino acid sequence that is 100 percent identical to the amino acid sequence of SEQ ID NO:34.

The amino acid $X_1$ of SEQ ID NO:34 may be substituted with any amino acid. In some embodiments, the amino acid $X_1$ of SEQ ID NO:34 is substituted with a conservative amino acid (e.g., conservative to N and/or Y). In some embodiments, the amino acid $X_1$ of SEQ ID NO:34 is substituted with a basic amino acid. In some embodiments, the amino acid $X_1$ of SEQ ID NO:34 is substituted with an aromatic amino acid.

The amino acid $X_2$ of SEQ ID NO:34 may be substituted with any amino acid. In some embodiments, the amino acid $X_2$ of SEQ ID NO:34 is substituted with a conservative amino acid (e.g., conservative to N and/or S). In some embodiments, the amino acid $X_2$ of SEQ ID NO:34 is substituted with a basic amino acid. In some embodiments, the amino acid $X_2$ of SEQ ID NO:34 is substituted with a neutral hydrophilic amino acid.

The amino acid $X_3$ of SEQ ID NO:34 may be substituted with any amino acid. In some embodiments, the amino acid $X_3$ of SEQ ID NO:34 is substituted with a conservative amino acid (e.g., conservative to R, N, S, and/or Q). In some embodiments, the amino acid $X_3$ of SEQ ID NO:34 is substituted with a basic amino acid. In some embodiments, the amino acid $X_3$ of SEQ ID NO:34 is substituted with a neutral hydrophilic amino acid. In some embodiments, the amino acid $X_3$ of SEQ ID NO:34 is substituted with a basic amino acid.

The amino acid $X_4$ of SEQ ID NO:34 may be substituted with any amino acid. In some embodiments, the amino acid $X_4$ of SEQ ID NO:34 is substituted with a conservative amino acid (e.g., conservative to L and/or P). In some embodiments, the amino acid $X_4$ of SEQ ID NO:34 is substituted with a hydrophobic amino acid. In some embodiments, the amino acid $X_4$ of SEQ ID NO:34 is substituted with an amino acid that influences chain orientation.

The amino acid $X_5$ of SEQ ID NO:34 may be substituted with any amino acid. In some embodiments, the amino acid $X_5$ of SEQ ID NO:34 is substituted with a conservative amino acid (e.g., conservative to H, Q, and/or I). In some embodiments, the amino acid $X_5$ of SEQ ID NO:34 is substituted with a basic amino acid. In some embodiments, the amino acid $X_5$ of SEQ ID NO:34 is substituted with a hydrophobic amino acid.

The amino acid $X_6$ of SEQ ID NO:34 may be substituted with any amino acid. In some embodiments, the amino acid $X_6$ of SEQ ID NO:34 is substituted with a conservative amino acid (e.g., conservative to N, T, D, and/or S). In some embodiments, the amino acid $X_6$ of SEQ ID NO:34 is substituted with a basic amino acid. In some embodiments, the amino acid $X_6$ of SEQ ID NO:34 is substituted with a neutral hydrophilic amino acid. In some embodiments, the amino acid $X_6$ of SEQ ID NO:34 is substituted with an acidic amino acid.

In some embodiments, the CDRL2 of an anti-TLR7 agent provided herein comprises an amino acid sequence chosen from NANRLHN (SEQ ID NO:20), NANNLHT (SEQ ID NO:21), NANSLHT (SEQ ID NO:22), YASNLQD (SEQ ID NO:23), and YASQPIS (SEQ ID NO:24).
CDRL3

In some embodiments, the third light chain CDR (CDRL3) of an anti-TLR7 agent provided herein comprises an amino acid sequence that is at least 80 percent identical (e.g., 85, 87, 90, 91, 92, 93, 94, 95, 96, 97, 98, 99, or 100 percent identical) to the amino acid sequence $X_1QX_2X_3X_4X_5PX_6T$ (SEQ ID NO:35), where $X_1$ is Q or L; $X_2$ is Y, D, or S; $X_3$ is Y or S; $X_4$ is D or S; $X_5$ is Y or S; and $X_6$ is N, H, W, F, or Y. In some embodiments, the CDRL3 comprises an amino acid sequence that is at least 90 percent identical to the amino acid sequence of SEQ ID NO:35. In some embodiments, the CDRL3 comprises an amino acid sequence that is at least 95 percent identical to the amino acid sequence of SEQ ID NO:35. In some embodiments, the CDRL3 comprises an amino acid sequence that is 100 percent identical to the amino acid sequence of SEQ ID NO:35.

The amino acid $X_1$ of SEQ ID NO:35 may be substituted with any amino acid. In some embodiments, the amino acid $X_1$ of SEQ ID NO:35 is substituted with a conservative amino acid (e.g., conservative to Q and/or L). In some embodiments, the amino acid $X_1$ of SEQ ID NO:35 is substituted with a basic amino acid. In some embodiments, the amino acid $X_1$ of SEQ ID NO:35 is substituted with a hydrophobic amino acid.

The amino acid $X_2$ of SEQ ID NO:35 may be substituted with any amino acid. In some embodiments, the amino acid $X_2$ of SEQ ID NO:35 is substituted with a conservative amino acid (e.g., conservative to Y, D or S). In some embodiments, the amino acid $X_2$ of SEQ ID NO:35 is substituted with an aromatic amino acid. In some embodiments, the amino acid $X_2$ of SEQ ID NO:35 is substituted with an acidic amino acid. In some embodiments, the amino acid $X_2$ of SEQ ID NO:35 is substituted with a neutral hydrophilic amino acid.

The amino acid $X_3$ of SEQ ID NO:35 may be substituted with any amino acid. In some embodiments, the amino acid $X_3$ of SEQ ID NO:35 is substituted with a conservative amino acid (e.g., conservative to Y and/or S). In some embodiments, the amino acid $X_3$ of SEQ ID NO:35 is substituted with an aromatic amino acid. In some embodiments, the amino acid $X_3$ of SEQ ID NO:35 is substituted with a neutral hydrophilic amino acid.

The amino acid $X_4$ of SEQ ID NO:35 may be substituted with any amino acid. In some embodiments, the amino acid $X_4$ of SEQ ID NO:35 is substituted with a conservative amino acid (e.g., conservative to D and/or S). In some embodiments, the amino acid $X_4$ of SEQ ID NO:35 is substituted with an acidic amino acid. In some embodiments, the amino acid $X_4$ of SEQ ID NO:35 is substituted with a neutral hydrophilic amino acid.

The amino acid $X_5$ of SEQ ID NO:35 may be substituted with any amino acid. In some embodiments, the amino acid $X_5$ of SEQ ID NO:35 is substituted with a conservative amino acid (e.g., conservative to Y and/or S). In some embodiments, the amino acid $X_5$ of SEQ ID NO:35 is substituted with an aromatic amino acid. In some embodiments, the amino acid $X_5$ of SEQ ID NO:35 is substituted with a neutral hydrophilic amino acid.

The amino acid $X_6$ of SEQ ID NO:35 may be substituted with any amino acid. In some embodiments, the amino acid $X_6$ of SEQ ID NO:35 is substituted with a conservative amino acid (e.g., conservative to N, H, W, F and/or Y). In some embodiments, the amino acid $X_6$ of SEQ ID NO:35 is substituted with a basic amino acid. In some embodiments, the amino acid $X_6$ of SEQ ID NO:35 is substituted with an aromatic amino acid.

In some embodiments, the CDRL3 of an anti-TLR7 agent provided herein comprises an amino acid sequence chosen from QQYYDYPNT (SEQ ID NO:25), QQYYDYPHT (SEQ ID NO:26), QQYYDYPWT (SEQ ID NO:27), LQDSDYPFT (SEQ ID NO:28), and QQSYSSPYT (SEQ ID NO:29).
CDR Sets In some embodiments, an anti-TLR7 agent comprises an immunoglobulin heavy chain variable domain comprising a set of CDRs (i.e., CDRH1, CDRH2, CDRH3); and an immunoglobulin light chain variable domain comprising a set of CDRs (i.e., CDRL1, CDRL2, CDRL3). In some embodiments, an anti-TLR7 agent herein comprises two immunoglobulin heavy chain variable domains each comprising a set of CDRs (i.e., CDRH1, CDRH2, CDRH3); and two immunoglobulin light chain variable domains each comprising a set of CDRs (i.e., CDRL1, CDRL2, CDRL3). Sets of CDRs may comprise any combination of CDR amino acid sequences (i.e., CDRH1, CDRH2, CDRH3; and CDRL1, CDRL2, CDRL3) provided herein. In some embodiments, an immunoglobulin heavy chain variable domain comprises a set of CDRH1, CDRH2, and CDRH3 amino acid sequences, and an immunoglobulin light chain variable domain comprises a set of CDRL1, CDRL2 and CDRL3 amino acid sequences chosen from sets 1-6 provided in the table below. For an anti-TLR7 agent comprising two immunoglobulin heavy chain variable domains and two immunoglobulin light chain variable domains, each immunoglobulin heavy chain variable domain may comprise a set of CDRH1, CDRH2, and CDRH3 amino acid sequences, and each immunoglobulin light chain variable domain may comprise a set of CDRL1, CDRL2 and CDRL3 amino acid sequences chosen from sets 1-6 provided in the following Table.

TABLE 2

| | | | CDR sets | | | |
| --- | --- | --- | --- | --- | --- | --- |
| set | CDRH1 (SEQ ID NO:) | CDRH2 (SEQ ID NO:) | CDRH3 (SEQ ID NO:) | CDRL1 (SEQ ID NO:) | CDRL2 (SEQ ID NO:) | CDRL3 (SEQ ID NO:) |
| 1 | DYWMS (1) | DIKYDGSFI DYAPSLKN (6) | DLTTVVDG-FAY (12) | RASQSLST SIH (19) | YASQPIS (24) | QQSYSSPY T (29) |
| 2 | DYWMS (1) | DIKYDGTFI DYAPSLKN (7) | DLTTVVDG-FAY (12) | RASQSLST SIH (19) | YASQPIS (24) | QQSYSSPY T (29) |
| 3 | NYYMA (2) | SITNSGRTT YYRDSVKG (8) | EGGDLYYS NYNYVRFA Y (13) | LPSEDIYNN LA (18) | YASNLQD (23) | LQDSDYPE T (28) |
| 4 | DYYMA (3) | SISYEGSST HYGDSVKA (9) | HGGYPNWY FDF (14) | RASEDIYNE LA (17) | NANSLHT (22) | QQYYDYPW T (27) |
| 5 | DYCVH (4) | YINPYSGYT NYNEKFKS (10) | GPYGGYSG DGFDY (15) | RASEDIYNV LA (16) | NANRLHN (20) | QQYYDYPN T (25) |
| 6 | DYYIH (5) | FINPDSGYT NYNEKFKT (11) | GPYGGYSG DGFDY (15) | RASEDIYNV LA (16) | NANNLHT (21) | QQYYDYPH T (26) |

In some embodiments, all CDRs are from the same set. For example, for an anti-TLR7 agent comprising two immunoglobulin heavy chain variable domains and two immunoglobulin light chain variable domains, each immunoglobulin heavy chain variable domain may comprise a set of CDRH1, CDRH2, and CDRH3 amino acid sequences from set 1, and each immunoglobulin light chain variable domain may comprise a set of CDRL1, CDRL2 and CDRL3 amino acid sequences from set 1.

In some embodiments, CDRs are from the different sets. For example, for an anti-TLR7 agent comprising two immunoglobulin heavy chain variable domains and two immunoglobulin light chain variable domains, each immunoglobulin heavy chain variable domain may comprise a set of CDRH1, CDRH2, and CDRH3 amino acid sequences from set 1, and each immunoglobulin light chain variable domain may comprise a set of CDRL1, CDRL2 and CDRL3 amino acid sequences from set 2. In another example, for an anti-TLR7 agent comprising two immunoglobulin heavy chain variable domains and two immunoglobulin light chain variable domains, one immunoglobulin heavy chain variable domain may comprise a set of CDRH1, CDRH2, and CDRH3 amino acid sequences from set 1 and the other immunoglobulin heavy chain variable domain may comprise a set of CDRH1, CDRH2, and CDRH3 amino acid sequences from set 2; and one immunoglobulin light chain variable domain may comprise a set of CDRL1, CDRL2 and CDRL3 amino acid sequences from set 1 and the other immunoglobulin light chain variable domain may comprise a set of CDRL1, CDRL2 and CDRL3 amino acid sequences from set 2.

VH

An anti-TLR7 agent provided herein may comprise a heavy chain variable domain (VH). In some embodiments, a heavy chain variable domain (VH) of an anti-TLR7 agent provided herein comprises a polypeptide that is at least 80 percent identical (e.g., 85, 87, 90, 91, 92, 93, 94, 95, 96, 97, 98, 99, or 100 percent identical) to the amino acid sequence ELQLVESGGGLVKP-GASLKLSCVASGFTFSDYWMSWVRQTPGKT-MEWIGDIKYDGSFIDY APSLKNRFTISRDNAKNT-LYLQMSNVRSEDTATYYCARDLTTVVDGFAYWGQGT LVTVSS (SEQ ID NO: 36), e.g., 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more, identical to the amino acid sequence of SEQ ID NO: 36. In some embodiments, a VH comprises a polypeptide that is at least 90 percent identical to the amino acid sequence of SEQ ID NO: 36. In some embodiments, a VH comprises a polypeptide that is at least 95 percent identical to the amino acid sequence of SEQ ID NO: 36. In some embodiments, a VH comprises a polypeptide that is 100 percent identical to the amino acid sequence of SEQ ID NO: 36.

An anti-TLR7 agent provided herein may comprise a heavy chain variable domain (VH). In some embodiments, a heavy chain variable domain (VH) of an anti-TLR7 agent provided herein comprises a polypeptide that is at least 80 percent identical (e.g., 85, 87, 90, 91, 92, 93, 94, 95, 96, 97, 98, 99, or 100 percent identical) to the amino acid sequence ELQLVESGGGLVKP-GASLKLSCVASGFTFSDYWMSWVRQTPGKT-MEWIGDIKYDGTFIDY APSLKNRFTISRDNAKNT-LYLQMSNVRSEDTATYYCARDLTTVVDGFAYWGHGT LVTVSS (SEQ ID NO: 37), e.g., 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more, identical to the amino acid sequence of SEQ ID NO: 37. In some embodiments, a VH comprises a polypeptide that is at least 90 percent identical to the amino acid sequence of SEQ ID NO: 37. In some embodiments, a VH comprises a polypeptide that is at least 95 percent identical to the amino acid sequence of SEQ ID NO: 37. In some embodiments, a VH comprises a polypeptide that is 100 percent identical to the amino acid sequence of SEQ ID NO: 37.

An anti-TLR7 agent provided herein may comprise a heavy chain variable domain (VH). In some embodiments, a heavy chain variable domain (VH) of an anti-TLR7 agent provided herein comprises a polypeptide that is at least 80 percent identical (e.g., 85, 87, 90, 91, 92, 93, 94, 95, 96, 97, 98, 99, or 100 percent identical) to the amino acid sequence EVQLVESGGGLLQPGRSLKLSCAASGFTFTNYYMAWVRQAPTKGLEWVASITNSGRTTYYRDSVKGRFTISRDNAKSTLYLQMDSLRSEDTATYYCTREGGDLYYSNYNYVRFAYWGQGT LVTVSS (SEQ ID NO: 38), e.g., 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more, identical to the amino acid sequence of SEQ ID NO: 38. In some embodiments, a VH comprises a polypeptide that is at least 90 percent identical to the amino acid sequence of SEQ ID NO: 38. In some embodiments, a VH comprises a polypeptide that is at least 95 percent identical to the amino acid sequence of SEQ ID NO: 38. In some embodiments, a VH comprises a polypeptide that is 100 percent identical to the amino acid sequence of SEQ ID NO: 38.

An anti-TLR7 agent provided herein may comprise a heavy chain variable domain (VH). In some embodiments, a heavy chain variable domain (VH) of an anti-TLR7 agent provided herein comprises a polypeptide that is at least 80 percent identical (e.g., 85, 87, 90, 91, 92, 93, 94, 95, 96, 97, 98, 99, or 100 percent identical) to the amino acid sequence EVQLVESGGGLVQPGRSLKLSCAASGFTFRDYYMAWVRQAPKKGLEWVASISYEGSSTHYGDSVKARFTVSRDDAKSTLYLQMNSLRSEDTATYYCGRHGGYPNWYFDFWGPGT MVTVSS (SEQ ID NO: 39), e.g., 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more, identical to the amino acid sequence of SEQ ID NO: 39. In some embodiments, a VH comprises a polypeptide that is at least 90 percent identical to the amino acid sequence of SEQ ID NO: 39. In some embodiments, a VH comprises a polypeptide that is at least 95 percent identical to the amino acid sequence of SEQ ID NO: 39. In some embodiments, a VH comprises a polypeptide that is 100 percent identical to the amino acid sequence of SEQ ID NO: 39.

An anti-TLR7 agent provided herein may comprise a heavy chain variable domain (VH). In some embodiments, a heavy chain variable domain (VH) of an anti-TLR7 agent provided herein comprises a polypeptide that is at least 80 percent identical (e.g., 85, 87, 90, 91, 92, 93, 94, 95, 96, 97, 98, 99, or 100 percent identical) to the amino acid sequence QVNLLQSGAALVKPGASVKLSCKASGYTFTDYCVHWVKQSHGKSLEWIGYINPYSGYTNY NEKFKSKATLTVDTSTNTAYMELSRLTSDDSATCYCTRGPYGGYSGDGFDYWGQGV MVTVSS (SEQ ID NO: 40), e.g., 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more, identical to the amino acid sequence of SEQ ID NO: 40. In some embodiments, a VH comprises a polypeptide that is at least 90 percent identical to the amino acid sequence of SEQ ID NO: 40. In some embodiments, a VH comprises a polypeptide that is at least 95 percent identical to the amino acid sequence of SEQ ID NO: 40. In some embodiments, a VH comprises a polypeptide that is 100 percent identical to the amino acid sequence of SEQ ID NO: 40.

An anti-TLR7 agent provided herein may comprise a heavy chain variable domain (VH). In some embodiments, a heavy chain variable domain (VH) of an anti-TLR7 agent provided herein comprises a polypeptide that is at least 80 percent identical (e.g., 85, 87, 90, 91, 92, 93, 94, 95, 96, 97, 98, 99, or 100 percent identical) to the amino acid sequence QVNLLQSGAALVKPGASVKLSCKASGYTFTDYYIHWVKQSHVKSLEWFGFINPDSGYTNY NEKFKTKATLTVDKSTNTAYMELSRLTSEGSATYYCTRGPYGGYSGDGFDYWGQGV MVTVSS (SEQ ID NO: 41), e.g., 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more, identical to the amino acid sequence of SEQ ID NO: 41. In some embodiments, a VH comprises a polypeptide that is at least 90 percent identical to the amino acid sequence of SEQ ID NO: 41. In some embodiments, a VH comprises a polypeptide that is at least 95 percent identical to the amino acid sequence of SEQ ID NO: 41. In some embodiments, a VH comprises a polypeptide that is 100 percent identical to the amino acid sequence of SEQ ID NO: 41.

In some embodiments, a VH of an anti-TLR7 agent provided herein comprises a polypeptide chosen from SEQ ID NO: 36, SEQ ID NO: 37, SEQ ID NO: 38, SEQ ID NO: 39, SEQ ID NO: 40, and SEQ ID NO: 41.

VL

An anti-TLR7 agent provided herein may comprise a light chain variable domain (VL). In some embodiments, a light chain variable domain (VL) of an anti-TLR7 agent provided herein comprises a polypeptide that is at least 80 percent identical (e.g., 85, 87, 90, 91, 92, 93, 94, 95, 96, 97, 98, 99, or 100 percent identical) to the amino acid sequence

```
                                 (SEQ ID NO: 42)
NIVLTQSPATLSVTPGESVSLSCRASQSLSTSIHWYQQKPNESPRLLIRY

ASQPISGIPSRFSGSGSGTDFTLSINRVESEDFSIYYCQQSYSSPYTFGA

GTKLELK,
``` e.g., 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more, identical to the amino acid sequence of SEQ ID NO: 42. In some embodiments, a VL comprises a polypeptide that is at least 90 percent identical to the amino acid sequence of SEQ ID NO: 42. In some embodiments, a VL comprises a polypeptide that is at least 95 percent identical to the amino acid sequence of SEQ ID NO: 42. In some embodiments, a VL comprises a polypeptide that is 100 percent identical to the amino acid sequence of SEQ ID NO: 42.

An anti-TLR7 agent provided herein may comprise a light chain variable domain (VL). In some embodiments, a light chain variable domain (VL) of an anti-TLR7 agent provided herein comprises a polypeptide that is at least 80 percent identical (e.g., 85, 87, 90, 91, 92, 93, 94, 95, 96, 97, 98, 99, or 100 percent identical) to the amino acid sequence

```
                                    (SEQ ID NO: 43)
NIVLTQSPATLSVTPGESVSLSCRASQSLSTSIHWYQQMPNESPRLLIRY

ASQPISGIPSRFSGSGSGTDFTLSINRVESEDFSIYYCQQSYSSPYTFGA

GTRLELK,
``` e.g., 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more, identical to the amino acid sequence of SEQ ID NO: 43. In some embodiments, a VL comprises a polypeptide that is at least 90 percent identical to the amino acid sequence of SEQ ID NO: 43. In some embodiments, a VL comprises a polypeptide that is at least 95 percent identical to the amino acid sequence of SEQ ID NO: 43. In some embodiments, a VL comprises a polypeptide that is 100 percent identical to the amino acid sequence of SEQ ID NO: 43.

An anti-TLR7 agent provided herein may comprise a light chain variable domain (VL). In some embodiments, a light chain variable domain (VL) of an anti-TLR7 agent provided herein comprises a polypeptide that is at least 80 percent identical (e.g., 85, 87, 90, 91, 92, 93, 94, 95, 96, 97, 98, 99, or 100 percent identical) to the amino acid sequence DIQMTQSPASLSASLGETVSIECLPSEDIYNN-LAWYQQKPGKSPQLLIHYASNLQDGVPS RFSGSGSGTQYS-LKIKSLESEDAATYFCLQDSDYPFTFGSGTKLEIK (SEQ ID NO: 44), e.g., 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more, identical to the amino acid sequence of SEQ ID NO: 44. In some embodiments, a VL comprises a polypeptide that is at least 90 percent identical to the amino acid sequence of SEQ ID NO: 44. In some embodiments, a VL comprises a polypeptide that is at least 95 percent identical to the amino acid sequence of SEQ ID NO: 44. In some embodiments, a VL comprises a polypeptide that is 100 percent identical to the amino acid sequence of SEQ ID NO: 44.

An anti-TLR7 agent provided herein may comprise a light chain variable domain (VL). In some embodiments, a light chain variable domain (VL) of an anti-TLR7 agent provided herein comprises a polypeptide that is at least 80 percent identical (e.g., 85, 87, 90, 91, 92, 93, 94, 95, 96, 97, 98, 99, or 100 percent identical) to the amino acid sequence

```
                                    (SEQ ID NO: 45)
DIQMTQSPASLSASLGETVTIECRASEDIYNELAWYQQKPGKSPQLLIYN

ANSLHTGVPSRFSGSGSGTQYSLKINSLQSEDVASYFCQQYYDYPWTFGG

GTKLELK,
``` e.g., 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more, identical to the amino acid sequence of SEQ ID NO: 45. In some embodiments, a VL comprises a polypeptide that is at least 90 percent identical to the amino acid sequence of SEQ ID NO: 45. In some embodiments, a VL comprises a polypeptide that is at least 95 percent identical to the amino acid sequence of SEQ ID NO: 45. In some embodiments, a VL comprises a polypeptide that is 100 percent identical to the amino acid sequence of SEQ ID NO: 45.

An anti-TLR7 agent provided herein may comprise a light chain variable domain (VL). In some embodiments, a light chain variable domain (VL) of an anti-TLR7 agent provided herein comprises a polypeptide that is at least 80 percent identical (e.g., 85, 87, 90, 91, 92, 93, 94, 95, 96, 97, 98, 99, or 100 percent identical) to the amino acid sequence

```
                                    (SEQ ID NO: 46)
DIQMTQSPASLSASLGETVTIECRASEDIYNVLAWYQQKPGKSPQLLISN

ANRLHNGVPSRFSGSGSGTQYSLKINSLQSEDVASYFCQQYYDYPNTFGA

GTKLELK,
``` e.g., 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more, identical to the amino acid sequence of SEQ ID NO: 46. In some embodiments, a VL comprises a polypeptide that is at least 90 percent identical to the amino acid sequence of SEQ ID NO: 46. In some embodiments, a VL comprises a polypeptide that is at least 95 percent identical to the amino acid sequence of SEQ ID NO: 46. In some embodiments, a VL comprises a polypeptide that is 100 percent identical to the amino acid sequence of SEQ ID NO: 46.

An anti-TLR7 agent provided herein may comprise a light chain variable domain (VL). In some embodiments, a light chain variable domain (VL) of an anti-TLR7 agent provided herein comprises a polypeptide that is at least 80 percent identical (e.g., 85, 87, 90, 91, 92, 93, 94, 95, 96, 97, 98, 99, or 100 percent identical) to the amino acid sequence

```
                                    (SEQ ID NO: 47)
DIQMTQSPASLSASLGETVTIECRASEDIYNVLAWYQQKPGKSPQLLISN

ANNLHTGVPSRFSGSESGTQYSLKINSLQSEDVASYFCQQYYDYPHTFGA

GTKLELK,
``` e.g., 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more, identical to the amino acid sequence of SEQ ID NO: 47. In some embodiments, a VL comprises a polypeptide that is at least 90 percent identical to the amino acid sequence of SEQ ID NO: 47. In some embodiments, a VL comprises a polypeptide that is at least 95 percent identical to the amino acid sequence of SEQ ID NO: 47. In some embodiments, a VL comprises a polypeptide that is 100 percent identical to the amino acid sequence of SEQ ID NO: 47.

In some embodiments, a VL of an anti-TLR7 agent provided herein comprises a polypeptide chosen from SEQ ID NO: 42, SEQ ID NO: 43, SEQ ID NO: 44, SEQ ID NO: 45, SEQ ID NO: 46, and SEQ ID NO: 47.

Fc

An anti-TLR7 agent provided herein may comprise a fragment crystallizable region (Fc region). An Fc region typically forms the tail of an antibody and can interact with certain cell surface receptors and certain components of the complement system. An Fc region may include, for example, two polypeptides, each derived from the second (CH2) and third (CH3) constant domains of an antibody heavy chain.

The amino acid sequence of a wild-type CH2-CH3 portion of an Fc region is provided below (positioning is as in the EU index as in Kabat et al. (1992) SEQUENCES OF PROTEINS OF IMMUNOLOGICAL INTEREST, National Institutes of Health Publication No. 91-3242) (SEQ ID NO:51).

```
CH2→
APELLGGPS VFLFPPKPKD TLMISRTPEV TCWVDVSHE DPEVKFNWYV DGVEVHNAKT
231       240        250        260       270        280

←CH2|CH3→
KPREEQYNST YRVVSVLTVL HQDWLNGKEY KCKVSNKALP APIEKTISKA K  GQPREPQVY
290        300        310        320        330        340

TLPPSREEMT KNQVSLTCLV KGFYPSDIAV EWESNGQPEN NYKTTPPVLD SDGSFFLYSK
350        360        370        380        390        400

←CH3|
LTVDKSRWQQ GNVFSCSVMH EALHNHYTQK SLSLSPGK
410        420        430        440
```

In some embodiments, an Fc region includes one or more modifications (e.g., one or more amino acid substitutions, insertions, or deletions relative to a comparable wild-type Fc region). Agents comprising modified Fc regions (variant agents) typically have altered phenotypes relative to agents comprising wild-type Fc regions. A variant agent phenotype may be expressed as altered serum half-life, altered stability, altered susceptibility to cellular enzymes, or altered effector function (e.g., as assayed in an NK dependent or macrophage dependent assay). Fc region modifications that alter effector function may include modifications that increase binding to activating receptors (e.g., FcγRIIA (CD16A) and reduce binding to inhibitory receptors (e.g., FcγRIIB (CD32B) (see, e.g., Stavenhagen, J. B. et al. (2007) Cancer Res. 57(18):8882-8890)). Examples of variants of human IgG1 Fc regions with reduced binding to CD32B and/or increased binding to CD16A contain F243L, R292P, Y300L, V305I and/or P396L substitutions. Amino acid positions correspond to the amino acid numbering of the CH2-CH3 domain provided above.

In some embodiments, an Fc region includes one or more modifications that reduce or abrogate binding of the Fc to Fc receptors. Such modifications may include amino acid substitutions at positions 234, 235, 265 and 297 (see e.g., U.S. Pat. No. 5,624,821, which is incorporated by reference herein). Example substitutions include one or more of L234A, L235A, D265A and N297Q. Amino acid positions correspond to the amino acid numbering of the CH2-CH3 domain provided above.

In some embodiments, an Fc region includes one or more modifications that alter (relative to a wild-type Fc region) the Ratio of Affinities of the modified Fc region to an activating FcγR (such as FcγRIIA or FcγRIIIA) relative to an inhibiting FcγR (such as FcγRIIB):

$$\text{Ratio of Affinities} = \frac{\text{Wild-Type to Variant Change in Affinity to } FcyR_{Activating}}{\text{Wild-Type to Variant Change in Affinity to } FcyR_{inhibiting}}$$

Where a modified Fc region has a Ratio of Affinities greater than 1, an anti-TLR7 agent herein may have particular use in providing a therapeutic or prophylactic treatment of a disease, disorder, or infection, or the amelioration of a symptom thereof, where an enhanced efficacy of effector cell function (e.g., ADCC) mediated by FcγR is desired, e.g., cancer or infectious disease. Where a modified Fc region has a Ratio of Affinities less than 1, an anti-TLR7 agent herein may have particular use in providing a therapeutic or prophylactic treatment of a disease or disorder, or the amelioration of a symptom thereof, where a decreased efficacy of effector cell function mediated by FcγR is desired, e.g., autoimmune or inflammatory disorders. Table 3 lists example single, double, triple, quadruple and quintuple amino acid substitutions having a Ratio of Affinities greater than 1 or less than 1 (see e.g., PCT Publication Nos. WO 04/063351; WO 06/088494; WO 07/024249; WO 06/113665; WO 07/021841; WO 07/106707; WO 2008/140603, each of which is incorporated by reference herein). Amino acid positions correspond to the amino acid numbering of the CH2-CH3 domain provided above.

TABLE 3

| | | Example Single and Multiple Substitutions Listed by Ratio of Affinities | | | |
|---|---|---|---|---|---|
| Ratio | Single | Double | Triple | Quadruple | Quintuple |
| >1 | F243L | F243L & R292P | F243L, P247L & N421K | L234F, F243L, R292P & Y300L | L235V, F243L, R292P, Y300L & P396L |
| | D270E | F243L & Y300L | F243L, R292P & Y300L | L235I, F243L, R292P & Y300L | L235P, F243L, R292P, Y300L & P396L |
| | R292G | F243L & P396L | F243L, R292P & V305I | L235Q, F243L, R292P & Y300L | F243L, R292P, V305I, Y300L & P396L |
| | R292P | D270E & P396L | F243L, R292P & P396L | F243L, P247L, D270E & N421K | |
| | | R292P & Y300L | F243L, Y300L & P396L | F243L, R255L, D270E & P396L | |
| | | R292P & V305I | P247L, D270E & N421K | F243L, D270E, G316D & R416G | |

TABLE 3-continued

Example Single and Multiple Substitutions Listed by Ratio of Affinities

| Ratio | Single | Double | Triple | Quadruple | Quintuple |
|---|---|---|---|---|---|
| | | R292P & P396L | R255L, D270E & P396L | F243L, D270E, K392T & P396L | |
| | | Y300L & P396L | D270E, G316D & R416G | F243L, D270E, P396L & Q419H | |
| | | P396L & Q419H | D270E, K392T & P396L | F243L, R292P, Y300L, & P396L | |
| | | | D270E, P396L & Q419H | F243L, R292P, V305I & P396L | |
| | | | V284M, R292L & K370N | P247L, D270E, Y300L & N421K | |
| | | | R292P, Y300L & P396L | R255L, D270E, R292G & P396L | |
| | | | | R255L, D270E, Y300L & P396L | |
| | | | | D270E, G316D, P396L & R416G | |
| <1 | Y300L P396L | F243L & P396L | F243L, R292P & V305I | | |
| | | P247L & N421K | | | |
| | | R255L & P396L | | | |
| | | R292P & V305I | | | |
| | | K392T & P396L | | | |
| | | P396L & Q419H | | | |

In particular embodiments, an antibody of the disclosure can comprise: (1) a heavy chain variable region having a CDRH1, a CDRH2, and a CDRH3 of SEQ ID NOS: 4, 10, and 15, respectively, and at least 90% (e.g., 90%, 91%, 92%, 93%, 94%, 95%, 96%, 97%, 98%, 99%, or 100%) identity to the sequence of SEQ ID NO:40, and (2) a light chain variable region having a CDRL1, a CDRL2, and a CDRL3 of SEQ ID NOS:19, 24, and 29, respectively, and at least 90% (e.g., 90%, 91%, 92%, 93%, 94%, 95%, 96%, 97%, 98%, 99%, or 100%) identity to the sequence of SEQ ID NO:46. Such an antibody can be an IgG1, IgG2, IgG3, or IgG4.

In certain embodiments, the antibody comprises a heavy chain having a heavy chain variable region having the sequence of SEQ ID NO:40 and at least 90% (e.g., 90%, 91%, 92%, 93%, 94%, 95%, 96%, 97%, 98%, 99%, or 100%) identity to the sequence of SEQ ID NO:55:
QVNLLQSGAALVKPGASVKLSCK-ASGYTFTDYCVHWVKQSHGKSLEWIGY-INPYSGYTNY NEKFKSKATLTVDTSTN-TAYMELSRLTSDDSATCYCTRGPYGGYSGDG-FDYWGQGV MVTVSSASTKGPSVFPLAPSSKST-SGGTAALGCLVKDYFPEPVTVSWNSGALT-SGVHTFPA VLQSSGGLYSLSS-WTVPSSSLGTQTYICNVNHKPSNTKVDKR-VEPKSCDKTHTCPPCPAPE LLGGPSVFLFPPKPKDTLMISRTPE-VTCVVVDVSHEDPE-VKFNWYVDGVEVHNAKTKPREE QYN-STYRVVSVLTVLHQDWLNGKEYKCKVSNK-ALPAPIEKTISKAKGQPREPQVYTLPPSR EEMT-KNQVSLTCLVKGFYPSDIAVEWESNGQPEN-NYKTTPPVLDSDGSFFLYSKLTVDKSR WQQGNVFSCSVMHEALHNHYTQKSLSLSPGK, and a light chain having a light chain variable region having the sequence of SEQ ID NO:46 and at least 90%

(e.g., 90%, 91%, 92%, 93%, 94%, 95%, 96%, 97%, 98%, 99%, or 100%) identity to the sequence of SEQ ID NO:52:

DIQMTQSPASLSASLGETVTIECRASEDIYNVLAWYQQKPGKSPQLLISN

ANRLHNGVPSRFSGSGSGTQYSLKINSLQSEDVASYFCQQYYDYPNTFGA

GTKLELKRTVAAPSVFIFPPSDEQLKSGTASWCLLNNFYPREAKVQWKVD

NALQSGNSQESVTEQDSKDSTYSLSSTLTLSKADYEKHKVYACEVTHQGL

SSPVTKSFNRGEC.

In particular embodiments, an antibody of the disclosure can comprise: (1) a heavy chain variable region having a CDRH1, a CDRH2, and a CDRH3 of SEQ ID NOS:5, 11, and 15, respectively, and at least 90% (e.g., 90%, 91%, 92%, 93%, 94%, 95%, 96%, 97%, 98%, 99%, or 100%) identity to the sequence of SEQ ID NO:41, and (2) a light chain variable region having a CDRL1, a CDRL2, and a CDRL3 of SEQ ID NOS:19, 24, and 29, respectively, and at least 90% (e.g., 90%, 91%, 92%, 93%, 94%, 95%, 96%, 97%, 98%, 99%, or 100%) identity to the sequence of SEQ ID NO:47. Such an antibody can be an IgG1, IgG2, IgG3, or IgG4.

In certain embodiments, the antibody comprises a heavy chain having a heavy chain variable region having the sequence of SEQ ID NO:41 and at least 90% (e.g., 90%, 91%, 92%, 93%, 94%, 95%, 96%, 97%, 98%, 99%, or 100%) identity to the sequence of SEQ ID NO:53:
QVNLLQSGAALVKPGASVKLSCK-ASGYTFTDYYIHWVKQSHVKSLEWFG-FINPDSGYTNYN EKFKTKATLTVDKSTN-TAYMELSRLTSEGSATYYCTRGPYGGYSG-DGFDYWGQGV MVTVSSASTKGPSVF-PLAPSSKSTSGGTAALGCLVKDYF-PEPVTVSWNSGALTSGVHTFPA VLQSSGGLYS- LSSWTVPSSSLGTQTYICNVNHKPSNTKVDKRVE-
PKSCDKTHTCPPCPAPE
LLGGPSVFLFPPKPKDTLMISRTPE-
VTCVVVDVSHEDPE-
VKFNWYVDGVEVHNAKTKPREE QYN-
STYRWSVLTVLHQDWLNGKEYKCKVSNKALPA-
PIEKTISKAKGQPREPQVYTLPPSR
EEMTKNQVSLTCLVKGFYPSDIAVEWESNGQ-
PENNYKTTPPVLDSDGSFFLYSKLTVDKSR
WQQGNVFSCSVMHEALHNHYTQKSLSLSPGK,
and a light chain having a light chain variable region
having the sequence of SEQ ID NO:47 and at least 90%
(e.g., 90%, 91%, 92%, 93%, 94%, 95%, 96%, 97%,
98%, 99%, or 100%) identity to the sequence of SEQ
ID NO:54:

DIQMTQSPASLSASLGETVTIECRASEDIYNVLAWYQQKPGKSPQLLI

SNANNLHTGVPSRFSGSESGTQYSLKINSLQSEDVASYFCQQYYDYPH

TFGAGTKLELKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC.

Agents that Competitively Bind with an Anti-TLR7 Agent

Provided herein are anti-TLR7 agents that competitively
bind, or are capable of competitively binding, with one or
more anti-TLR7 agents described herein. In particular, pro-
vided herein are anti-TLR7 agents that compete, or are
capable of competing, with one or more anti-TLR7 agents
described herein for binding to TLR7. Such agents that
compete, or are capable of competing, with anti-TLR7
agents described herein may be referred to as competitor
agents. In certain instances, an agent (i.e., competitor agent)
may be considered to compete for binding to TLR7 when the
competitor binds to the same general region of TLR7 as an
anti-TLR7 agent described herein (i.e., extracellular region
or leucine-rich binding domain). In certain instances, an
agent (i.e., competitor agent) may be considered to compete
for binding to TLR7 when the competitor binds to the exact
same region of TLR7 as an anti-TLR7 agent described
herein (e.g., exact same peptide (linear epitope) or exact
same surface amino acids (conformational epitope)). In
certain instances, an agent (i.e., competitor agent) may be
considered capable of competing for binding to TLR7 when
the competitor binds to the same general region of TLR7 as
an anti-TLR7 agent described herein (i.e., extracellular
region or leucine-rich binding domain) under suitable assay
conditions. In certain instances, an agent (i.e., competitor
agent) may be considered capable of competing for binding
to TLR7 when the competitor binds to the exact same region
of TLR7 as an anti-TLR7 agent described herein (e.g., exact
same peptide (linear epitope) or exact same surface amino
acids (conformational epitope)) under suitable assay condi-
tions.

In certain instances, an agent (i.e., competitor agent) may
be considered to compete for binding to TLR7 when the
competitor blocks the binding of one or more anti-TLR7
agents described herein to TLR7. In certain instances, an
agent (i.e., competitor agent) may be considered capable of
competing for binding to TLR7 when the competitor blocks
the binding of one or more anti-TLR7 agents described
herein to TLR7 under suitable assay conditions. Whether a
competitor blocks the binding of one or more anti-TLR7
agents described herein to TLR7 may be determined using
a suitable competition assay or blocking assay, such as, for example, a blocking assay as described in Example 6 herein.
A competitor agent may block binding of one or more
anti-TLR7 agents described herein to TLR7 in a competition
or blocking assay by 50% or more, and conversely, one or
more anti-TLR7 agents described herein may block binding
of the competitor agent to TLR7 in a competition or block-
ing assay by about 50% or more. For example, an agent (i.e.,
competitor agent) may block binding of one or more anti-
TLR7 agents described herein to TLR7 in a competition or
blocking assay by about 55%, 60%, 65%, 70%, 75%, 80%,
85%, 90%, 95%, or 100%, and conversely, one or more
anti-TLR7 agents described herein may block binding of the
competitor agent to TLR7 in a competition or blocking assay
by about 55%, 60%, 65%, 70%, 75%, 80%, 85%, 90%, 95%,
or 100%.

In certain instances, an agent (i.e., competitor agent) may
be considered to compete for binding to TLR7 when the
competitor binds to TLR7 with a similar affinity as one or
more anti-TLR7 agents described herein. In certain
instances, an agent (i.e., competitor agent) may be consid-
ered capable of competing for binding to TLR7 when the
competitor binds to TLR7 with a similar affinity as one or
more anti-TLR7 agents described herein under suitable
assay conditions. In some embodiments, an agent (i.e.,
competitor agent) is considered to compete for binding to
TLR7 when the competitor binds to TLR7 with an affinity
that is at least about 50% of the affinity of one or more
anti-TLR7 agents described herein. For example, an agent
(i.e., competitor agent) may be considered to compete for
binding to TLR7 when the competitor binds to TLR7 with
an affinity that is at least about 55%, 60%, 65%, 70%, 75%,
80%, 85%, 90%, 95%, or 100% of the affinity of one or more
anti-TLR7 agents described herein. A competitor agent may
comprise any feature described herein for anti-TLR7 agents.

Also provided herein are anti-TLR7 agents that bind to, or
are capable of binding to, the same epitope as one or more
anti-TLR7 agents described herein. In particular, provided
herein are anti-TLR7 agents that compete with one or more
anti-TLR7 agents described herein for binding to the same
epitope on TLR7. Such agents that bind the same epitope
may be referred to as epitope competitors. In certain
instances, an epitope competitor may bind to the exact same
region of TLR7 as an anti-TLR7 agent described herein
(e.g., exact same peptide (linear epitope) or exact same
surface amino acids (conformational epitope)). In certain
instances, epitope competitor blocks the binding of one or
more anti-TLR7 agents described herein to TLR7. An
epitope competitor may block binding of one or more
anti-TLR7 agents described herein to TLR7 in a competition
assay by about 50% or more, and conversely, one or more
anti-TLR7 agents described herein may block binding of the
epitope competitor to TLR7 in a competition assay by 50%
or more. In certain instances, an epitope competitor binds to
TLR7 with a similar affinity as one or more anti-TLR7
agents described herein. In some embodiments, an epitope
competitor binds to TLR7 with an affinity that is at least
about 50% of the affinity of one or more anti-TLR7 agents
described herein. For example, an epitope competitor may
bind to TLR7 with an affinity that is at least about 55%, 60%,
65%, 70%, 75%, 80%, 85%, 90%, 95%, or 100% of the
affinity of one or more anti-TLR7 agents described herein.
An epitope competitor may comprise any feature described
herein for anti-TLR7 agents.

Antibody Preparation

In some embodiments, an anti-TLR7 agent is an antibody.
Methods for generating anti-TLR7 antibodies and variants
of anti-TLR7 antibodies are described in the Examples below. In some embodiments, an anti-TLR7 agent is a humanized antibody, or an antigen binding fragment thereof. In some embodiments, an anti-TLR7 agent is a humanized antibody, or a derivative thereof that binds TLR7. Humanized anti-TLR7 antibodies may be prepared based on a nonhuman anti-TLR7 antibody. Fully human antibodies may also be prepared, e.g., in a genetically engineered (i.e., transgenic) mouse (e.g., from Medarex) that, when presented with an immunogen, can produce a human antibody that does not necessarily require CDR grafting. These antibodies are fully human (100% human protein sequences) from animals such as mice in which the non-human antibody genes are suppressed and replaced with human antibody gene expression. Antibodies may be generated against TLR7 when presented to these genetically engineered mice or other animals that can to produce human frameworks for the relevant CDRs.

Where a variant is generated, the parent antibody is prepared. Example techniques for generating such nonhuman antibody and parent antibodies are described in the following sections.

Antigen Preparation

The antigen for production of antibodies may be, e.g., intact TLR7, particularly expressed in cells, or a portion of TLR7 (e.g. N-terminal domain, C-terminal domain, a cytoplasmic domain, an intra-organelle domain, a transmembrane domain, an extracellular domain, an ectodomain, a TIR domain, a leucine-rich domain, or a TLR7 fragment comprising a desired epitope). Other forms of antigens useful for generating antibodies will be apparent to those skilled in the art.

Polyclonal Antibodies

Polyclonal antibodies may be raised in animals (vertebrate or invertebrates, including mammals, birds and fish, including cartilaginous fish) by multiple subcutaneous (sc) or intraperitoneal (ip) injections of a relevant antigen and an adjuvant. It may be useful to conjugate the relevant antigen to a protein or other carrier that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl$_2$, or R$^1$N═C═NR, where R and R$^1$ are different alkyl groups. Non-protein carriers (e.g., colloidal gold) also may be used for antibody production.

Animals are immunized against the antigen, immunogenic conjugates, or derivatives by combining, e.g., 100 µg or 5 µg of the protein or conjugate (for rabbits or mice, respectively) with three volumes of Freund's complete adjuvant and injecting the solution intradermally at multiple sites. One month later the animals are boosted with one-fifth to one-tenth of the original amount of peptide or conjugate in Freund's complete adjuvant by subcutaneous injection at multiple sites. Seven to 14 days later the animals are bled and the serum is assayed for antibody titer. Animals are boosted until the titer plateaus. Often, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies

Monoclonal antibodies may be made using the hybridoma method first described by Kohler et al., Nature, 256:495 (1975), or may be made by other methods such as recombinant DNA methods (U.S. Pat. No. 4,816,567). In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (coding, Monoclonal Antibodies: Principles and Practice, pp. 59-103 (Academic Press, 1986)).

The hybridoma cells thus prepared are seeded and grown in a suitable culture medium that may contain one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. The binding specificity of monoclonal antibodies produced by hybridoma cells may be determined by immunoprecipitation, by an in vitro binding assay, such as radioimmunoassay (RIA) or enzyme-linked immunoabsorbant assay (ELISA), or by flow cytometric analysis of cells expressing the membrane antigen. The binding affinity of the monoclonal antibody can, for example, be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (coding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). Alternatively, cDNA may be prepared from mRNA and the cDNA then subjected to DNA sequencing. The hybridoma cells serve as a preferred source of such genomic DNA or RNA for cDNA preparation. Once isolated, the DNA may be placed into expression vectors, which are well known in the art, and which are then transfected into host cells such as *E coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

Humanization and Amino Acid Sequence Variants

General methods for humanization of antibodies are described, for example, in U.S. Pat. Nos. 5,861,155, 6,479,284, 6,407,213, 6,639,055, 6,500,931, 5,530,101, 5,585,089, 5,693,761, 5,693,762, 6,180,370, 5,714,350, 6,350,861, 5,777,085, 5,834,597, 5,882,644, 5,932,448, 6,013,256, 6,129,914, 6,210,671, 6,329,511, 5,225,539, 6,548,640, and 5,624,821, each of which is incorporated by reference herein. In certain embodiments, it may be desirable to generate amino acid sequence variants of these humanized antibodies, particularly where these improve the binding affinity or other biological properties of the antibody.

Amino acid sequence variants of the anti-TLR7 antibody are prepared by introducing appropriate nucleotide changes into the anti-TLR7 antibody DNA, or by peptide synthesis. Such variants include, for example, deletions from, and/or insertions into and/or substitutions of, residues within the amino acid sequences of the anti-TLR7 antibodies of the examples herein. Any combination of deletion, insertion, and substitution is made to arrive at the final construct, provided that the final construct possesses the desired characteristics. The amino acid changes also may alter post-translational processes of the humanized or variant anti-TLR7 antibody, such as changing the number or position of glycosylation sites.

One method for identification of certain residues or regions of the anti-TLR7 antibody that are preferred locations for mutagenesis is called "alanine scanning mutagenesis," as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with TLR7 antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed anti-TLR7 antibody variants are screened for the desired activity. Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an N-terminal methionyl residue or the antibody fused to an epitope tag. Other insertional variants include the fusion of an enzyme or a polypeptide that increases the serum half-life of the antibody to the N- or C-terminus of the antibody.

Another type of variant is an amino acid substitution variant. These variants have at least one amino acid residue removed from the antibody molecule and a different residue inserted in its place. The sites of greatest interest for substitutional mutagenesis include the hypervariable regions, but FR alterations are also contemplated. Conservative substitutions are preferred, but more substantial changes may be introduced and the products may be screened. Examples of substitutions are listed below:

Example Amino Acid Residue Substitutions

Ala (A) val; leu; ile; val
Arg (R) lys; gln; asn; lys
Asn (N) gln; his; asp, lys; gln; arg
Asp (D) glu; asn
Cys (C) ser; ala
Gln (Q) asn; glu
Glu (E) asp; gln
Gly (G) ala
His (H) asn; gln; lys; arg
Ile (I) leu; val; met; ala; leu; phe; norleucine
Leu (L) norleucine; ile; val; ile; met; ala; phe
Lys (K) arg; gln; asn
Met (M) leu; phe; ile
Phe (F) leu; val; ile; ala; tyr
Pro (P) ala
Ser (S) thr
Thr (T) ser
Trp (W) tyr; phe
Tyr (Y) trp; phe; thr; ser
Val (V) ile; leu; met; phe; ala; norleucine Substantial modifications in the biological properties of an antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the antibody also may be substituted, to improve the oxidative stability of the molecule and prevent aberrant crosslinking. Conversely, cysteine bond(s) may be added to the antibody to improve its stability (particularly where the antibody is an antibody fragment such as an Fv fragment).

One type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine-scanning mutagenesis can be performed to identify hypervariable region residues contributing significantly to antigen binding. Alternatively, or in addition, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically either N-linked and/or or O-linked. N-linked refers to the attachment of the carbohydrate moiety to the side chain of an asparagine residue. The tripeptide sequences asparagine-X-serine and asparagine-X-threonine, where X is any amino acid except proline, are the most common recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of anti-TLR7 antibodies herein are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of an anti-TLR7 antibody.

Human Antibodies

As an alternative to humanization, human antibodies can be generated. For example, transgenic animals (e.g., mice) may be generated that are capable, upon immunization, of producing a full repertoire of human antibodies in the absence of endogenous immunoglobulin production. For example, a homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice can result in the production of human antibodies upon antigen challenge (see, e.g., Jakobovits et al., Proc. Natl. Acad. Sci. USA, 90:2551 (1993); Jakobovits et al., Nature, 362:255-258(1993); Bruggermann et al., Year in Immuno., 7:33 (1993); and U.S. Pat. Nos. 5,591,669, 5,589,369 and 5,545,807). Human antibodies also can be derived from phage-display libraries (Hoogenboom et al., J. Mol. Biol., 227:381 (1991); Marks et al., J. Mol. Biol., 222:581-597 (1991); and U.S. Pat. Nos. 5,565,332 and 5,573,905). Human antibodies also may be generated by in vitro activated B cells (see U.S. Pat. Nos. 5,567,610 and 5,229,275).

Antigen-Binding Antibody Fragments

In certain embodiments, an anti-TLR7 agent is an antibody fragment that retains at least one desired activity, including antigen binding. Various techniques have been developed for the production of antibody fragments. In some instances, these fragments are derived via proteolytic digestion of intact antibodies (see, e.g., Morimoto et al., Journal of Biochemical and Biophysical Methods 24:107-117(1992) and Brennan et al., Science 229:81 (1985)). In some instances, these fragments are produced directly by recombinant host cells. For example, Fab'-SH fragments can be directly recovered from E. coli and chemically coupled to form F(ab')$_2$ fragments (Carter et al., Bio/Technology 10:163-167 (1992)). In some instances, the F(ab')$_2$ is formed using the leucine zipper GCN4 to promote assembly of the F(ab')$_2$ molecule. According to another approach, Fv, Fab or F(ab')$_2$ fragments can be isolated directly from recombinant host cell culture. Other techniques for the production of antibody fragments will be apparent to the skilled practitioner.

Multispecific Antibodies and Other Agents

In some embodiments, an anti-TLR7 agent comprises a first binding moiety and a second binding moiety, where the first binding moiety is specifically reactive with a first molecule that is TLR7 and the second binding moiety is specifically reactive with a second molecule that is a molecular species different from the first molecule. Such agents may comprise a plurality of first binding moieties, a plurality of second binding moieties, or a plurality of first binding moieties and a plurality of second binding moieties. Preferably, the ratio of first binding moieties to second binding moieties is about 1:1, although it may range from about 1000:1 to about 1:1000, where the ratio may be measured in terms of valency.

In those embodiments where the first moiety is an antibody, the second binding moiety may also be an antibody. In some embodiments, the first and second moieties are linked via a linker moiety, which may have two to many 100's or even thousands of valencies for attachment of first and second binding moieties by one or different chemistries. Examples of bispecific antibodies include those that are reactive against two different epitopes; in some instances, one epitope is a TLR7 epitope and the second epitope is on an unrelated soluble molecule. In some embodiments, the bispecific antibody is reactive against an epitope on TLR7 and against an epitope on a different molecule found on the surface of the same cell. In some embodiments, the bispecific antibody is reactive against an epitope on TLR7 and against an epitope on a different molecule found on the surface of a different cell.

Compositions herein may also comprise a first agent and a second agent, where the first agent comprises a first binding moiety specifically reactive with a first molecule (e.g., TLR7) and the second agent comprises a second binding moiety specifically reactive with a second molecule that is a molecular species different than the first molecule. The first and/or second agent may be an antibody. The ratio of first agent to second agent may range from about 1,000:1 to 1:1,000, although the preferred ratio is about 1:1. In some embodiments, it may be desirable to generate multispecific (e.g. bispecific) anti-TLR7 antibodies having binding specificities for at least two different epitopes. Certain bispecific antibodies may bind to two different epitopes of TLR7. Bispecific antibodies can be prepared as full-length antibodies or antibody fragments (e.g., F(ab')$_2$ bispecific antibodies).

According to one for making bispecific antibodies, the interface between a pair of antibody molecules can be engineered to maximize the percentage of heterodimers that are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers (see e.g., WO96/27011 published Sep. 6, 1996).

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques.

Any suitable technique may be used for generating bispecific antibodies from antibody fragments. For example, bispecific antibodies can be prepared using chemical linkage. In certain methods, intact antibodies are proteolytically cleaved to generate F(ab')₂ fragments (see e.g., Brennan et al., Science 229:81 (1985), which is incorporated by reference herein). These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. In yet a further embodiment, Fab'-SH fragments directly recovered from E. coli can be chemically coupled in vitro to form bispecific antibodies (see e.g., Shalaby et al., J. Exp. Med. 175:217-225 (1992), which is incorporated by reference herein).

Any suitable technique for making and isolating bispecific antibody fragments directly from recombinant cell culture may be used. For example, bispecific antibodies have been produced using leucine zippers (see e.g., Kostelny et al., J. Immunol. 148(5):1547-1553 (1992), which is incorporated by reference herein). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (scFv) dimers (see e.g., Gruber et al., J. Immunol. 152:5368 (1994), which is incorporated by reference herein). In certain instances, a bispecific antibody may be a "linear antibody" produced as described in Zapata et al. Protein Eng. 8(10):1057-1062 (1995), which is incorporated by reference herein.

Antibodies with two valencies or more are contemplated herein. An antibody (or polymer or polypeptide) herein comprising one or more binding sites per arm or fragment thereof will be referred to herein as "multivalent" antibody. For example a "bivalent" antibody herein comprises two binding sites per Fab or fragment thereof whereas a "trivalent" polypeptide herein comprises three binding sites per Fab or fragment thereof. In a multivalent polymer herein, the two or more binding sites per Fab may be binding to the same or different antigens. For example, the two or more binding sites in a multivalent polypeptide herein may be directed against the same antigen, for example against the same parts or epitopes of said antigen or against two or more same or different parts or epitopes of said antigen; and/or may be directed against different antigens; or a combination thereof. Thus, a bivalent polypeptide herein, for example, may comprise two identical binding sites, may comprise a first binding sites directed against a first part or epitope of an antigen and a second binding site directed against the same part or epitope of said antigen or against another part or epitope of said antigen; or may comprise a first binding sites directed against a first part or epitope of an antigen and a second binding site directed against a different antigen. However, as will be clear from the description hereinabove, the technology herein is not limited thereto, in the sense that a multivalent polypeptide herein may comprise any number of binding sites directed against the same or different antigens. In one embodiment the multivalent polypeptide comprises at least two ligand binding elements, one of which contains one or more CDR peptide sequences shown herein. In another embodiment the multivalent polypeptide comprises three ligand binding sites, each independently selected from the CDR sequences disclosed herein.

In certain embodiments, at least one of the ligand binding elements binds TLR7. In one embodiment, at least one of the ligand binding elements binds another target. In one embodiment, there are up to 10,000 binding elements in a multivalent binding molecule, and the ligand binding elements may be linked to a scaffold.

An antibody (or polymer or polypeptide) herein that contains at least two binding sites per Fab or fragment thereof, in which at least one binding site is directed against a first antigen and a second binding site directed against a second antigen different from the first antigen, may also be referred to as "multispecific." Thus, a "bispecific" polymer comprises at least one site directed against a first antigen and at least one second site directed against a second antigen, whereas a "trispecific" is a polymer that comprises at least one binding site directed against a first antigen, at least one further binding site directed against a second antigen, and at least one further binding site directed against a third antigen; and the like. Accordingly, in their simplest form, a bispecific polypeptide herein is a bivalent polypeptide (per Fab) of the technology provided herein. However, as will be clear from the description hereinabove, the technology herein is not limited thereto, in the sense that a multispecific polypeptide herein may comprise any number of binding sites directed against two or more different antigens.

Other Modifications

Other modifications of an anti-TLR7 agent are contemplated. For example, technology herein also pertains to immunoconjugates comprising an antibody described herein (e.g., an anti-TLR7 antibody) conjugated to a cytotoxic agent such as a toxin (e.g., an enzymatically active toxin of bacterial, fungal, plant or animal origin, or fragments thereof), or a radioactive isotope (for example, a radioconjugate), or a cytotoxic drug. Such conjugates are sometimes referred to as "agent-drug conjugates" or "ADC". Conjugates are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Anti-TLR7 agents (e.g., anti-TLR7 antibodies) disclosed herein may be formulated as immunoliposomes. Liposomes containing an antibody are prepared by methods known in the art, such as described in Epstein et al., Proc. Natl. Acad. Sci. USA 82:3688 (1985); Hwang et al., Proc. Natl Acad. Sci. USA 77:4030 (1980); and U.S. Pat. Nos. 4,485,045 and 4,544,545. Liposomes with enhanced circulation time are disclosed in U.S. Pat. No. 5,013,556. For example, liposomes can be generated by the reverse phase evaporation method with a lipid composition comprising phosphatidyl choline, cholesterol and PEG-derivatized phosphatidylethanolamine (PEG-PE). Liposomes are extruded through filters of defined pore size to yield liposomes with the desired diameter. Fab' fragments of an antibody provided herein can be conjugated to the liposomes as described in Martin et al., J. Biol. Chem. 257:286-288 (1982) via a disulfide interchange reaction. Another active ingredient is optionally contained within the liposome.

Enzymes or other polypeptides can be covalently bound to an anti-TLR7 agent (e.g., anti-TLR7 antibody) by techniques well known in the art such as the use of the heterobifunctional cross-linking reagents discussed above. In some embodiments, fusion proteins comprising at least the antigen binding region of an antibody provided herein linked to at least a functionally active portion of an enzyme can be constructed using recombinant DNA techniques well known in the art (see, e.g., Neuberger et al., Nature 312:604-608 (1984)).

In certain embodiments, it may be desirable to use an antibody fragment, rather than an intact antibody, to increase penetration of target tissues and cells, for example. In such instances, it may be desirable to modify the antibody fragment in order to increase its serum half-life. This may be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis; see, e.g., WO96/32478 published Oct. 17, 1996).

Covalent modifications of an anti-TLR7 agent (e.g., anti-TLR7 antibody) are also included within the scope of this technology. For example, modifications may be made by chemical synthesis or by enzymatic or chemical cleavage of an anti-TLR7 antibody. Other types of covalent modifications of an antibody are introduced into the molecule by reacting targeted amino acid residues of the antibody with an organic derivatizing agent that is capable of reacting with selected side chains or the N- or C-terminal residues. Example covalent modifications of polypeptides are described in U.S. Pat. No. 5,534,615, specifically incorporated herein by reference. A preferred type of covalent modification of the antibody comprises linking the antibody to one of a variety of non-proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.
Nucleic Acids, Vectors, Host Cells, and Recombinant Methods Technology described herein also provides isolated nucleic acids encoding an anti-TLR7 agent (e.g., anti-TLR7 antibody), vectors and host cells comprising the nucleic acid, and recombinant techniques for the production of the agent or antibody. A nucleic acid herein may include one or more subsequences, each referred to as a polynucleotide.

Provided herein are nucleic acids (e.g., isolated nucleic acids) comprising a nucleotide sequence that encodes an anti-TLR7 agent or antibody, or fragment thereof. In some embodiments, a nucleic acid encodes an immunoglobulin heavy chain variable domain of an anti-TLR7 agent provided herein. In some embodiments, a nucleic acid encodes an immunoglobulin light chain variable domain of an anti-TLR7 agent provided herein. In some embodiments, a nucleic acid encodes an immunoglobulin heavy chain variable domain and an immunoglobulin light chain variable domain of an anti-TLR7 agent provided herein. In some embodiments, a nucleic acid comprises a nucleotide sequence that encodes an amino acid sequence of any one of SEQ ID NOS:1-29 and 36-47. For example, a nucleic acid may comprise a nucleotide sequence that encodes a CDR amino acid sequence of any one of SEQ ID NOS:1-29 and 36-47. A nucleic acid may comprise a nucleotide sequence that encodes an immunoglobulin heavy chain variable domain amino acid sequence of any one of SEQ ID NOS: 36-41. A nucleic acid may comprise a nucleotide sequence that encodes an immunoglobulin light chain variable domain amino acid sequence of any one of SEQ ID NOS:42-47.

For recombinant production of an anti-TLR7 agent or antibody, a nucleic acid encoding the anti-TLR7 agent or antibody may be isolated and inserted into a replicable vector for further cloning (amplification of the DNA) or for expression. In certain instances, an anti-TLR7 agent or antibody may be produced by homologous recombination, e.g. as described in U.S. Pat. No. 5,204,244, specifically incorporated herein by reference. DNA encoding an anti-TLR7 agent or antibody can be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence, e.g., as described in U.S. Pat. No. 5,534,615 issued Jul. 9, 1996 and specifically incorporated herein by reference.

Suitable host cells for cloning or expressing DNA in vectors herein are prokaryote, yeast, or higher eukaryote cells. Suitable prokaryotes for this purpose include *eubacteria*, such as Gram-negative or Gram-positive organisms, for example, *Enterobacteriaceae* such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776

(ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-TLR7 agent/antibody-encoding vectors. *Saccharomyces cerevisiae*, or common bakers yeast, is the most commonly used among lower eukaryotic host microorganisms. A number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of anti-TLR7 agents/ antibodies (e.g., glycosylated anti-TLR7 agents/antibodies) are derived from multicellular organisms. Examples of invertebrate cells include plant and insect cells. Numerous baculoviral strains and variants and corresponding permissive insect host cells from hosts such as *Spodoptera frugiperda*(caterpillar), *Aedes aegypti* (mosquito), *Aedes albopictus* (mosquito), *Drosophila melanogaster* (fruitfly), and *Bombyx mori* (silk moth) have been identified. A variety of viral strains for transfection are publicly available, e.g., the L-1 variant of *Autographa californica* NPV and the Bm-5 strain of *Bombyx mori* NPV, and such viruses may be used as the virus herein according to the present technology, particularly for transfection of *Spodoptera frugiperda* cells. Plant cell cultures of cotton, corn, potato, soybean, petunia, tomato, and tobacco can also be utilized as hosts.

Suitable host cells for the expression of anti-TLR7 agents/ antibodies also may include vertebrate cells (e.g., mammalian cells). Vertebrate cells may be propagated in culture (tissue culture). Examples of useful mammalian host cell lines include monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse Sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells may be transformed with the above-described expression or cloning vectors for antibody production and cultured in conventional nutrient media modified as appropriate for inducing promoters, selecting transformants, or amplifying the genes encoding the desired sequences.

Host cells used to produce an agent/antibody herein may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, an agent/antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology 10:163-167 (1992) describe a procedure for isolating antibodies that are secreted to the periplasmic space of *E. coli.* Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The agent/antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, Bakerbond ABX™ resin (J. T. Baker, Phillipsburg, N.J.) is useful for purification. Other techniques for protein purification, such as fractionation on an ion-exchange column, ethanol precipitation, Reverse Phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the agent or antibody of interest and contaminants may be subjected to low pH hydrophobic interaction chromatography using an elution buffer at a pH between about 2.5-4.5, and may be performed at low salt concentrations (e.g., from about 0-0.25 M salt).

Pharmaceutical Formulations, Dosing, and Routes of Administration

The present technology provides anti-TLR7 agents and antibodies and related compositions, which may be useful for elimination of TLR7 expressing cells from the body, for example, and for identification and quantification of the number of TLR7 expressing cells in tissue samples, for example.

Therapeutic methods and compositions of the present technology may be referred to as "TLR7-based" in order to indicate that these therapies can change the relative or absolute numbers of undesirable or toxic TLR7 expressing cells such as lymphomas or autoimmune B lymphocytes.

One way to control the amount of undesirable TLR7 expressing cells in a patient is by providing a composition that comprises one or more anti-TLR7 antibodies to cause cytotoxic activity towards the TLR7-expressing cells, for example.

Anti-TLR7 agents/antibodies may be formulated in a pharmaceutical composition that is useful for a variety of purposes, including the treatment of diseases, disorders or physical trauma. Pharmaceutical compositions comprising one or more anti-TLR7 agents/antibodies herein may be incorporated into kits and medical devices for such treatment. Medical devices may be used to administer pharmaceutical compositions herein to a patient in need thereof, and according to one embodiment of the technology, kits are provided that include such devices. Such devices and kits may be designed for routine administration, including self-administration, of the pharmaceutical compositions herein.

Therapeutic formulations of an agent or antibody may be prepared for storage by mixing the agent/antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Formulations herein may also contain more than one active compound as necessary for the particular indication being treated, preferably those with complementary activities that do not adversely affect each other. Such molecules are suitably present in combination in amounts that are effective for the purpose intended.

Active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Formulations for in vivo administration generally are sterile. This may be accomplished for instance by filtration through sterile filtration membranes, for example.

Sustained-release preparations may be prepared. Suitable examples of sustained-release preparations include semipermeable matrices of solid hydrophobic polymers containing the agent/antibody, which matrices are in the form of shaped articles, e.g., films, or microcapsule. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated agents/antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

For therapeutic applications, anti-TLR7 agents, e.g., antibodies, provided herein are administered to a mammal, e.g., a human, in a pharmaceutically acceptable dosage form such as those discussed above, including those that may be administered to a human intravenously as a bolus or by continuous infusion over a period of time, or by intramuscular, intraperitoneal, intra-cerebrospinal, subcutaneous, intra-articular, intrasynovial, intrathecal, oral, topical, or inhalation routes.

For the prevention or treatment of disease, the appropriate dosage of agent/antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 μg/kg to about 50 mg/kg (e.g., 0.1-20 mg/kg) of antibody may be an initial candidate dosage for administration to the patient, whether, for example, by one or more separate administrations, or by continuous infusion. A typical daily or weekly dosage might range from about 1 μg/kg to about 20 mg/kg or more, depending on the factors mentioned above. For repeated administrations over several days or longer, depending on the condition, the treatment is repeated until a desired suppression of disease symptoms occurs. However, other dosage regimens may be useful. The progress of this therapy is easily monitored by conventional techniques and assays, including, for example, radiographic imaging. Detection methods using the antibody to determine TLR7 levels in bodily fluids or tissues may be used in order to optimize patient exposure to the therapeutic antibody.

In some embodiments, a composition comprising an anti-TLR7 agent herein (e.g., an mAb that interferes with TLR7 activity) is administered as a monotherapy, and in some embodiments, the composition comprising the anti-TLR7 agent is administered as part of a combination therapy. In some cases, the effectiveness of the agent/antibody in preventing or treating disease may be improved by administering the agent/antibody serially or in combination with another agent that is effective for those purposes, such as a chemotherapeutic drug for treatment of cancer or a microbial infection. In other cases, the anti-TLR7 agent may serve to enhance or sensitize cells to chemotherapeutic treatment, thus permitting efficacy at lower doses and with lower toxicity. Certain combination therapies include, in addition to administration of the composition comprising an agent that reduces the number of TLR7 expressing cells, delivering a second therapeutic regimen selected from the group consisting of administration of a chemotherapeutic agent, radiation therapy, surgery, and a combination of any of the foregoing.

Such other agents may be present in the composition being administered or may be administered separately. Also, the anti-TLR agent may be suitably administered serially or in combination with the other agent or modality, e.g., chemotherapeutic drug or radiation for treatment of cancer, infection, and the like, or an immunosuppressive drug.

Research and Diagnostic, Including Clinical Diagnostic, Uses for Anti-TLR7 Agents Herein Provided herein are diagnostic reagents comprising an anti-TLR7 agent described herein. For example, anti-TLR7 agents, e.g., antibodies, provided herein may be used to detect and/or purify TLR7, e.g., from bodily fluid(s) or expressed on cells in bodily fluids or tissues. Also provided herein are methods for detecting TLR7. For example, a method may comprise contacting a sample (e.g., a biological sample known or suspected of to contain TLR7) with an anti-TLR7 agent provided herein, and, if the sample contains TLR7, detecting TLR7: anti-TLR7 complexes. Also provided herein are reagents comprising an anti-TLR7 agent described herein and methods for detecting TLR7 for research purposes.

Anti-TLR7 antibodies, for example, may be useful in diagnostic assays for TLR7, e.g., detecting its presence in specific cells, tissues, or bodily fluids. Such diagnostic methods may be useful in diagnosis, e.g., of a hyperproliferative disease or disorder. Thus clinical diagnostic uses as well as research uses are comprehended herein.

In some embodiments, an anti-TLR7 agent/antibody comprises a detectable marker or label. In some embodiments, an anti-TLR7 agent/antibody is conjugated to a detectable marker or label. For example, for research and diagnostic applications, an anti-TLR7 agent/antibody may be labeled with a detectable moiety. Numerous labels are available which are generally grouped into the following categories:

(a) Radioisotopes, such as $^{35}$S, $^{14}$C, $^{125}$I, $^{3}$H, and $^{131}$I. The antibody can be labeled with the radioisotope using the techniques described in Current Protocols in Immunology, Volumes 1 and 2, Coligen et al., Ed. Wiley-Interscience, New York, N.Y., Pubs. (1991), for example, and radioactivity can be measured using scintillation counting.

(b) Fluorescent labels such as rare earth chelates (europium chelates) or fluorescein and its derivatives, rhodamine and its derivatives, dansyl, Lissamine, phycoerythrin, Texas Red and Brilliant Violet™ are available. The fluorescent labels can be conjugated to the antibody using the techniques disclosed in Current Protocols in Immunology, supra, for example. Fluorescence can be quantified using a flow cytometer, imaging microscope or fluorimeter.

(c) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured (using a chemilluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, beta-galactosidase, glucoamylase, lysozyme, saccharide oxidases (e.g., glucose oxidase, galactose oxidase, and glucose-6-phosphate dehydrogenase), heterocyclicoxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym. (ed J. Langone & H. Van Vunakis), Academic press, New York, 73:147-166 (1981).

Examples of enzyme-substrate combinations include, for example:

(i) Horseradish peroxidase (HRP) with hydrogen peroxidase as a substrate, where the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) .beta.-D-galactosidase (.beta.-D-Gal) with a chromogenic substrate (e.g., p-nitrophenyl-β-D-galactosidase) or fluorogenic substrate 4-methylumbelliferyl-.beta.-D-galactosidase.

Numerous other enzyme-substrate combinations may be used (e.g., U.S. Pat. Nos. 4,275,149 and 4,318,980, each of which is incorporated by reference herein).

In certain instances, the label is indirectly conjugated with the agent/antibody. The skilled artisan will be aware of various techniques for achieving this. For example, an antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In some embodiments, an anti-TLR7 agent/antibody need not be labeled, and the presence thereof can be detected, e.g., using a labeled antibody which binds to an anti-TLR7 antibody.

In some embodiments, an anti-TLR7 agent/antibody herein is immobilized on a solid support or substrate. In some embodiments, an anti-TLR7 agent/antibody herein is non-diffusively immobilized on a solid support (e.g., the anti-TLR7 agent/antibody does not detach from the solid support). A solid support or substrate can be any physically separable solid to which an anti-TLR7 agent/antibody can be directly or indirectly attached including, but not limited to, surfaces provided by microarrays and wells, and particles such as beads (e.g., paramagnetic beads, magnetic beads, microbeads, nanobeads), microparticles, and nanoparticles. Solid supports also can include, for example, chips, columns, optical fibers, wipes, filters (e.g., flat surface filters), one or more capillaries, glass and modified or functionalized glass (e.g., controlled-pore glass (CPG)), quartz, mica, diazotized membranes (paper or nylon), polyformaldehyde, cellulose, cellulose acetate, paper, ceramics, metals, metalloids, semiconductive materials, quantum dots, coated beads or particles, other chromatographic materials, magnetic particles; plastics (including acrylics, polystyrene, copolymers of styrene or other materials, polybutylene, polyurethanes, TEFLON™, polyethylene, polypropylene, polyamide, polyester, polyvinylidenedifluoride (PVDF), and the like), polysaccharides, nylon or nitrocellulose, resins, silica or silica-based materials including silicon, silica gel, and modified silicon, Sephadex®, Sepharose®, carbon, metals (e.g., steel, gold, silver, aluminum, silicon and copper), inorganic glasses, conducting polymers (including polymers such as polypyrole and polyindole); micro or nanostructured surfaces such as nucleic acid tiling arrays, nanotube, nanowire, or nanoparticulate decorated surfaces; or porous surfaces or gels such as methacrylates, acrylamides, sugar polymers, cellulose, silicates, or other fibrous or stranded polymers. In some embodiments, the solid support or substrate may be coated using passive or chemically-derivatized coatings with any number of materials, including polymers, such as dextrans, acrylamides, gelatins or agarose. Beads and/or particles may be free or in connection with one another (e.g., sintered). In some embodiments, a solid support or substrate can be a collection of particles. In some embodiments, the particles can comprise silica, and the silica may comprise silica dioxide. In some embodiments the silica can be porous, and in certain embodiments the silica can be non-porous. In some embodiments, the particles further comprise an agent that confers a paramagnetic property to the particles. In certain embodiments, the agent comprises a metal, and in certain embodiments the agent is a metal oxide, (e.g., iron or iron oxides, where the iron oxide contains a mixture of Fe2+ and Fe3+). An anti-TLR7 agent/antibody may be linked to a solid support by covalent bonds or by non-covalent interactions and may be linked to a solid support directly or indirectly (e.g., via an intermediary agent such as a spacer molecule or biotin).

Agents and antibodies provided herein may be employed in any known assay method, such as flow cytometry, immunohistochemistry, immunofluorescence, mass cytometry (e.g., Cytof instrument), competitive binding assays, direct and indirect sandwich assays, and immunoprecipitation assays. Zola, Monoclonal Antibodies: A Manual of Techniques, pp. 147-158 (CRC Press, Inc. 1987).

Flow cytometry and mass cytometry assays generally involve the use of a single primary antibody to specifically identify the presence of the target molecule expressed on the surface of a dispersed suspension of individual cells. The dispersed cells are typically obtained from a biological fluid sample, e.g., blood, but may also be obtained from a dispersion of single cells prepared from a solid tissue sample such as spleen or tumor biopsy. The primary antibody may be directly conjugated with a detectable moiety, e.g., a fluorophore such as phycoerythrin for flow cytometry or a heavy metal chelate for mass cytometry. Alternatively, the primary antibody may be unlabeled or labeled with an undetectable tag such as biotin, and the primary antibody is then detected by a detectably labeled secondary antibody that specifically recognizes the primary antibody itself or the tag on the primary antibody. The labeled cells are then analyzed in an instrument capable of single cell detection, e.g., flow cytometer, mass cytometer, fluorescence microscope or brightfield light microscope, to identify those individual cells in the dispersed population or tissue sample that express the target recognized by the primary antibody. Detailed description of the technological basis and practical application of flow cytometry principles may be found in, e.g., Shapiro, Practical Flow Cytometry, 4$^{th}$ Edition, Wiley, 2003.

Sandwich assays involve the use of two antibodies, each capable of binding to a different immunogenic portion, or epitope, of the protein that is detected. In a sandwich assay, the test sample analyte is bound by a first antibody that is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme. In a cell ELISA, the target cell population may be attached to the solid support using antibodies first attached to the support and that recognize different cell surface proteins. These first antibodies capture the cells to the support. TLR7 on the surface of the cells can then be detected by adding anti-TLR7 antibody to the captured cells and detecting the amount of TLR7 antibody attached to the cells. In certain instances, fixed and permeabilized cells may be used, and in such instances, surface TLR7 and intracellular TLR7 may be detected.

For immunohistochemistry, the blood or tissue sample may be fresh or frozen or may be embedded in paraffin and fixed with a preservative such as formalin, for example.

The agents/antibodies herein also may be used for in vivo diagnostic assays. Generally, the antibody is labeled with a radionuclide (such as $^{111}$In, $^{99}$Tc, $^{14}$C, $^{131}$I, $^{125}$I, $^{3}$H, $^{32}$P, or $^{35}$S) so that the bound target molecule can be localized using immunoscintillography.

Detection of TLR7 in Immune Cells

Provided herein are agents and methods for detecting TLR7 in immune cells. Detection of TLR7 in immune cells may refer to detection on the surface of immune cells (e.g., by surface staining) and/or inside immune cells (e.g., by intracellular staining). In some embodiments, agents and methods are provided for detecting TLR7 in a heterogeneous population of immune cells. A heterogeneous population of immune cells may comprise two or more types of immune cells. For example a heterogeneous population of immune cells may comprise two or more of B cells, plasmacytoid dendritic cells (pDCs), lymphocytes, leukocytes, T cells, monocytes, macrophages, neutrophils, myeloid dendritic cells (mDCs), innate lymphoid cells, mast cells, eosinophils, basophils, natural killer cells, and the like. In some embodiments, a heterogeneous population of immune cells comprises peripheral blood mononuclear cells (PBMCs) which may include, for example, T cells, B cells, natural killer cells, and monocytes.

Generally, cells are contacted with an anti-TLR7 agent described herein (e.g., in a flow cytometry assay as described in Example 3; or any suitable protein or cell detection assay). In some embodiments, TLR7 is detected at a significant level in certain immune cells by an anti-TLR7 agent described herein. TLR7 may be detected at a significant level by an anti-TLR7 agent described herein in certain immune cells and not significantly detected in other immune cells. The level of TLR7 detection in certain immune cells may vary according to certain factors such as, for example, type of detection assay, type of detection reagent (e.g., type of dye), antibody concentration, donor cell variability, and the like.

Detection of TLR7 at a significant level may refer to a particular signal to noise (S:N) ratio (e.g., threshold or range) measured in a flow cytometry assay.

In some embodiments, TLR7 is detected at a significant level in plasmacytoid dendritic cells (pDCs). In certain instances, plasmacytoid dendritic cells (pDCs) may be identified by the expression of CD304. Accordingly, in some embodiments, TLR7 is detected at a significant level in CD304$^+$ plasmacytoid dendritic cells (pDCs). CD304, also referred to as neuropilin-1, BDCA-4 and VEGF165R, is a 140 kD type I transmembrane protein. Its extracellular region contains 2 CUB, 2 FV/FVIII, and one MAM domain; a soluble isoform is produced by alternative mRNA splicing. CD304 is involved in angiogenesis, neural development, and tumor metastasis, and may be expressed by plasmacytoid dendritic cells, thymocytes, neurons, endothelium, and a subset of TFH cells. CD304 also may be expressed in several carcinomas, and a high expression of this molecule in prostate cancer may correlate with a poor prognosis.

In some embodiments, TLR7 is detected at a significant level in B cells. In certain instances, B cells may be identified by the expression of CD19 and by the lack of expression of CD3. Accordingly, in some embodiments, TLR7 is detected at a significant level in CD19$^+$CD3$^-$ B cells. CD19 is a 95 kD type I transmembrane glycoprotein also referred to as B4. It is a member of the immunoglobulin superfamily expressed on B-cells (from pro-B to blastoid B cells, absent on plasma cells) and follicular dendritic cells. CD19 generally is involved in B cell development, activation, and differentiation. CD19 forms a complex with CD21 (CR2) and CD81 (TAPA-1), and functions as a BCR co-receptor. CD3, also referred to as T3, is a member of the Ig superfamily and primarily expressed on T cells, NK-T cells, and at different levels on thymocytes during T cell differentiation. CD3 is composed of CD3ε, δ, γ and ζ chains, and forms a TCR complex by associating with TCR α/β or γ/δ chains. CD3 is involved in TCR signal transduction, T cell activation, and antigen recognition by binding the peptide/MHC antigen complex.

In some embodiments, TLR7 is not significantly detected in certain immune cells by an anti-TLR7 agent described herein. For example, TLR7 may not be significantly detected in certain lymphocytes (e.g., CD3$^-$CD19$^-$ lymphocytes) and/or T cells (e.g., CD3+CD19$^-$ T cells). No significant detection of TLR7 in certain lymphocytes (e.g., CD3$^-$ CD19$^-$ lymphocytes) and/or T cells (e.g., CD3$^+$CD19$^-$ T cells) may refer to a particular signal to noise (S:N) ratio (e.g., threshold or range) measured in a flow cytometry assay. In some embodiments, no significant detection of TLR7 in certain lymphocytes (e.g., CD3$^-$CD19$^-$ lymphocytes) and/or T cells (e.g., CD3$^+$CD19$^-$ T cells) refers to a signal to noise (S:N) ratio of about 1.5 or less. In some embodiments, no significant detection of TLR7 in certain lymphocytes (e.g., CD3$^-$CD19$^-$ lymphocytes) and/or T cells (e.g., CD3$^+$CD19$^-$ T cells) refers to a signal to noise (S:N) ratio of about 1 or less.

Provided herein are agents and methods for detecting TLR7 on the inside of immune cells (e.g., by intracellular staining). In some embodiments, TLR7 is detected on the inside of plasmacytoid dendritic cells (pDCs) (e.g., CD304$^+$ plasmacytoid dendritic cells (pDCs)). In some embodiments, TLR7 is detected on the inside of plasmacytoid dendritic cells (pDCs) (e.g., CD304$^+$ plasmacytoid dendritic cells (pDCs)) in a flow cytometry assay. In some embodiments, TLR7 is detected on the inside of plasmacytoid dendritic cells (pDCs) (e.g., CD304$^+$ plasmacytoid dendritic cells (pDCs)) in a flow cytometry assay with a signal to noise (S:N) ratio of about 5 or greater. In some embodiments, TLR7 is detected on the inside of plasmacytoid dendritic cells (pDCs) (e.g., CD304$^+$ plasmacytoid dendritic cells (pDCs)) in a flow cytometry assay with a signal to noise (S:N) ratio of about 10 or greater. In some embodiments, TLR7 is detected on the inside of plasmacytoid dendritic cells (pDCs) (e.g., CD304$^+$ plasmacytoid dendritic cells (pDCs)) in a flow cytometry assay with a signal to noise (S:N) ratio of about 14 or greater. The above signal to noise (S:N) ratio examples for detection of TLR7 on the inside of plasmacytoid dendritic cells (pDCs) may vary according to certain factors such as, for example, type of detection assay, type of detection reagent (e.g., type of dye), antibody concentration, donor cell variability, and the like.

In some embodiments, TLR7 is detected on the inside of B cells (e.g., CD19$^+$CD3$^-$ B cells). In some embodiments, TLR7 is detected on the inside of B cells (e.g., CD19$^+$CD3$^-$ B cells) in a flow cytometry assay. In some embodiments, TLR7 is detected on the inside of B cells (e.g., CD19$^+$CD3$^-$ B cells) in a flow cytometry assay with a signal to noise (S:N) ratio of about 2 or greater. In some embodiments, TLR7 is detected on the inside of B cells (e.g., CD19$^+$CD3$^-$ B cells) in a flow cytometry assay with a signal to noise (S:N) ratio of about 3 or greater. In some embodiments, TLR7 is detected on the inside of B cells (e.g., CD19$^+$CD3$^-$ B cells) in a flow cytometry assay with a signal to noise (S:N) ratio of about 4 or greater. In some embodiments, TLR7 is detected on the inside of B cells (e.g., CD19$^+$CD3$^-$ B cells) in a flow cytometry assay with a signal to noise (S:N) ratio of about 4.02 or greater. The above signal to noise (S:N) ratio examples for detection of TLR7 on the inside of B cells may vary according to certain factors such as, for example, type of detection assay, type of detection reagent (e.g., type of dye), antibody concentration, donor cell variability, and the like.

In some embodiments, TLR7 is detected on the inside of monocytes (e.g., CD14$^+$ monocytes). In some embodiments, TLR7 is detected on the inside of monocytes (e.g., CD14$^+$ monocytes) in a flow cytometry assay. In some embodiments, TLR7 is detected on the inside of monocytes (e.g., CD14$^+$ monocytes) in a flow cytometry assay with a signal to noise (S:N) ratio of about 2 or greater. In some embodiments, TLR7 is detected on the inside of monocytes (e.g., CD14$^+$ monocytes) in a flow cytometry assay with a signal to noise (S:N) ratio of about 3 or greater. In some embodiments, TLR7 is detected on the inside of monocytes (e.g., CD14$^+$ monocytes) in a flow cytometry assay with a signal to noise (S:N) ratio of about 4 or greater. The above signal to noise (S:N) ratio examples for detection of TLR7 on the inside of monocytes may vary according to certain factors such as, for example, type of detection assay, type of detection reagent (e.g., type of dye), antibody concentration, donor cell variability, and the like.

Kits Incorporating Anti-TLR7 Agents Herein

An anti-TLR7 agent (e.g., an anti-TLR7 antibody) herein may be provided in a kit, for example, a packaged combination of reagents in predetermined amounts with instructions for use (e.g., instructions for performing a diagnostic assay; instructions for performing a laboratory assay). In some embodiments, the kit is a diagnostic kit configured to detect TLR7 in a sample (e.g., a biological sample). Where the anti-TLR7 agent is labeled with a fluorophore, the kit may include an identical isotype negative control irrelevant antibody to control for non-specific binding of the anti-TLR7 agent. Where the anti-TLR7 agent is labeled with an enzyme, the kit may include substrates and cofactors required by the enzyme (e.g., a substrate precursor which provides the detectable chromophore or fluorophore). Additional additives may be included such as stabilizers, buffers (e.g., a block buffer or lysis buffer), and the like. The relative amounts of the various reagents may be varied widely to provide for concentrations in solution of the reagents that substantially optimize the sensitivity of the assay. In certain instances, reagents may be provided as dry powders (e.g., lyophilized powder), including excipients that on dissolution will provide a reagent solution having the appropriate concentration.

Articles of Manufacture

In another aspect of the present technology, an article of manufacture containing materials useful for the treatment, or diagnosis, of the disorders described above is provided. An article of manufacture may comprise a container and a label. Suitable containers include, for example, bottles, vials, syringes, and test tubes. Containers may be formed from a variety of materials such as glass or plastic. A container may hold a composition that is effective for treating a condition and may have a sterile access port (for example the container may be an intravenous solution bag or a vial having a stopper pierceable by a hypodermic injection needle). An active anti-TLR7 agent in the composition may be an anti-TLR7 antibody. A label on, or associated with, the container indicates that the composition is used for treating, or diagnosing, a condition of choice. The article of manufacture may further comprise a second container comprising a pharmaceutically acceptable buffer, such as phosphate-buffered saline, Ringer's solution and dextrose solution; and may further include other materials desirable from a commercial and user standpoint, including other buffers, diluents, filters, needles, syringes, and package inserts with instructions for use.

Definitions

An "acceptor human framework" generally refers to a framework comprising the amino acid sequence of a heavy chain variable domain (VH) framework or a light chain variable domain (VL) framework derived from a human immunoglobulin framework or a human consensus framework, as defined herein. An acceptor human framework "derived from" a human immunoglobulin framework or a human consensus framework may comprise the same amino acid sequence thereof, or it may contain amino acid sequence changes. In some embodiments, the number of framework amino acid changes are 10 or less, 9 or less, 8 or less, 7 or less, 6 or less, 5 or less, 4 or less, 3 or less, or 2 or less. In some embodiments, the VH and/or VL acceptor human framework(s) is(are) identical in sequence to the VH and/or VL human immunoglobulin framework amino acid sequence or human consensus framework amino acid sequence.

"Framework" or "FR" generally refers to variable domain residues other than hypervariable region (HVR) residues. The FR of a variable domain generally consists of four FR domains: FR1; FR2; FR3; and FR4. Accordingly, the HVR and FR sequences generally appear in the following sequence in VH (or VL): FR1-H1(L1)-FR2-H2(L2)-FR3-H3(L3)-FR4.

A "human consensus framework" generally refers to a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In some embodiments, for the VL, the subgroup is subgroup kappa I as in Kabat et al., supra. In some embodiments, for the VH, the subgroup is subgroup III as in Kabat et al., supra.

The term "hypervariable region" or "HVR" generally refers to each of the regions of an antibody variable domain that are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition.

The precise amino acid sequence boundaries of a given CDR or FR can be readily determined using any number of well-known schemes, including those described in Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), MacCallum et al., J. Mol. Biol. 262:732-745 (1996), "Antibody-antigen interactions: Contact analysis and binding site topography," J. Mol. Biol. 262, 732-745," ("Contact" numbering scheme), Martin et al., Proc. Natl. Acad. Sci., 86:9268-9272 (1989) ("AbM" numbering scheme), Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme), and Honegger A and Plückthun A, "Yet another numbering scheme for immunoglobulin variable domains: an automatic modeling and analysis tool," J Mol Biol, 2001 Jun. 8; 309(3):657-70, ("Aho" numbering scheme).

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a" and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

Table 4, below, lists exemplary position boundaries of CDRH1, CDRH2, CDRH3, and CDRL1, CDRL2, and CDRL3 as identified by Kabat, Chothia, and Contact schemes, respectively. For CDRH1, residue numbering is listed using both the Kabat and Chothia numbering schemes. FRs are located between CDRs, for example, with FRH1 located between CDRH1 and CDRH2, and so forth. It is noted that because the shown Kabat numbering scheme places insertions at H35A and H35B, the end of the Chothia CDRH1 loop when numbered using the shown Kabat numbering convention varies between H32 and H34, depending on the length of the loop.

TABLE 4

| CDR | Kabat | Chothia | AbM | Contact |
|---|---|---|---|---|
| CDRH1 (Kabat Numbering[1]) | H31--H35B | H26--H32 . . . 34 | H26--H35B | H30--H35B |
| CDRH1 (Chothia Numbering[2]) | H31--H35 | H26--H32 | H26--H35 | H30--H35 |
| CDRH2 | H50--H65 | H52--H56 | H50--H58 | H47--H58 |
| CDRH3 | H95--H102 | H95--H102 | H95--H102 | H93--H101 |
| CDRL1 | L24--L34 | L24--L34 | L24--L34 | L30--L36 |
| CDRL2 | L50--L56 | L50--L56 | L50--L56 | L46--L55 |
| CDRL3 | L89--L97 | L89--L97 | L89--L97 | L89--L96 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273, 927-948

CDRs also comprise "specificity determining residues," or "SDRs," which are residues that contact a particular antigen. Unless otherwise indicated, HVR residues and other residues in the variable domain (e.g., FR residues) are numbered herein according to Kabat et al., supra.

The term "variable region" or "variable domain" generally refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al. Kuby Immunology, 6th ed., W. H. Freeman and Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991). "Affinity" generally refers to the strength of the sum total of non-covalent interactions between a single binding site of a molecule (e.g., an antibody) and its binding partner (e.g., an antigen). Unless indicated otherwise, "binding affinity" refers to intrinsic binding affinity, which reflects a 1:1 interaction between members of a binding pair (e.g., antibody and antigen). The affinity of a molecule X for its partner Y can generally be represented by a dissociation constant (Kd). Affinity can be measured by common methods known in the art, including those described herein. Specific illustrative and example embodiments for measuring binding affinity are described elsewhere herein. In some instances, antibodies herein bind to a target (e.g., TLR7) with a high affinity, e.g., a $K_d$ value of no more than about $1\times10^{-7}$ M; preferably no more than about $1\times10^{-8}$ M; and preferably no more than about $5\times10^{-9}$ M.

An "affinity matured" antibody generally refers to an antibody with one or more alterations in one or more hypervariable regions (HVRs), compared to a parent antibody that does not possess such alterations. Preferably, such alterations result in improved affinity of the antibody for its target antigen.

The term "anti-TLR7 agent" generally refers to a molecule that is, or comprises, one or more anti-TLR7 antibodies, TLR7-binding antibody fragments, or TLR7-binding antibody derivatives.

The terms "anti-TLR7 antibody" and "an antibody that binds to TLR7" generally refer to an antibody that is capable of binding TLR7 with sufficient affinity and/or specificity such that the antibody is useful as a research tool, diagnostic agent and/or therapeutic agent in targeting TLR7. In some embodiments, the extent of binding of an anti-TLR7 antibody (or antigen-binding fragment thereof) to an unrelated, non-TLR7 protein is less than about 10% of the binding of the antibody to TLR7 as measured, e.g., by a radioimmunoassay (RIA) or by Scatchard analysis or by surface plasmon resonance, such as, for example, Biacore. In certain embodiments, an antibody that binds to TLR7 has a dissociation constant (Kd) of 0.1 μM, 100 nM, 10 nM, 1 nM, 0.1 nM, 0.01 nM, or 0.001 nM (e.g., $10^{-7}$M or less, e.g., from $10^{-7}$ M to $10^{-13}$ M). In certain embodiments, an anti-TLR7 antibody binds to an epitope of TLR7 that is conserved among TLR7 from different species.

The term "antibody" herein is used in the broadest sense and encompasses various antibody structures, including, but not limited to, monoclonal antibodies, polyclonal antibodies, multispecific antibodies (e.g., bispecific antibodies), and antibody fragments so long as they exhibit the desired antigen-binding activity.

An "antibody derivative" generally refers to a molecule other than an intact antibody that comprises a portion derived from an intact antibody (or antigen-binding fragment thereof) and that binds the antigen to which the intact antibody (or antigen-binding fragment thereof) binds. Examples of antibody derivatives include but are not limited to single chain variable fragments (scFv), diabodies, triabodies, and the like, aptamers comprising multiple antigen-binding antibody fragments, single chain variable fragments, diabodies, triabodies, and the like.

An "antibody fragment" or "antigen-binding antibody fragment" generally refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2 and multispecific antibodies formed from antibody fragments.

The terms "full length antibody," "intact antibody," and "whole antibody" are used herein interchangeably to refer to an antibody having a structure substantially similar to a native antibody structure or having heavy chains that contain an Fc region as defined herein.

The term "Fc region" generally refers to a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

An "antibody that binds to the same epitope" as a reference antibody (e.g., an antibody that binds TLR7) generally refers to an antibody that blocks binding of the reference antibody to its antigen in a competition assay by 50% or more, and conversely, the reference antibody blocks binding of the antibody to its antigen in a competition assay by 50% or more.

The term "chimeric" antibody generally refers to an antibody in which a portion of the heavy and/or light chain is derived from a particular source or species, while the remainder of the heavy and/or light chain is derived from a different source or species.

A "human antibody" generally refers to an antibody that possesses an amino acid sequence corresponding to that of an antibody produced by a human or a human cell or derived from a non-human source that utilizes human antibody repertoires or other human antibody-encoding sequences. This definition of a human antibody specifically excludes a "humanized" antibody comprising non-human antigen-binding residues.

A "humanized" antibody generally refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. In some embodiments, a humanized antibody (or antigen-binding fragment or derivative thereof), when aligned with the antibody from which the acceptor framework regions were derived, includes one or more amino acid substitutions (or deletions or insertions) at desired locations. In some such embodiments, the amino acid residue(s) substituted (or inserted or deleted) at a particular position in the human (or other) or other FR corresponds to the amino acid residue(s) at the corresponding location(s) in the parent antibody (i.e., the non-human antibody from which the CDRs or HVRs were derived). A "humanized form" of an antibody, e.g., a non-human antibody, refers to an antibody that has undergone humanization.

The term "antibody drug conjugate" (ADC) or "immunoconjugate" generally refers to a particular class of agent-drug conjugates. Here, "agent-drug conjugate" is an anti-TLR7 agent (e.g., an anti-TLR7 antibody or TLR7-binding fragment or derivative thereof) conjugated to one or more heterologous molecule(s), including, but not limited to, a cytotoxic agent.

The term "cytotoxic agent" generally refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$, and radioactive isotopes of Lu); chemotherapeutic agents or drugs (e.g., methotrexate, adriamycin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

A "diagnostic reagent" generally refers to a compound, e.g., a target-specific antibody (or antigen-binding thereof) used to perform a diagnostic assay.

"Effector functions" generally refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, generally refers to an amount effective, at dosages and for periods of time necessary, to achieve the desired therapeutic or prophylactic result.

The term "epitope" generally refers to the particular site on an antigen molecule to which an antibody binds.

The terms "host cell", "host cell line", and "host cell culture" are used interchangeably and generally refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "rabbit antibody" generally refers to an antibody that possesses an amino acid sequence that corresponds to that of an antibody produced by a rabbit or a rabbit cell or derived from a non-rabbit source that utilizes rabbit antibody repertoires or other rabbit antibody-encoding sequences.

An "immunoconjugate" generally refers to an antibody (or antigen-binding fragment or derivative thereof) conjugated to one or more heterologous molecule(s), including, but not limited to, a cytotoxic agent. An immunoconjugate is equivalent to the term "antibody drug conjugate" (ADC).

An "individual" or "patient" or "subject" generally is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" molecule (e.g., nucleic acid, antibody) generally refers to a molecule that has been separated from a component of its original environment (e.g., the natural environment if it is naturally occurring, or a host cell if expressed exogenously), and thus is altered by human intervention (e.g., "by the hand of man") from its original environment. In some embodiments, for example, an antibody is purified to greater than 95% or 99% purity as determined by, for example, electrophoretic (e.g., SDS- PAGE, isoelectric focusing (IEF), capillary electrophoresis) or chromatographic (e.g., ion exchange or reverse phase HPLC). An isolated nucleic acid may refer to a nucleic acid molecule contained in cells that ordinarily contain the nucleic acid molecule, but the nucleic acid molecule is present extrachromosomally or at a chromosomal location that is different from its natural chromosomal location. In some embodiments, an isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components.

"Isolated nucleic acid encoding an anti-TLR7 antibody" or "isolated polynucleotide encoding an anti-TLR7 antibody" generally refers one or more nucleic acid molecules encoding antibody heavy and light chains (or fragments thereof), including such nucleic acid molecule(s) in a single vector or separate vectors, and such nucleic acid molecule(s) present at one or more locations in a recombinant host cell.

The term "TLR7" generally refers to any native, mature TLR7 that results from processing of a TLR7 precursor protein in a cell. The term includes TLR7 from any vertebrate source, including mammals such as primates (e.g. humans and cynomolgus or rhesus monkeys) and rodents (e.g., mice and rats), unless otherwise indicated. The term also includes naturally occurring variants of TLR7, e.g., splice variants or allelic variants. The amino acid sequence of an example full-length human TLR7 precursor protein is shown in FIG. 1 (SEQ ID NO: 48; of the 1,049 amino residues, the first 26 are a signal peptide and residues 27-1,049 constitute the mature, processed protein).

The term "TLR7-positive cell" generally refers to any cell that expresses TLR7 on its surface or on an intracellular membrane or organelle (e.g., endosome, ER, Golgi apparatus, lysosome, and the like). Some cells, including those infected by a microbe or associated with some cancer types and tumors, exhibit up-regulation of TLR7 expression.

The term "monoclonal antibody" generally refers to an antibody obtained from a population of substantially homogeneous antibodies, i.e., the individual antibodies comprising the population are identical (as assessed at the level of Ig heavy and/or light chain amino acid sequence) and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present technology may be made by a variety of techniques, including, but not limited to, the hybridoma method, recombinant DNA methods, phage-display methods, and methods utilizing transgenic animals containing all or part of the human immunoglobulin loci, such methods and other example methods for making monoclonal antibodies being described herein.

The term "package insert" generally refers to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence generally refers to the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

The term "pharmaceutical composition" generally refers to a preparation that is in such form as to permit the biological activity of an active ingredient contained therein to be effective, and which contains no additional components which are unacceptably toxic to a subject to which the formulation would be administered.

A "pharmaceutically acceptable carrier" generally refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") generally refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies herein are used to delay development of a disease or to slow the progression of a disease.

The term "vector" generally refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

EXAMPLES

The examples set forth below illustrate certain embodiments and do not limit the technology.

Example 1: Creation and Characterization of Anti-TLR7 Hybridomas

Hybridomas that secrete monoclonal antibody that reacts with TLR7 as expressed in vivo can be prepared as described in this Example. The resulting anti-TLR7 antibodies can be used for a variety of purposes, including in diagnostic assays, examples of which are provided in Examples 3 and 4 below.

Common strains of laboratory mice, e.g., BALB/c or C57/Bl6, or rats, e.g., Sprague Dawley, are suitable hosts for immunization with a TLR7 immunogen. Following successful immunization of mice, hybridomas are formed using standard protocols to fuse myeloma cells with spleen and draining lymph node cells harvested from the animals. Following selection of successful fusions in HAT medium and cloning to approximately one cell/well in microtiter plates, the culture supernatants can be tested against TLR7-expressing cell transfectants, e.g., HEK 293 or RBL, by flow cytometry. Wells with successful staining profiles are then subcultured into larger vessels until sufficient cells are present to allow subcloning. Further characterization of the hybridoma subclone candidates can again be performed by flow cytometry using TLR7-transfected cells. Clones selected as the best candidates are then further screened, for example, by flow cytometry against human blood cells divided into distinct subsets (e.g., lymphocytes, monocytes, and the like) as well as against one or more cell lines generated from diseased and/or infected human cells. As compared to an isotype control, the percentage of positive cells in each blood cell subset can be quantified.

One example of an ideal candidate clone will have strong reactivity against immune cells that express TLR7 (e.g., plasmacytoid dendritic cells (pDCs), B cells, monocytes) but no appreciable reactivity against other blood cell populations (e.g., certain lymphocytes, T cells). In certain instances, an ideal candidate clone can detect TLR7 on the cell surface. In certain instances, an ideal candidate clone can detect TLR7 on the cell surface of plasmacytoid dendritic cells (pDCs). In certain instances, an ideal candidate clone can detect intracellular TLR7. In certain instances, an ideal candidate clone can detect intracellular TLR7 in plasmacytoid dendritic cells (pDCs). In certain instances, an ideal candidate clone can detect intracellular TLR7 in B cells. In certain instances, an ideal candidate clone can detect intracellular TLR7 in monocytes. In certain instances, an ideal candidate clone can detect intracellular TLR7 in plasmacytoid dendritic cells (pDCs), B cells, and monocytes.

Example 2: Sequencing of the Anti-TLR7 Antibody Variable Regions

Cells from well-performing anti-TLR7 hybridoma cell lines (described in Example 1, above) were grown in standard mammalian tissue culture media. Total RNA was isolated from hybridoma cells from various clones expressing anti-TLR monoclonal antibodies using a procedure based on the RNeasy Mini kit (Qiagen). The RNA was used to generate first strand cDNA. Both light chain and heavy chain variable domain cDNAs were amplified by a 5'-RACE technique. Positive clones were prepared by PCR and then subject to DNA sequencing of multiple clones.

Amino acid sequences of the individual variable domains (CDRs and Framework regions), including the CDR1, CDR2, and CDR3 regions, for both the heavy and light chains for 6 different antibodies (clones), designated AB 1-6 (also referred to herein as antibodies 1-6, and clones 1-6), are shown in FIG. 2. The various heavy and light chain CDR sequences are shown in Table 4, below.

64

TABLE 5

CDR Sequences and Sequence ID Numbers of VH and VL domains for representative anti-TLR7 monoclonal antibodies

| SEQ ID NO | CDR Type | AB (clone) Number(s) | Amino Acid Sequence |
|---|---|---|---|
| 1 | CDRH1 | 1, 2 | DYWMS |
| 2 | CDRH1 | 3 | NYYMA |
| 3 | CDRH1 | 4 | DYYMA |
| 4 | CDRH1 | 5 | DYCVH |
| 5 | CDRH1 | 6 | DYYIH |
| 6 | CDRH2 | 1 | DIKYDGSFIDYAPSLKN |
| 7 | CDRH2 | 2 | DIKYDGTFIDYAPSLKN |
| 8 | CDRH2 | 3 | SITNSGRTTYYRDSVKG |
| 9 | CDRH2 | 4 | SISYEGSSTHYGDSVKA |
| 10 | CDRH2 | 5 | YINPYSGYTNYNEKFKS |
| 11 | CDRH2 | 6 | FINPDSGYTNYNEKFKT |
| 12 | CDRH3 | 1, 2 | DLTTVVDGFAY |
| 13 | CDRH3 | 3 | EGGDLYYSNYNYVRFAY |
| 14 | CDRH3 | 4 | HGGYPNWYFDF |
| 15 | CDRH3 | 5, 6 | GPYGGYSGDGFDY |
| 16 | CDRL1 | 1, 2 | RASEDIYNVLA |
| 17 | CDRL1 | 3 | RASEDIYNELA |
| 18 | CDRL1 | 4 | LPSEDIYNNLA |
| 19 | CDRL1 | 5, 6 | RASQSLSTSIH |
| 20 | CDRL2 | 1 | NANRLHN |
| 21 | CDRL2 | 2 | NANNLHT |
| 22 | CDRL2 | 3 | NANSLHT |
| 23 | CDRL2 | 4 | YASNLQD |
| 24 | CDRL2 | 5, 6 | YASQPIS |
| 25 | CDRL3 | 1 | QQYYDYPNT |
| 26 | CDRL3 | 2 | QQYYDYPHT |
| 27 | CDRL3 | 3 | QQYYDYPWT |
| 28 | CDRL3 | 4 | LQDSDYPFT |
| 29 | CDRL3 | 5, 6 | QQSYSSPYT |

Example 3: Detection of Cells Expressing TLR7

This example describes flow cytometry-based detection of human peripheral blood mononuclear cells (PBMCs) using certain anti-TLR7 monoclonal antibodies provided herein.

Materials and Methods

PBMC Isolation

Human peripheral blood mononuclear cells (PBMCs) were isolated in aseptic conditions through a gradient of Ficoll-Paque PLUS (GE Healthcare) according manufacturer instructions.

Surface and Intracellular Staining

The PBMCs were counted and adjusted in Cell Staining Buffer (BioLegend, cat. #420201) to a cell density of $0.7-1\times10^7$ cells/mL. A 100 µl cell suspension ($0.7-1\times10^6$ total cells) was stained with CD3, CD19, and CD304 for 15 minutes in the dark. For detection of surface CD289/TLR7, isotype (rat IgG2a, k or mouse IgG1, k) or monoclonal TLR7 antibodies (see FIG. 3; AB1, AB2, AB3, AB4, AB5, AB6, or Commercial ABI) were included in the surface cocktail and stained for 15 minutes in the dark. Cells were washed twice with 2 mL of Cell Staining Buffer. For detection of surface CD289/TLR7, cells were resuspended in 300 µL 1% paraformaldehyde and acquired on a cytometer. For detection of intracellular CD289/TLR7, cells were resuspended in 300-500 µL Fixation Buffer (BioLegend, cat. #420801) for 20 minutes in the dark. Cells were washed twice with 2 mL of 1× Intracellular Staining Permeabilization Wash Buffer (BioLegend, cat. #421002) and then stained with isotype (rat IgG2a, k or mouse IgG1, k) or monoclonal TLR7 antibodies (AB1, AB2, AB3, AB4, AB5, AB6, or Commercial ABI) for 30 minutes in the dark. Cells were washed with 2 mL of 1× Intracellular Staining Permeabilization Wash Buffer followed by a 2 mL wash with Cell Staining Buffer. Cells were resuspended in 300 µL of Cell Staining Buffer and acquired on a cytometer. Samples were acquired on a BD Cantoll and analyzed using FlowJo software.

All reagents used are from BioLegend unless otherwise indicated.

Flow Cytometry/Gating Hierarchy

Lymphocytes and monocytes were collectively gated based on their forward (FSC) and side scatter (SSC) profiles. Lymphocytes were $FSC^{lo}SSC^{lo}$ and monocytes were $FSC^{int}SSC^{int}$ (FIG. 4A). From the lymphocyte and monocyte gate, B cells were $CD19^+CD3^-$ and T cells were $CD3+CD19^-$ (FIG. 4B). Some lymphocytes ($FSC^{lo}SSC^{lo}$) were not T cells or B cells ($CD19^-CD3^-$). Monocytes were $CD14^+CD304^+$ cells and plasmacytoid dendritic cells (pDCs) were $CD14^-CD304^+$ cells (FIG. 4C).

Results

Figure 6:
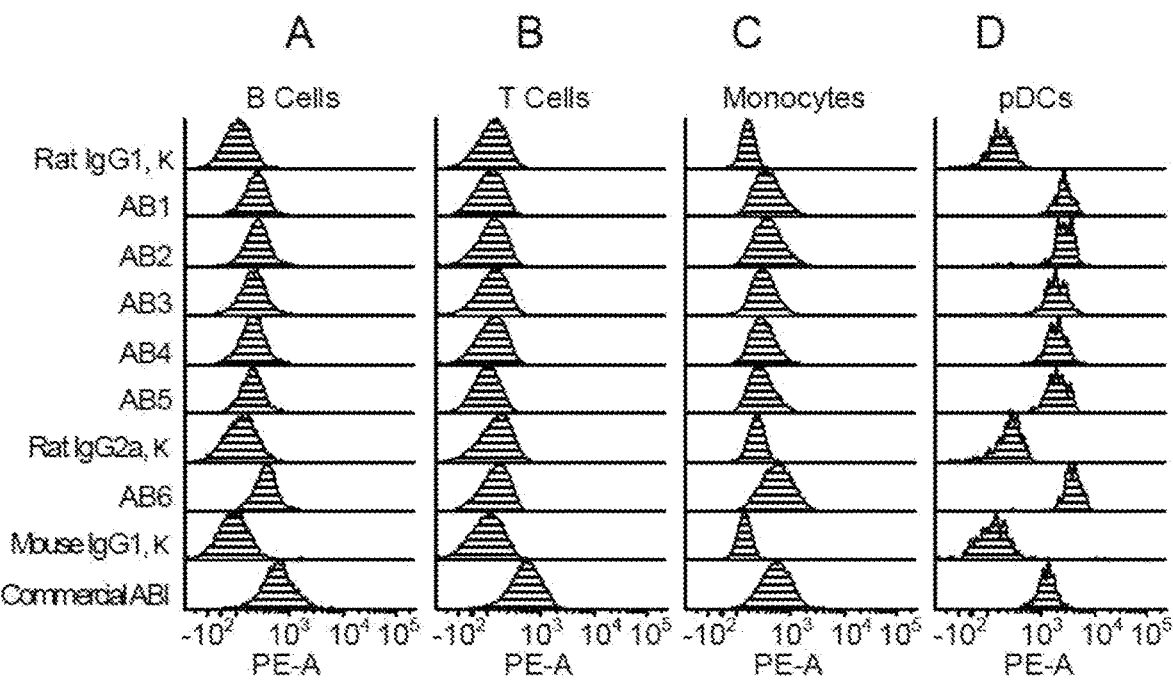
FIG. 6, panels A-D, show the intracellular staining results of experiments described in Example 3, below.

PBMCs were stained intracellularly with each TLR7 antibody as well as isotype control antibody (control) (FIG. 6). No staining was observed on T cells compared to the control. B cells, monocytes and pDCs showed positive staining. Mean fluorescence intensities (MFI) and signal to noise ratios (S:N) of the results for pDCs, B cells, and monocytes are shown in FIGS. 7A-7F. In certain instances, the signal to noise ratio (S:N) was greater compared to a commercial anti-TLT7 antibody. For example, in the pDC population, the S:N for AB6 was 12.0 (at 0.5 µg/T) and the S:N for a commercial anti-TLT7 antibody was 8.4 (at optimal of 1 µg/T); S:N ratio was calculated as the MFI hTLR7 stained/MFI isotype stained.

Figure 5:
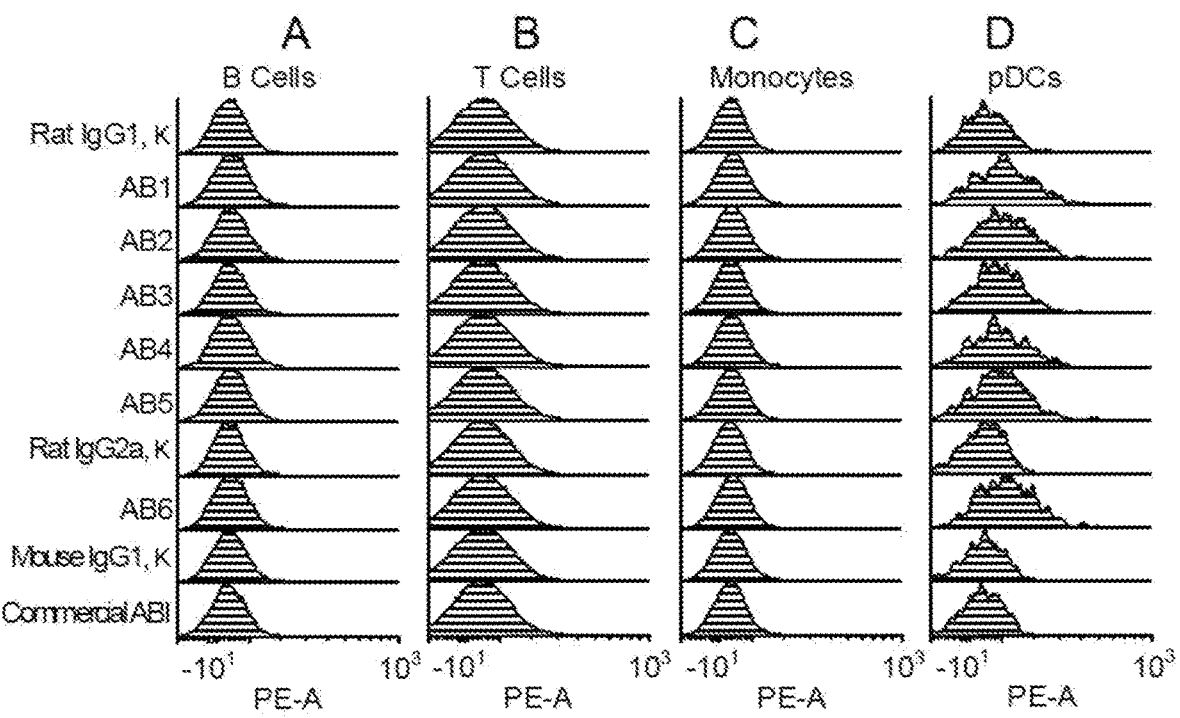
FIG. 5, panels A-D, show the surface staining results of experiments described in Example 3, below.

PBMCs were surface stained with each TLR7 antibody as well isotype control antibody (FIG. 5). No staining was observed on T cells, B cells or monocytes. Dim staining was observed on pDCs compared to isotype.

Example 4: Functional Assay

This example describes a functional assay based on TLR7 detection in cells that overexpress the target.

Experimental

HEK293 cells overexpressing human TLR7 (293XL-hTLR7, Invivogen) were cultured and stimulated according to the manufacturer's instructions. TLR7 recognizes small synthetic molecules such as the imidazoquinioline compound R848 (Sigma Aldrich). This cell line expresses human interleukin-8 through TLR7 stimulation in the presence of R848. Briefly, 800,000 293XL-hTLR7 cells were seeded into the wells of a 96 well plate, cultured overnight, and then incubated with TLR7 antibodies at various concentrations at 37° C. for 15 minutes. 0.01 ug of R848 was added to each well and plate was incubated for 37° C. for 20 hours Supernatants were collected and evaluated for secretion of IL-8 (BioLegend cat. #431504).

Results

Figure 8A:
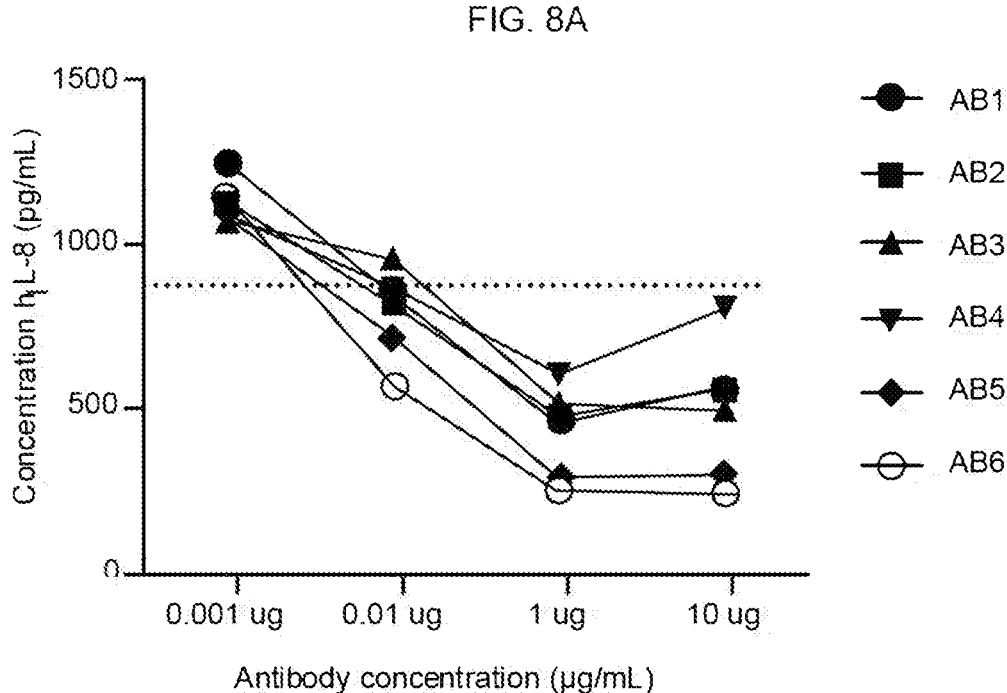
FIGS. 8A and 8B show plots of the results of the functional assay described in Example 4, below.
Figure 8B:
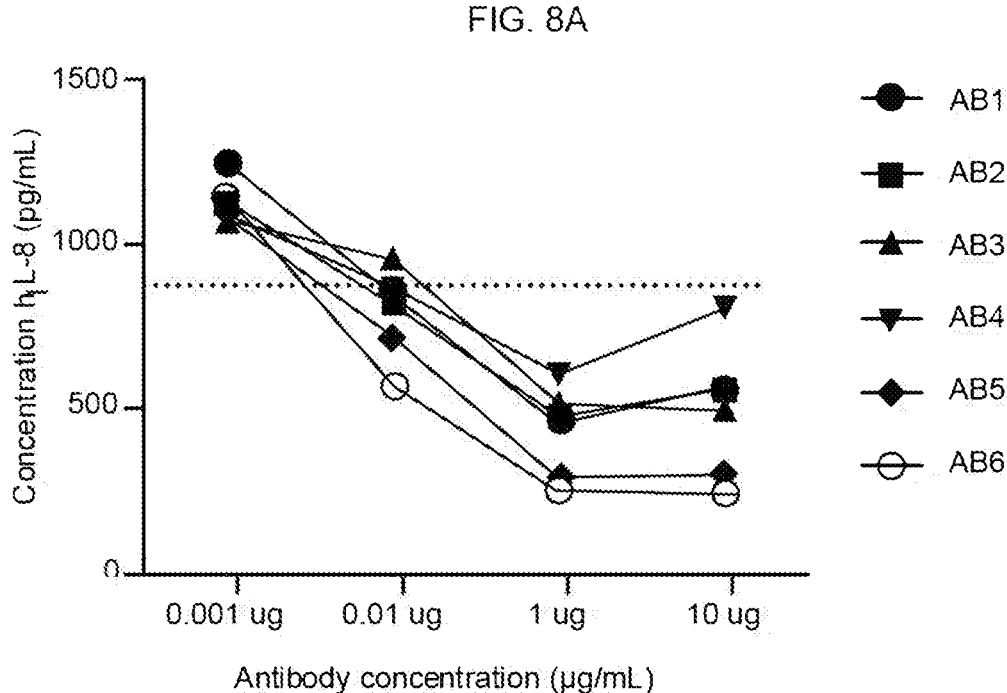
Figure 9:
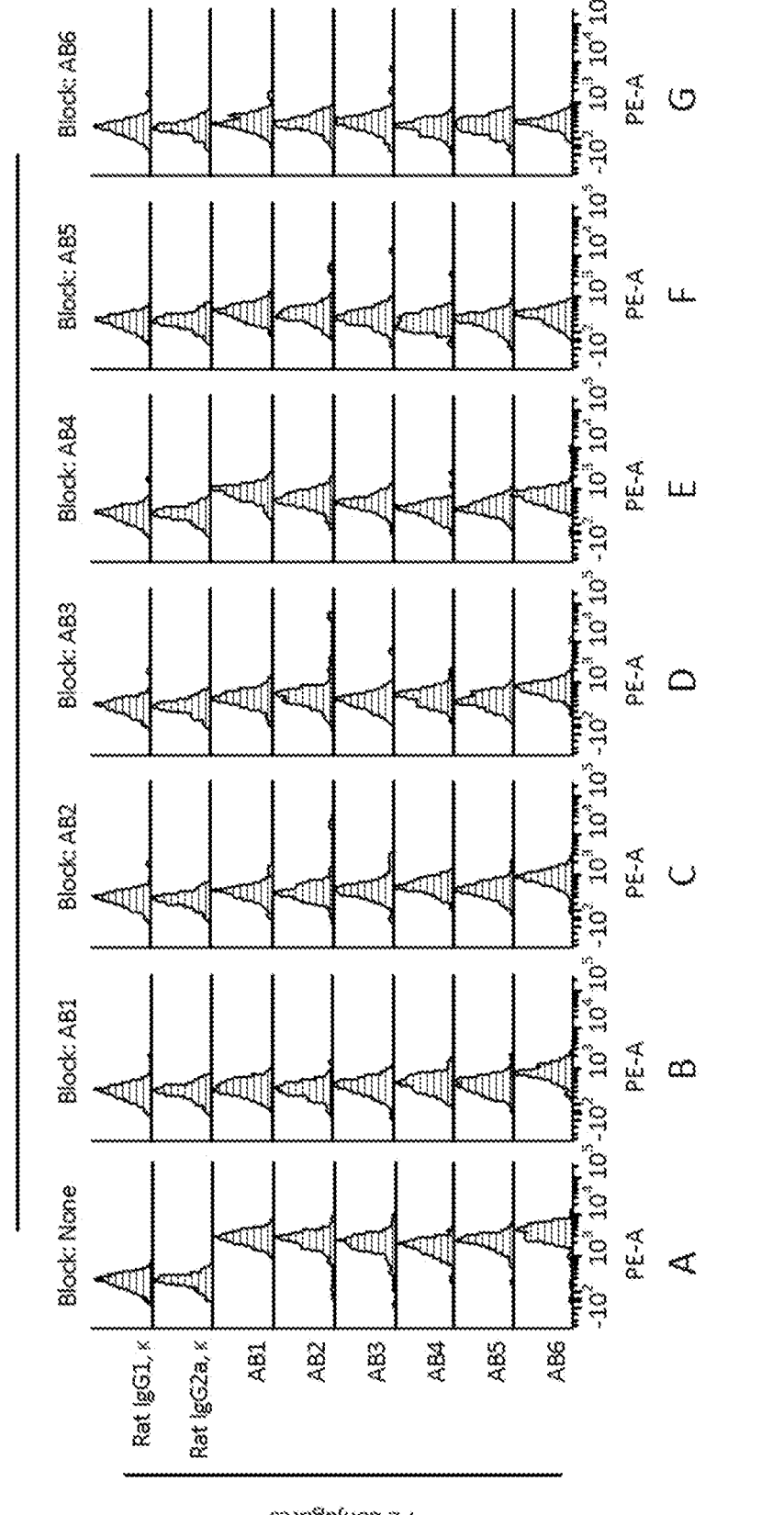
FIG. 9 shows results of a blocking assay described in Example 5. The top two rows show assay results for isotype control (Rat IgG1, κ; Rat IGG2a, κ). PE conjugated anti-TLR7 antibody (FIG. 9, panels A-G) used for each assay (i.e., AB1, AB2, AB3, AB4, AB5, AB6) is listed on the y-axis.

The amount of R848 induced human IL-8 antibody secreted by the cells was reduced inversely proportional to the concentration of TLR7 antibody present (FIG. 8, Panel A). Fold change in IL-8 secretion was calculated as the ratio of hIL-8 secreted in the presence of TLR7 antibody at the indicated concentration to hIL-8 secreted in the presence of an isotype control antibody at 10 µg/mL.

Example 5: Blocking Assay

This example describes a blocking assay performed using anti-TLR7 antibodies described herein.

PBMC Isolation

Human peripheral blood mononuclear cells (PBMCs) were isolated through a gradient of Ficoll-Paque PLUS (GE Healthcare) according to manufacturer instructions.

Blocking Assay

For blocking studies, PBMCs were stained with CD3, CD19, and CD304, fixed, permeabilized, and then incubated with 5 µg purified antibody (Rat IgG2a, Rat IgG1, AB1, AB2, AB3, AB4, AB5 or AB6) for 30 minutes in the dark. Rat IgG2a, Rat IgG1, AB1, AB2, AB3, AB4, AB5, and AB6 were used as blocking agents. In certain instances, no blocking agents were used. Cells were then incubated with PE conjugated antibody or isotype control for 30 minutes. Cells were washed with 1× Permeabilization Buffer (Intracellular Staining Permeabilization Wash Buffer (BioLegend, cat. #421002)), acquired on a BD Cantoll and analyzed using FlowJo software.

Calculations for % Blocking

Percentage original MFI was calculated by dividing the MFI of samples blocked with isotype controls, AB1, AB2, AB3, AB4, AB5, or AB6 by the MFI without blocking. This value was subtracted from 100 to get a blocking percentage. The formula is shown below:

$$100 - (\frac{[MFI\ \text{blocking}]}{[MFI\ \text{no blocking}]} * 100)$$

Results

TABLE 6

| | Results | | |
|---|---|---|---|
| Purified Blocking AB | PE AB Conjugate | MFI | % Blocking |
| Rat IGg1 | AB1 | 2508 | N/A |
| | AB2 | 2169 | N/A |
| | AB3 | 2299 | N/A |
| | AB4 | 1446 | N/A |
| | AB5 | 1743 | N/A |
| Rat IGg2a | AB6 | 3532 | N/A |
| AB1 | AB1 | 320 | 86 |
| | AB2 | 291 | 86 |
| | AB3 | 352 | 81 |
| | AB4 | 438 | 72 |
| | AB5 | 382 | 80 |
| | AB6 | 734 | 78 |
| AB2 | AB1 | 353 | 85 |
| | AB2 | 435 | 79 |
| | AB3 | 404 | 79 |

TABLE 6-continued

| | Results | | |
|---|---|---|---|
| Purified Blocking AB | PE AB Conjugate | MFI | % Blocking |
| | AB4 | 533 | 65 |
| | AB5 | 421 | 78 |
| | AB6 | 804 | 76 |
| AB3 | AB1 | 415 | 82 |
| | AB2 | 617 | 71 |
| | AB3 | 356 | 81 |
| | AB4 | 410 | 73 |
| | AB5 | 341 | 82 |
| | AB6 | 714 | 79 |
| AB4 | AB1 | 805 | 65 |
| | AB2 | 592 | 72 |
| | AB3 | 474 | 75 |
| | AB4 | 306 | 80 |
| | AB5 | 365 | 81 |
| | AB6 | 687 | 79 |
| AB5 | AB1 | 458 | 80 |
| | AB2 | 432 | 80 |
| | AB3 | 391 | 79 |
| | AB4 | 274 | 82 |
| | AB5 | 274 | 86 |
| | AB6 | 366 | 89 |
| AB6 | AB1 | 340 | 85 |
| | AB2 | 345 | 84 |
| | AB3 | 354 | 81 |
| | AB4 | 246 | 84 |
| | AB5 | 282 | 85 |
| | AB6 | 330 | 90 |

Example 6: Examples of Sequences

Provided below are examples of amino acid sequences related to the technology described herein.

| mAb | CDRH1 (SEQ ID NO:) | CDRH2 (SEQ ID NO:) | CDRH3 (SEQ ID NO:) | CDRL1 (SEQ ID NO:) | CDRL2 (SEQ ID NO:) | CDRL3 (SEQ ID NO:) |
|---|---|---|---|---|---|---|
| AB1 | DYWMS (1) | DIKYDGSFI DYAPSLKN (6) | DLTTVVDG FAY (12) | RASQSLST SIH (19) | YASQPIS (24) | QQSYSSP YT (29) |
| AB2 | DYWMS (1) | DIKYDGTFI DYAPSLKN (7) | DLTTVVDG FAY (12) | RASQSLST SIH (19) | YASQPIS (24) | QQSYSSP YT (29) |
| AB3 | NYYMA (2) | SITNSGRT TYYRDSVK G (8) | EGGDLYY SNYNYVRFNLA AY (13) | LPSEDIYN (18) | YASNLQD (23) | LQDSDYPF T (28) |
| AB4 | DYYMA (3) | SISYEGSS THYGDSV KA (9) | HGGYPNW YFDF (14) | RASEDIYN ELA (17) | NANSLHT (22) | QQYYDYP WT (27) |
| AB5 | DYCVH (4) | YINPYSGY TNYNEKFK S (10) | GPYGGYS GDGFDY (15) | RASEDIYN VLA (16) | NANRLHN (20) | QQYYDYP NT (25) |
| AB6 | DYYIH (5) | FINPDSGY TNYNEKFK T (11) | GPYGGYS GDGFDY (15) | RASEDIYN VLA (16) | NANNLHT (21) | QQYYDYP HT (26) |

CDRH1

(SEQ ID NO: 30)

$X_1YX_2X_3X_4$ $X_1$=D or N
$X_2$=W, Y, or C
$X_3$=M, V, or I
$X_4$=S, A, or H

CDRH2

(SEQ ID NO: 31)

$X_1IX_2X_3X_4X_5X_6X_7X_8X_9YX_{10}X_{11}X_{12}X_{13}KKX_{14}$ $X_1$=D, S, Y, or F
$X_2$=K, T, S, or N
$X_3$=Y, N, or P
$X_4$=D, S, E, or Y
$X_5$=G or S
$X_6$=S, T, R, or G
$X_7$=F, T, S, or Y
$X_8$=I or T
$X_9$=D, Y, H, or N
$X_{10}$=A, R, G, or N
$X_{11}$=P, D, or E
$X_{12}$=S or K
$X_{13}$=L, V, or F
$X_{14}$=N, G, A, S, or T

CDRH3

(SEQ ID NO: 32)

$X_1X_2X_3X_4X_5X_6X_7X_8X_9X_{10}X_{11}X_{12}X_{13}X_{14}FX_{15}X_{16}$ $X_1$=D, E, H, or G
$X_2$=L, G, or P
$X_3$=T, G, or Y
$X_4$=no amino acid, T, D, or G
$X_5$=no amino acid, L, or G
$X_6$=no amino acid or Y
$X_7$=V, Y, or S
$X_8$=V, S, P, or G
$X_9$=D or N
$X_{10}$=G, Y, or W
$X_{11}$=no amino acid or N
$X_{12}$=no amino acid or Y
$X_{13}$=no amino acid or V
$X_{14}$=no amino acid, R, or Y
$X_{15}$=A or D
$X_{16}$=Y or F

CDRL1

(SEQ ID NO: 33)

$X_1X_2SX_3X_4X_5X_6X_7X_8X_9X_{10}$ $X_1$=R or L
$X_2$=A or P
$X_3$=E or Q
$X_4$=D or S
$X_5$=I or L
$X_6$=Y or S
$X_7$=N or T
$X_8$=V, E, N, or S
$X_9$=L or I
$X_{10}$=A or H

CDRL2

(SEQ ID NO: 34)

$X_1AX_2X_3X_4X_5X_6$ $X_1$=N or Y
$X_2$=N or S
$X_3$=R, N, S, or Q
$X_4$=L or P
$X_5$=H, Q, or I
$X_6$=N, T, D, or S

CDRL3

(SEQ ID NO: 35)

$X_1QX_2X_3X_4X_5PX_6T$ $X_1$=Q or L
$X_2$=Y, D, or S
$X_3$=Y or S
$X_4$=D or S
$X_5$=Y or S
$X_6$=N, H, W, F, or Y

| Clone Name | | SEQ ID NO |
|---|---|---|
| | Heavy chain variable region (HCVR) sequence | |
| AB1 | ELQLVESGGGLVKPGASLKLSCVASGFTFSD YWMSWVRQTPGKTMEWIGDIKYDGSFIDYAP SLKNRFTISRDNAKNTLYLQMSNVRSEDTAT YYCARDLTTVVDGFAYWGQGT LVTVSS | 36 |
| AB2 | ELQLVESGGGLVKPGASLKLSCVASGFTFSD YWMSWVRQTPGKTMEWIGDIKYDGTFIDYAP SLKNRFTISRDNAKNTLYLQMSNVRSEDTAT YYCARDLTTVVDGFAYWGHGT LVTVSS | 37 |
| AB3 | EVQLVESGGGLLQPGRSLKLSCAASGFTFTN YYMAWVRQAPTKGLEWVASITNSGRTTYYRD SVKGRFTISRDNAKSTLYLQMDSLRSEDTAT YYCTREGGDLYYSNYNYVRFAYWGQGT LVT VSS | 38 |
| AB4 | EVQLVESGGGLVQPGRSLKLSCAASGFTFRD YYMAWVRQAPKKGLEWVASISYEGSSTHYGD SVKARFTVSRDDAKSTLYLQMNSLRSEDTAT YYCGRHGGYPNWYFDFWGPGTMVTVSS | 39 |
| AB5 | QVNLLQSGAALVKPGASVKLSCKASGYTFTD YCVHWVKQSHGKSLEWIGYINPYSGYTNYNE KFKSKATLTVDTSTNTAYMELSRLTSDDSAT CYCTRGPYGGYSGDGFDYWGQGVMVTVSS | 40 |
| AB6 | QVNLLQSGAALVKPGASVKLSCKASGYTFTD YYIHWVKQSHVKSLEWFGFINPDSGYTNYNE KFKTKATLTVDKSTNTAYMELSRLTSEGSAT YYCTRGPYGGYSGDGFDYWGQGV MVTVSS | 41 |
| | Light chain variable region (LCVR) sequence | |
| AB1 | NIVLTQSPATLSVTPGESVSLSCRASQSLST SIHWYQQKPNESPRLLIRYASQPISGIPS R FSGSGSGTDFTLSINRVESEDFSIYYCQQSY SSPYTFGAGTKLELK | 42 |
| AB2 | NIVLTQSPATLSVTPGESVSLSCRASQSLST SIHWYQQMPNESPRLLIRYASQPISGIPS R FSGSGSGTDFTLSINRVESEDFSIYYCQQSY SSPYTFGAGTRLELK | 43 |

-continued

| Clone Name | | SEQ ID NO |
|---|---|---|
| AB3 | DIQMTQSPASLSASLGETVSIECLPSEDIYN NLAWYQQKPGKSPQLLIHYASNLQDGVPS R FSGSGSGTQYSLKIKSLESEDAATYFCLQDS DYPFTFGSGTKLEIK | 44 |
| AB4 | DIQMTQSPASLSASLGETVTIECRASEDIYN ELAWYQQKPGKSPQLLIYNANSLHTGVPS R FSGSGSGTQYSLKINSLQSEDVASYFCQQYY DYPWTFGGGTKLELK | 45 |
| AB5 | DIQMTQSPASLSASLGETVTIECRASEDIYN VLAWYQQKPGKSPQLLISNANRLHNGVPS R FSGSGSGTQYSLKINSLQSEDVASYFCQQYY DYPNTFGAGTKLELK | 46 |
| AB6 | DIQMTQSPASLSASLGETVTIECRASEDIYN VLAWYQQKPGKSPQLLISNANNLHTGVPS R FSGSESGTQYSLKINSLQSEDVASYFCQQYY DYPHTFGAGTKLELK | 47 |

Precursor Human TLR7 Protein Sequence (UniProtKB—
Q9NYK1 (TLR7_HUMAN)/NCBI Reference Sequence:
NP_057646.1) (SEQ ID NO:48)

```
   1  mvfpmwtlkr qililfniil iskllgarwf pktlpcdvtl dvpknhvivd ctdkhlteip
  61  ggiptnttnl tltinhipdi spasfhrldh lveidfrcnc vpiplgsknn mcikrlqikp
 121  rsfsgltylk slyldgnqll eipqglppsl qllsleanni fsirkenlte lanieilylg
 181  qncyyrnpcy vsysiekdaf lnltklkvls lkdnnvtavp tvlpstltel ylynnmiaki
 241  qeddfnnlnq lqildlsgnc prcynapfpc apcknnsplq ipvnafdalt elkvlrlhsn
 301  slqhvpprwf kninklqeld lsqnflakei gdakflhflp sliqldlsfn felqvyrasm
 361  nlsqafsslk slkilrirgy vfkelksfnl splhnlqnle vldlgtnfik ianlsmfkqf
 421  krlkvidlsv nkispsgdss evgfcsnart svesyepqvl eqlhyfrydk yarscrfknk
 481  easfmsvnes cykygqtldl sknsiffvks sdfqhlsflk clnlsgnlis qtlngsefqp
 541  laelryldfs nnrldllhst afeelhklev ldissnshyf qsegithmln ftknlkvlqk
 601  lmmndndiss stsrtmeses lrtlefrgnh ldvlwregdn rylqlfknll kleeldiskn
 661  slsflpsgvf dgmppnlknl slaknglksf swkklqclkn letldlshnq lttvperlsn
 721  csrslknlil knnqirsltk yflqdafqlr yldlssnkiq miqktsfpen vlnnlkmlll
 781  hhnrflctcd avwfvwwvnh tevtipylat dvtcvgpgah kgqsvisldl ytceldltnl
 841  ilfslsisvs lflmvmmtas hlyfwdvwyi yhfckakikg yqrlispdcc ydafivydtk
 901  dpavtewvla elvakledpr ekhfnlclee rdwlpgqpvl enlsqsiqls kktvfvmtdk
 961  yaktenfkia fylshqrlmd ekvdviilif lekpfqkskf lqlrkrlcgs svlewptnpq
1021  ahpyfwqclk nalatdnhva ysqvfketv
```

Human TLR7 Signal Sequence (SEQ ID NO: 49)

```
mvfpmwtlkr qililfniil iskllg
```

Mature Human TLR7 Protein Sequence (SEQ ID NO: 50)

```
arwf pktlpcdvtl dvpknhvivd ctdkhlteip
ggiptnttnl tltinhipdi spasfhrldh lveidfrcnc
```

-continued

```
vpiplgsknn mcikrlqikp rsfsgltylk slyldgnqll eipqglppsl qllsleanni fsirkenlte lanieilylg qncyyrnpcy vsysiekdaf lnltklkvls lkdnnvtavp tvlpstltel ylynnmiaki qeddfnnlnq lqildlsgnc prcynapfpc apcknnsplq ipvnafdalt elkvlrlhsn slqhvpprwf kninklqeld lsqnflakei gdakflhflp sliqldlsfn felqvyrasm nlsqafsslk slkilrirgy vfkelksfnl splhnlqnle vldlgtnfik ianlsmfkqf krlkvidlsv nkispsgdss evgfcsnart svesyepqvl eqlhyfrydk yarscrfknk easfmsvnes cykygqtldl sknsiffvks sdfqhlsflk clnlsgnlis qtlngsefqp laelryldfs nnrldllhst afeelhklev ldissnshyf qsegithmln ftknlkvlqk lmmndndiss stsrtmeses lrtlefrgnh ldvlwregdn rylqlfknll kleeldiskn
```

-continued

```
slsflpsgvf dgmppnlknl slaknglksf swkklqclkn letldlshnq lttvperlsn csrslknlil knnqirsltk yflqdafqlr yldlssnkiq miqktsfpen vlnnlkmlll hhnrflctcd avwfvwwvnh tevtipylat dvtcvgpgah kgqsvisldl ytceldltnl ilfslsisvs lflmvmmtas hlyfwdvwyi yhfckakikg yqrlispdcc ydafivydtk
```

-continued

```
dpavtewvla elvakledpr ekhfnlclee rdwlpgqpvl enlsqsiqls kktvfvmtdk yaktenfkia fylshqrlmd ekvdviilif lekpfqkskf lqlrkrlcgs svlewptnpq ahpyfwqclk nalatdnhva ysqvfketv
```

Example 7: Examples of Embodiments

The examples set forth below illustrate certain embodiments and do not limit the technology.

A1. An anti-TLR7 agent that binds Toll-like Receptor 7 (TLR7) under laboratory or physiological conditions, wherein the agent comprises at least one immunoglobulin heavy chain variable domain and/or at least one immunoglobulin light chain variable domain, wherein:

a) each immunoglobulin heavy chain variable domain of the anti-TLR7 agent comprises first, second, and third heavy chain complementarity determining regions (CDRs), wherein the first heavy chain CDR (CDRH1) comprises an amino acid sequence that is at least 80 percent identical (e.g., 85, 87, 90, 91, 92, 93, 94, 95, 96, 97, 98, 99, or 100 percent identical) to the amino acid sequence $X_1YX_2X_3X_4$ (SEQ ID NO:30), wherein $X_1$ is D or N, $X_2$ is W, Y, or C, $X_3$ is M, V, or I, and $X_4$ is S, A, or H;

the second heavy chain CDR (CDRH2) comprises an amino acid sequence that is at least 80 percent identical (e.g., 85, 87, 90, 91, 92, 93, 94, 95, 96, 97, 98, 99, or 100 percent identical) to the amino acid sequence $X_1IX_2X_3X_4X_5X_6X_7X_8X_9YX_{10}X_{11}X_{12}X_{13}KX_{14}$ (SEQ ID NO:31), wherein $X_1$ is D, S, Y, or F, $X_2$ is K, T, S, or N, $X_3$ is Y, N, or P, $X_4$ is D, S, E, or Y, $X_5$ is G or S, $X_6$ is S, T, R, or G, $X_7$ is F, T, S, or Y, $X_8$ is I or T, $X_9$ is D, Y, H, or N, $X_{10}$ is A, R, G, or N, $X_{11}$ is P, D, or E, $X_{12}$ is S or K, $X_{13}$ is L, V, or F, and $X_{14}$ is N, G, A, S, or T; and the third heavy chain CDR (CDRH3) comprises an amino acid sequence that is at least 80 percent identical (e.g., 85, 87, 90, 91, 92, 93, 94, 95, 96, 97, 98, 99, or 100 percent identical) to the amino acid sequence $X_1X_2X_3X_4X_5X_6X_7X_8X_9X_{10}X_{11}X_{12}X_{13}X_{14}FX_{15}X_{16}$ (SEQ ID NO:32), wherein $X_1$ is D, E, H, or G, $X_2$ is L, G, or P, $X_3$ is T, G, or Y, $X_4$ is no amino acid, T, D, or G, $X_5$ is no amino acid, L or G, $X_6$ is no amino acid or Y, $X_7$ is V, Y, or S, $X_8$ is V, S, P, or G, $X_9$ is D or N, $X_{10}$ is C, Y, or W, $X_{11}$ is no amino acid or N, $X_{12}$ is no amino acid or Y, $X_{13}$ is no amino acid or V, $X_{14}$ is no amino acid, R or Y, $X_{15}$ is A or D, and $X_{16}$ is Y or F; and/or b) each immunoglobulin light chain variable domain of the anti-TLR7 agent comprises first, second, and third light chain CDRs, wherein the first light chain CDR (CDRL1) comprises an amino acid sequence that is at least 80 percent identical (e.g., 85, 87, 90, 91, 92, 93, 94, 95, 96, 97, 98, 99, or 100 percent identical) to the amino acid sequence $X_1X_2SX_3X_4X_5X_6X_7X_8X_9X_{10}$ (SEQ ID NO:33), wherein $X_1$ is R or L, $X_2$ is A or P, $X_3$ is E or Q, $X_4$ is D or S, $X_5$ is I or L, $X_6$ is Y or S, $X_7$ is N or T, $X_8$ is V, E, N, or S, $X_9$ is L or I, and $X_{10}$ is A or H;

the second light chain CDR (CDRL2) comprises an amino acid sequence that is at least 80 percent identical (e.g., 85, 87, 90, 91, 92, 93, 94, 95, 96, 97, 98, 99, or 100 percent identical) to the amino acid sequence $X_1AX_2X_3X_4X_5X_6$ (SEQ ID NO:34), wherein $X_1$ is N or Y, $X_2$ is N or S, $X_3$ is R, N, S, or Q, $X_4$ is L or P, $X_5$ is H, Q, or I, and $X_6$ is N, T, D, or S; and the third light chain CDR (CDRL3) comprises an amino acid sequence that is at least 80 percent identical (e.g., 85, 87, 90, 91, 92, 93, 94, 95, 96, 97, 98, 99, or 100 percent identical) to the amino acid sequence $X_1QX_2X_3X_4X_5PX_6T$ (SEQ ID NO:35), wherein $X_1$ is Q or L, $X_2$ is Y, D, or S, $X_3$ is Y or S, $X_4$ is D or S, $X_5$ is Y or S, and $X_6$ is N, H, W, F, or Y.

A2. The anti-TLR7 agent of embodiment A1, wherein the CDRH1 comprises an amino acid sequence that is at least 85 percent identical to the amino acid sequence of SEQ ID NO:30.

A3. The anti-TLR7 agent of embodiment A1, wherein the CDRH1 comprises an amino acid sequence that is at least 90 percent identical to the amino acid sequence of SEQ ID NO:30.

A4. The anti-TLR7 agent of embodiment A1, wherein the CDRH1 comprises an amino acid sequence that is at least 95 percent identical to the amino acid sequence of SEQ ID NO:30.

A5. The anti-TLR7 agent of embodiment A1, wherein the CDRH1 comprises an amino acid sequence that is 100 percent identical to the amino acid sequence of SEQ ID NO:30.

A6. The anti-TLR7 agent of any one of embodiments A1 to A5, wherein the CDRH2 comprises an amino acid sequence that is at least 85 percent identical to the amino acid sequence of SEQ ID NO:31.

A7. The anti-TLR7 agent of any one of embodiments A1 to A5, wherein the CDRH2 comprises an amino acid sequence that is at least 90 percent identical to the amino acid sequence of SEQ ID NO:31.

A8. The anti-TLR7 agent of any one of embodiments A1 to A5, wherein the CDRH2 comprises an amino acid sequence that is at least 95 percent identical to the amino acid sequence of SEQ ID NO:31.

A9. The anti-TLR7 agent of any one of embodiments A1 to A5, wherein the CDRH2 comprises an amino acid sequence that is 100 percent identical to the amino acid sequence of SEQ ID NO:31.

A10. The anti-TLR7 agent of any one of embodiments A1 to A9, wherein the CDRH3 comprises an amino acid sequence that is at least 85 percent identical to the amino acid sequence of SEQ ID NO:32.

A11. The anti-TLR7 agent of any one of embodiments A1 to A9, wherein the CDRH3 comprises an amino acid sequence that is at least 90 percent identical to the amino acid sequence of SEQ ID NO:32.

A12. The anti-TLR7 agent of any one of embodiments A1 to A9, wherein the CDRH3 comprises an amino acid sequence that is at least 95 percent identical to the amino acid sequence of SEQ ID NO:32.

A13. The anti-TLR7 agent of any one of embodiments A1 to A9, wherein the CDRH3 comprises an amino acid sequence that is 100 percent identical to the amino acid sequence of SEQ ID NO:32.

A14. The anti-TLR7 agent of any one of embodiments A1 to A13, wherein the CDRL1 comprises an amino acid sequence that is at least 85 percent identical to the amino acid sequence of SEQ ID NO:33.

A15. The anti-TLR7 agent of any one of embodiments A1 to A13, wherein the CDRL1 comprises an amino acid sequence that is at least 90 percent identical to the amino acid sequence of SEQ ID NO:33.

A16. The anti-TLR7 agent of any one of embodiments A1 to A13, wherein the CDRL1 comprises an amino acid sequence that is at least 95 percent identical to the amino acid sequence of SEQ ID NO:33.

A17. The anti-TLR7 agent of any one of embodiments A1 to A13, wherein the CDRL1 comprises an amino acid sequence that is 100 percent identical to the amino acid sequence of SEQ ID NO:33.

A18. The anti-TLR7 agent of any one of embodiments A1 to A17, wherein the CDRL2 comprises an amino acid sequence that is at least 85 percent identical to the amino acid sequence of SEQ ID NO:34.

A19. The anti-TLR7 agent of any one of embodiments A1 to A17, wherein the CDRL2 comprises an amino acid sequence that is at least 90 percent identical to the amino acid sequence of SEQ ID NO:34.

A20. The anti-TLR7 agent of any one of embodiments A1 to A17, wherein the CDRL2 comprises an amino acid sequence that is at least 95 percent identical to the amino acid sequence of SEQ ID NO:34.

A21. The anti-TLR7 agent of any one of embodiments A1 to A17, wherein the CDRL2 comprises an amino acid sequence that is 100 percent identical to the amino acid sequence of SEQ ID NO:34.

A22. The anti-TLR7 agent of any one of embodiments A1 to A21, wherein the CDRL3 comprises an amino acid sequence that is at least 85 percent identical to the amino acid sequence of SEQ ID NO:35.

A23. The anti-TLR7 agent of any one of embodiments A1 to A21, wherein the CDRL3 comprises an amino acid sequence that is at least 90 percent identical to the amino acid sequence of SEQ ID NO:35.

A24. The anti-TLR7 agent of any one of embodiments A1 to A21, wherein the CDRL3 comprises an amino acid sequence that is at least 95 percent identical to the amino acid sequence of SEQ ID NO:35.

A25. The anti-TLR7 agent of any one of embodiments A1 to A21, wherein the CDRL3 comprises an amino acid sequence that is 100 percent identical to the amino acid sequence of SEQ ID NO:35.

A26. The anti-TLR7 agent of any one of embodiments A1 to A25, wherein the CDRH1 comprises an amino acid sequence chosen from DYWMS (SEQ ID NO: 1), NYYMA (SEQ ID NO: 2), DYYMA (SEQ ID NO: 3), DYCVH (SEQ ID NO: 4), and DYYIH (SEQ ID NO: 5).

A27. The anti-TLR7 agent of any one of embodiments A1 to A26, wherein the CDRH2 comprises an amino acid sequence chosen from DIKYDGSFIDYAPSLKN (SEQ ID NO: 6), DIKYDGTFIDYAPSLKN (SEQ ID NO: 7), SITNSGRTTYYRDSVKG (SEQ ID NO: 8), SISYEGSSTHYGDSVKA (SEQ ID NO: 9), YINPYSGYTNYNEKFKS (SEQ ID NO: 10), and FINPDSGYTNYNEKFKT (SEQ ID NO: 11).

A28. The anti-TLR7 agent of any one of embodiments A1 to A27, wherein the CDRH3 comprises an amino acid sequence chosen from DLTTVVDGFAY (SEQ ID NO:12), EGGDLYYSNYNYVRFAY (SEQ ID NO:13), HGGYPNWYFDF (SEQ ID NO:14), and GPYG-GYSGDGFDY (SEQ ID NO:15).

A29. The anti-TLR7 agent of any one of embodiments A1 to A28, wherein the CDRL1 comprises an amino acid sequence chosen from RASEDIYNVLA (SEQ ID NO:16), RASEDIYNELA (SEQ ID NO:17), LPSEDIYNNLA (SEQ ID NO:18), and RASQSLSTSIH (SEQ ID NO:19).

A30. The anti-TLR7 agent of any one of embodiments A1 to A29, wherein the CDRL2 comprises an amino acid sequence chosen from NANRLHN (SEQ ID NO:20), NANNLHT (SEQ ID NO:21), NANSLHT (SEQ ID NO:22), YASNLQD (SEQ ID NO:23), and YASQPIS (SEQ ID NO:24).

A31. The anti-TLR7 agent of any one of embodiments A1 to A30, wherein the CDRL3 comprises an amino acid sequence chosen from QQYYDYPNT (SEQ ID NO:25), QQYYDYPHT (SEQ ID NO:26), QQYYDYPWT (SEQ ID NO:27), LQDSDYPFT (SEQ ID NO:28), and QQSYS-SPYT (SEQ ID NO:29).

A32. The anti-TLR7 agent of any one of embodiments A1 to A31, which comprises two immunoglobulin heavy chain variable domains and two immunoglobulin light chain variable domains.

A33. The anti-TLR7 agent of embodiment A32, wherein the two immunoglobulin heavy chain variable domains each comprise a set of CDRH1, CDRH2, and CDRH3 amino acid sequences.

A34. The anti-TLR7 agent of embodiment A32 or A33, wherein the two immunoglobulin light chain variable domains each comprise a set of CDRL1, CDRL2, and CDRL3 amino acid sequences.

A35. The anti-TLR7 agent of any one of embodiments A1 to A34, wherein each immunoglobulin heavy chain variable domain comprises a set of CDRH1, CDRH2, and CDRH3 amino acid sequences and each immunoglobulin light chain variable domain comprises a set of CDRL1, CDRL2, and CDRL3 amino acid sequences chosen from sets 1-6:

| set | CDRH1 (SEQ ID NO:) | CDRH2 (SEQ ID NO:) | CDRH3 (SEQ ID NO:) | CDRL1 (SEQ ID NO:) | CDRL2 (SEQ ID NO:) | CDRL3 (SEQ ID NO:) |
|---|---|---|---|---|---|---|
| 1 | DYWMS (1) | DIKYDGSFIDYA PSLKN (6) | DLTTVVDGFAY (12) | RASQSLSTSIH (19) | YASQPIS (24) | QQSYSSPYT (29) |
| 2 | DYWMS (1) | DIKYDGTFIDYA PSLKN (7) | DLTTVVDGFAY (12) | RASQSLSTSIH (19) | YASQPIS (24) | QQSYSSPYT (29) |
| 3 | NYYMA (2) | SITNSGRTTYY RDSVKG (8) | EGGDLYYSNYN YVRFAY (13) | LPSEDIYNNLA (18) | YASNLQD (23) | LQDSDYPFT (28) |
| 4 | DYYMA (3) | SISYEGSSTHY GDSVKA (9) | HGGYPNWYFD F (14) | RASEDIYNELA (17) | NANSLHT (22) | QQYYDYPWT (27) |
| 5 | DYCVH (4) | YINPYSGYTNY NEKFKS (10) | GPYGGYSGDG FDY (15) | RASEDIYNVLA (16) | NANRLHN (20) | QQYYDYPNT (25) |
| 6 | DYYIH (5) | FINPDSGYTNY NEKFKT (11) | GPYGGYSGDG FDY (15) | RASEDIYNVLA (16) | NANNLHT (21) | QQYYDYPHT (26) |

A36. The anti-TLR7 agent of embodiment A35, wherein all CDR sequences are from the same set.

A37. The anti-TLR7 agent of any one of embodiments A1 to A36, wherein the agent is isolated.

A38. The anti-TLR7 agent of any one of embodiments A1 to A37, wherein the agent is non-naturally occurring.

A39. The anti-TLR7 agent of any one of embodiments A1 to A38, wherein the agent is an antibody, or antigen-binding fragment thereof.

A40. The anti-TLR7 agent of any one of embodiments A1 to A38, wherein the agent is an antibody, or derivative thereof.

A41. The anti-TLR7 agent of any one of embodiments A1 to A40, wherein the agent is a humanized antibody, or an antigen binding fragment thereof.

A42. The anti-TLR7 agent of any one of embodiments A1 to A40, wherein the agent is a derivative of a humanized antibody that binds TLR7.

A43. The anti-TLR7 agent of any one of embodiments A1 to A42, wherein the agent comprises a detectable marker or label.

A44. The anti-TLR7 agent of any one of embodiments A1 to A43, wherein the agent is conjugated to a detectable marker or label.

A45. The anti-TLR7 agent of any one of embodiments A1 to A44, wherein the agent is non-diffusively immobilized on a solid support.

A46. A diagnostic reagent comprising the anti-TLR7 agent of any one of embodiments A1 to A45.

A47. A kit comprising the anti-TLR7 agent of any one of embodiments A1 to A45 or the diagnostic reagent of embodiment A46.

A48. A diagnostic kit configured to detect Toll-like Receptor 7 (TLR7) in a biological sample, wherein the kit comprises the anti-TLR7 agent of any one of embodiments A1 to A45 or the diagnostic reagent of embodiment A46.

A49. An isolated nucleic acid molecule comprising a nucleotide sequence that encodes an immunoglobulin heavy chain variable domain of the anti-TLR7 agent of any one of embodiments A1 to A45.

A50. An isolated nucleic acid molecule comprising a nucleotide sequence that encodes an immunoglobulin light chain variable domain of the anti-TLR7 agent of any one of embodiments A1 to A45.

A51. A recombinant expression vector comprising a first expression cassette and a second expression cassette, wherein the first expression cassette comprises a promoter and a nucleic acid molecule comprising a nucleotide sequence that encodes an immunoglobulin heavy chain variable domain of the anti-TLR7 agent of any one of embodiments A1 to A45, and the second expression cassette comprises a promoter and a nucleic acid molecule comprising a nucleotide sequence that encodes an immunoglobulin light chain variable domain of the anti-TLR7 agent of any one of embodiments A1 to A45.

A52. A recombinant host cell transfected with the recombinant expression vector of embodiment A51.

A53. A method of detecting TLR7, comprising contacting a sample known or suspected to contain TLR7 with the anti-TLR7 agent of any one of embodiments A1 to A45, and, if the sample contains TLR7, detecting TLR7: anti-TLR7 complexes.

B1. A first anti-TLR7 agent that binds Toll-like Receptor 7 (TLR7) under laboratory or physiological conditions, wherein the first agent competitively binds, or is capable of competitively binding, with a second anti-TLR7 agent, which the second agent is the anti-TLR7 agent of any one of embodiments A1 to A36.

B2. A first anti-TLR7 agent that binds Toll-like Receptor 7 (TLR7) under laboratory or physiological conditions, wherein the first agent binds to, or is capable of binding to, the same epitope as a second anti-TLR7 agent, which the second agent is the anti-TLR7 agent of any one of embodiments A1 to A36.

B3. The first anti-TLR7 agent of embodiment B1 or B2, wherein the first agent and/or second agent is isolated.

B4. The first anti-TLR7 agent of any one of embodiments B1 to B3, wherein the first agent and/or second agent is non-naturally occurring.

B5. The first anti-TLR7 agent of any one of embodiments B1 to B4, wherein the first agent and/or second agent is an antibody, or antigen-binding fragment thereof.

B6. The first anti-TLR7 agent of any one of embodiments B1 to B4, wherein the first agent and/or second agent is an antibody, or derivative thereof.

B7. The first anti-TLR7 agent of any one of embodiments B1 to B6, wherein the first agent and/or second agent is a humanized antibody, or an antigen binding fragment thereof.

B8. The first anti-TLR7 agent of any one of embodiments B1 to B6, wherein the first agent and/or second agent is a derivative of a humanized antibody that binds TLR7.

B9. The first anti-TLR7 agent of any one of embodiments B1 to B8, comprising a detectable marker or label.

B10. The first anti-TLR7 agent of any one of embodiments B1 to B9, wherein the first agent is conjugated to a detectable marker or label.

B11. The first anti-TLR7 agent of any one of embodiments B1 to B10, wherein the first agent is non-diffusively immobilized on a solid support.

B12. A diagnostic reagent comprising the first anti-TLR7 agent of any one of embodiments B1 to B11.

B13. A kit comprising the first anti-TLR7 agent of any one of embodiments B1 to B11 or the diagnostic reagent of embodiment B12.

B14. A diagnostic kit configured to detect Toll-like Receptor 7 (TLR7) in a biological sample, wherein the kit comprises the first anti-TLR7 agent of any one of embodiments B1 to B11 or the diagnostic reagent of embodiment B12.

B15. An isolated nucleic acid molecule comprising a nucleotide sequence that encodes an immunoglobulin heavy chain variable domain of the first anti-TLR7 agent of any one of embodiments B1 to B11.

B16. An isolated nucleic acid molecule comprising a nucleotide sequence that encodes an immunoglobulin light chain variable domain of the first anti-TLR7 agent of any one of embodiments B1 to B11.

B17. A recombinant expression vector comprising a first expression cassette and a second expression cassette, wherein the first expression cassette comprises a promoter and a nucleic acid molecule comprising a nucleotide sequence that encodes an immunoglobulin heavy chain variable domain of the first anti-TLR7 agent of any one of embodiments B1 to B11, and the second expression cassette comprises a promoter and a nucleic acid molecule comprising a nucleotide sequence that encodes an immunoglobulin light chain variable domain of the first anti-TLR7 agent of any one of embodiments B1 to B11.

B18. A recombinant host cell transfected with the recombinant expression vector of embodiment B17.

B19. A method of detecting TLR7, comprising contacting a sample known or suspected to contain TLR7 with the first anti-TLR7 agent of any one of embodiments B1 to B11, and, if the sample contains TLR7, detecting TLR7: anti-TLR7 complexes.

C1. An anti-TLR7 agent for detecting TLR7 in a heterogeneous population of immune cells, wherein TLR7 is detected at a significant level in plasmacytoid dendritic cells, monocytes and/or B cells in the population, and TLR7 is not significantly detected in other immune cells in the population.

C2. The anti-TLR7 agent of embodiment C1, wherein the anti-TLR7 agent comprises at least one immunoglobulin heavy chain variable domain and at least one immunoglobulin light chain variable domain, wherein:

i) each immunoglobulin heavy chain variable domain of the anti-TLR7 agent comprises first, second, and third heavy chain complementarity determining regions (CDRs); and ii) each immunoglobulin light chain variable domain of the anti-TLR7 agent comprises first, second, and third light chain CDRs.

C3. The anti-TLR7 agent of embodiment C2, wherein the first heavy chain CDR (CDRH1) comprises an amino acid sequence that is at least 80 percent identical (e.g., 85, 87, 90, 91, 92, 93, 94, 95, 96, 97, 98, 99, or 100 percent identical) to the amino acid sequence $X_1YX_2X_3X_4$ (SEQ ID NO:30), wherein $X_1$ is D or N,
$X_2$ is W, Y, or C, $X_3$ is M, V, or I, and
$X_4$ is S, A, or H.

C4. The anti-TLR7 agent of embodiment C2 or C3, wherein the second heavy chain CDR (CDRH2) comprises an amino acid sequence that is at least 80 percent identical (e.g., 85, 87, 90, 91, 92, 93, 94, 95, 96, 97, 98, 99, or 100 percent identical) to the amino acid sequence $X_1IX_2X_3X_4X_5X_6X_7X_8X_9YX_{10}X_{11}X_{12}X_{13}KX_{14}$ (SEQ ID NO:31), wherein $X_1$ is D, S, Y, or F,
$X_2$ is K, T, S, or N,
$X_3$ is Y, N, or P,
$X_4$ is D, S, E, or Y,
$X_5$ is G or S,
$X_6$ is S, T, R, or G,
$X_7$ is F, T, S, or Y,
$X_8$ is I or T,
$X_9$ is D, Y, H, or N,
$X_{10}$ is A, R, G, or N,
$X_{11}$ is P, D, or E,
$X_{12}$ is S or K,
$X_{13}$ is L, V, or F, and
$X_{14}$ is N, G, A, S, or T.

C5. The anti-TLR7 agent of embodiment C2, C3, or C4, wherein the third heavy chain CDR (CDRH3) comprises an amino acid sequence that is at least 80 percent identical (e.g., 85, 87, 90, 91, 92, 93, 94, 95, 96, 97, 98, 99, or 100 percent identical) to the amino acid sequence $X_1X_2X_3X_4X_5X_6X_7X_8X_9X_{10}X_{11}X_{12}X_{13}X_{14}FX_{15}X_{16}$ (SEQ ID NO:32), wherein $X_1$ is D, E, H, or G,
$X_2$ is L, G, or P,
$X_3$ is T, G, or Y,
$X_4$ is no amino acid, T, D, or G,
$X_5$ is no amino acid, L or G,
$X_6$ is no amino acid or Y,
$X_7$ is V, Y, or S,
$X_8$ is V, S, P, or G,
$X_9$ is D or N,
$X_{10}$ is G, Y, or W,
$X_{11}$ is no amino acid or N,
$X_{12}$ is no amino acid or Y,
$X_{13}$ is no amino acid or V,
$X_{14}$ is no amino acid, R or Y,
$X_{15}$ is A or D, and
$X_{16}$ is Y or F.

C6. The anti-TLR7 agent of any one of embodiments C2 to C5, wherein the first light chain CDR (CDRL1) comprises an amino acid sequence that is at least 80 percent identical (e.g., 85, 87, 90, 91, 92, 93, 94, 95, 96, 97, 98, 99, or 100 percent identical) to the amino acid sequence $X_1X_2SX_3X_4X_5X_6X_7X_8X_9X_{10}$ (SEQ ID NO:33), wherein $X_1$ is R or L,
$X_2$ is A or P,
$X_3$ is E or Q,
$X_4$ is D or S,
$X_5$ is I or L,
$X_6$ is Y or S,
$X_7$ is N or T,
$X_8$ is V, E, N, or S,
$X_9$ is L or I, and
$X_{10}$ is A or H.

C7. The anti-TLR7 agent of any one of embodiments C2 to C6, wherein the second light chain CDR (CDRL2) comprises an amino acid sequence that is at least 80 percent identical (e.g., 85, 87, 90, 91, 92, 93, 94, 95, 96, 97, 98, 99, or 100 percent identical) to the amino acid sequence $X_1AX_2X_3X_4X_5X_6$ (SEQ ID NO:34), wherein X₁ is N or Y, $X_1$ is N or Y, $X_2$ is N or S, $X_3$ is R, N, S, or Q, $X_4$ is L or P, $X_5$ is H, Q, or I, and $X_6$ is N, T, D, or S.

C8. The anti-TLR7 agent of any one of embodiments C2 to C7, wherein the third light chain CDR (CDRL3) comprises an amino acid sequence that is at least 80 percent identical (e.g., 85, 87, 90, 91, 92, 93, 94, 95, 96, 97, 98, 99, or 100 percent identical) to the amino acid sequence $X_1QX_2X_3X_4X_5PX_6T$ (SEQ ID NO:35), wherein $X_1$ is Q or L, $X_2$ is Y, D, or S, $X_3$ is Y or S, $X_4$ is D or S, $X_5$ is Y or S, and $X_6$ is N, H, W, F, or Y.

C9. The anti-TLR7 agent of any one of embodiments C2 to C8, wherein the CDRH1 comprises an amino acid sequence that is at least 85 percent identical to the amino acid sequence of SEQ ID NO:30.

C10. The anti-TLR7 agent of any one of embodiments C2 to C8, wherein the CDRH1 comprises an amino acid sequence that is at least 90 percent identical to the amino acid sequence of SEQ ID NO:30.

C11. The anti-TLR7 agent of any one of embodiments C2 to C8, wherein the CDRH1 comprises an amino acid sequence that is at least 95 percent identical to the amino acid sequence of SEQ ID NO:30.

C12. The anti-TLR7 agent of any one of embodiments C2 to C8, wherein the CDRH1 comprises an amino acid sequence that is 100 percent identical to the amino acid sequence of SEQ ID NO:30.

C13. The anti-TLR7 agent of any one of embodiments C2 to C12, wherein the CDRH2 comprises an amino acid sequence that is at least 85 percent identical to the amino acid sequence of SEQ ID NO:31.

C14. The anti-TLR7 agent of any one of embodiments C2 to C12, wherein the CDRH2 comprises an amino acid sequence that is at least 90 percent identical to the amino acid sequence of SEQ ID NO:31.

C15. The anti-TLR7 agent of any one of embodiments C2 to C12, wherein the CDRH2 comprises an amino acid sequence that is at least 95 percent identical to the amino acid sequence of SEQ ID NO:31.

C16. The anti-TLR7 agent of any one of embodiments C2 to C12, wherein the CDRH2 comprises an amino acid sequence that is 100 percent identical to the amino acid sequence of SEQ ID NO:31.

C17. The anti-TLR7 agent of any one of embodiments C2 to C16, wherein the CDRH3 comprises an amino acid sequence that is at least 85 percent identical to the amino acid sequence of SEQ ID NO:32.

C18. The anti-TLR7 agent of any one of embodiments C2 to C16, wherein the CDRH3 comprises an amino acid sequence that is at least 90 percent identical to the amino acid sequence of SEQ ID NO:32.

C19. The anti-TLR7 agent of any one of embodiments C2 to C16, wherein the CDRH3 comprises an amino acid sequence that is at least 95 percent identical to the amino acid sequence of SEQ ID NO:32.

C20. The anti-TLR7 agent of any one of embodiments C2 to C16, wherein the CDRH3 comprises an amino acid sequence that is 100 percent identical to the amino acid sequence of SEQ ID NO:32.

C21. The anti-TLR7 agent of any one of embodiments C2 to C20, wherein the CDRL1 comprises an amino acid sequence that is at least 85 percent identical to the amino acid sequence of SEQ ID NO:33.

C22. The anti-TLR7 agent of any one of embodiments C2 to C20, wherein the CDRL1 comprises an amino acid sequence that is at least 90 percent identical to the amino acid sequence of SEQ ID NO:33.

C23. The anti-TLR7 agent of any one of embodiments C2 to C20, wherein the CDRL1 comprises an amino acid sequence that is at least 95 percent identical to the amino acid sequence of SEQ ID NO:33.

C24. The anti-TLR7 agent of any one of embodiments C2 to C20, wherein the CDRL1 comprises an amino acid sequence that is 100 percent identical to the amino acid sequence of SEQ ID NO:33.

C25. The anti-TLR7 agent of any one of embodiments C2 to C24, wherein the CDRL2 comprises an amino acid sequence that is at least 85 percent identical to the amino acid sequence of SEQ ID NO:34.

C26. The anti-TLR7 agent of any one of embodiments C2 to C24, wherein the CDRL2 comprises an amino acid sequence that is at least 90 percent identical to the amino acid sequence of SEQ ID NO:34.

C27. The anti-TLR7 agent of any one of embodiments C2 to C24, wherein the CDRL2 comprises an amino acid sequence that is at least 95 percent identical to the amino acid sequence of SEQ ID NO:34.

C28. The anti-TLR7 agent of any one of embodiments C2 to C24, wherein the CDRL2 comprises an amino acid sequence that is 100 percent identical to the amino acid sequence of SEQ ID NO:34.

C29. The anti-TLR7 agent of any one of embodiments C2 to C28, wherein the CDRL3 comprises an amino acid sequence that is at least 85 percent identical to the amino acid sequence of SEQ ID NO:35.

C30. The anti-TLR7 agent of any one of embodiments C2 to C28, wherein the CDRL3 comprises an amino acid sequence that is at least 90 percent identical to the amino acid sequence of SEQ ID NO:35.

C31. The anti-TLR7 agent of any one of embodiments C2 to C28, wherein the CDRL3 comprises an amino acid sequence that is at least 95 percent identical to the amino acid sequence of SEQ ID NO:35.

C32. The anti-TLR7 agent of any one of embodiments C2 to C28, wherein the CDRL3 comprises an amino acid sequence that is 100 percent identical to the amino acid sequence of SEQ ID NO:35.

C33. The anti-TLR7 agent of any one of embodiments C2 to C32, wherein the CDRH1 comprises an amino acid sequence chosen from DYWMS (SEQ ID NO: 1), NYYMA (SEQ ID NO: 2), DYYMA (SEQ ID NO: 3), DYCVH (SEQ ID NO: 4), and DYYIH (SEQ ID NO: 5).

C34. The anti-TLR7 agent of any one of embodiments C2 to C33, wherein the CDRH2 comprises an amino acid sequence chosen from DIKYDGSFIDYAPSLKN (SEQ ID NO: 6), DIKYDGTFIDYAPSLKN (SEQ ID NO: 7), SITNSGRTTYYRDSVKG (SEQ ID NO: 8), SISYEGSSTHYGDSVKA (SEQ ID NO: 9), YINPYSGYTNYNEKFKS (SEQ ID NO: 10), and FINPDSGYTNYNEKFKT (SEQ ID NO: 11).

C35. The anti-TLR7 agent of any one of embodiments C2 to C34, wherein the CDRH3 comprises an amino acid sequence chosen from DLTTVVDGFAY (SEQ ID NO:12), EGGDLYYSNYNYVRFAY (SEQ ID NO:13), HGGYPNWYFDF (SEQ ID NO:14), and GPYG-GYSGDGFDY (SEQ ID NO:15).

C36. The anti-TLR7 agent of any one of embodiments C2 to C35, wherein the CDRL1 comprises an amino acid sequence chosen RASEDIYNVLA (SEQ ID NO:16), RASEDIYNELA (SEQ ID NO:17), LPSEDIYNNLA (SEQ ID NO:18), and RASQSLSTSIH (SEQ ID NO:19).

C37. The anti-TLR7 agent of any one of embodiments C2 to C36, wherein the CDRL2 comprises an amino acid sequence chosen from NANRLHN (SEQ ID NO:20), NANNLHT (SEQ ID NO:21), NANSLHT (SEQ ID NO:22), YASNLQD (SEQ ID NO:23), and YASQPIS (SEQ ID NO:24).

C38. The anti-TLR7 agent of any one of embodiments C2 to C37, wherein the CDRL3 comprises an amino acid sequence chosen from QQYYDYPNT (SEQ ID NO:25), QQYYDYPHT (SEQ ID NO:26), QQYYDYPWT (SEQ ID NO:27), LQDSDYPFT (SEQ ID NO:28), and QQSYS-SPYT (SEQ ID NO:29).

C39. The anti-TLR7 agent of any one of embodiments C1 to C38, which comprises two immunoglobulin heavy chain variable domains and two immunoglobulin light chain variable domains.

C40. The anti-TLR7 agent of embodiment C39, wherein the two immunoglobulin heavy chain variable domains each comprise a set of CDRH1, CDRH2, and CDRH3 amino acid sequences.

C41. The anti-TLR7 agent of embodiment C39 or C40, wherein the two immunoglobulin light chain variable domains each comprise a set of CDRL1, CDRL2 and CDRL3 amino acid sequences.

C42. The anti-TLR7 agent of any one of embodiments C2 to C41, wherein each immunoglobulin heavy chain variable domain comprises a set of CDRH1, CDRH2, and CDRH3 amino acid sequences and each immunoglobulin light chain variable domain comprises a set of CDRL1, CDRL2 and CDRL3 amino acid sequences chosen from sets 1-6:

| set | CDRH1 (SEQ ID NO:) | CDRH2 (SEQ ID NO:) | CDRH3 (SEQ ID NO:) | CDRL1 (SEQ ID NO:) | CDRL2 (SEQ ID NO:) | CDRL3 (SEQ ID NO:) |
|---|---|---|---|---|---|---|
| 1 | DYWMS (1) | DIKYDGSFIDYA PSLKN (6) | DLTTVVDGFAY (12) | RASQSLSTSIH (19) | YASQPIS (24) | QQSYSSPYT (29) |
| 2 | DYWMS (1) | DIKYDGTFIDYA PSLKN (7) | DLTTVVDGFAY (12) | RASQSLSTSIH (19) | YASQPIS (24) | QQSYSSPYT (29) |
| 3 | NYYMA (2) | SITNSGRTTYY RDSVKG (8) | EGGDLYYSNYN YVRFAY (13) | LPSEDIYNNLA (18) | YASNLQD (23) | LQDSDYPFT (28) |
| 4 | DYYMA (3) | SISYEGSSTHY GDSVKA (9) | HGGYPNWYFD F (14) | RASEDIYNELA (17) | NANSLHT (22) | QQYYDYPWT (27) |
| 5 | DYCVH (4) | YINPYSGYTNY NEKFKS (10) | GPYGGYSGDG FDY (15) | RASEDIYNVLA (16) | NANRLHN (20) | QQYYDYPNT (25) |
| 6 | DYYIH (5) | FINPDSGYTNY NEKFKT (11) | GPYGGYSGDG FDY (15) | RASEDIYNVLA (16) | NANNLHT (21) | QQYYDYPHT (26) |

C43. The anti-TLR7 agent of embodiment C42, wherein all CDR sequences are from the same set.

C44. The anti-TLR7 agent of any one of embodiments C1 to C43, wherein TLR7 is detected at a significant level in plasmacytoid dendritic cells.

C45. The anti-TLR7 agent of embodiment C44, wherein TLR7 is detected in plasmacytoid dendritic cells using a flow cytometry assay.

C46. The anti-TLR7 agent of embodiment C44, wherein TLR7 is detected in plasmacytoid dendritic cells by intracellular staining.

C47. The anti-TLR7 agent of embodiment C46, wherein TLR7 is detected in plasmacytoid dendritic cells by intracellular staining with a signal to noise ratio of about 5 or greater.

C48. The anti-TLR7 agent of embodiment C46, wherein TLR7 is detected in plasmacytoid dendritic cells by intracellular staining with a signal to noise ratio of about 10 or greater.

C49. The anti-TLR7 agent of embodiment C46, wherein TLR7 is detected in plasmacytoid dendritic cells by intracellular staining with a signal to noise ratio of about 14 or greater.

C50. The anti-TLR7 agent of any one of embodiments C1 to C49, wherein TLR7 is detected at a significant level in B cells.

C50a. The anti-TLR7 agent of embodiment C50, wherein TLR7 is detected in B cells using a flow cytometry assay.

C51. The anti-TLR7 agent of embodiment C50, wherein TLR7 is detected in B cells by intracellular staining.

C52. The anti-TLR7 agent of embodiment C51, wherein TLR7 is detected in B cells by intracellular staining with a signal to noise ratio of about 2 or greater.

C53. The anti-TLR7 agent of embodiment C51, wherein TLR7 is detected in B cells by intracellular staining with a signal to noise ratio of about 3 or greater.

C54. The anti-TLR7 agent of embodiment C51, wherein TLR7 is detected in B cells by intracellular staining with a signal to noise ratio of about 4 or greater.

C54a. The anti-TLR7 agent of any one of embodiments C1 to C54, wherein TLR7 is detected at a significant level in monocytes.

C54b. The anti-TLR7 agent of embodiment C54a, wherein TLR7 is detected in monocytes using a flow cytometry assay.

C54c. The anti-TLR7 agent of embodiment C54a, wherein TLR7 is detected in monocytes by intracellular staining.

C54d. The anti-TLR7 agent of embodiment C54c, wherein TLR7 is detected in monocytes by intracellular staining with a signal to noise ratio of about 2 or greater.

C54e. The anti-TLR7 agent of embodiment C54c, wherein TLR7 is detected in monocytes by intracellular staining with a signal to noise ratio of about 3 or greater.

C54f. The anti-TLR7 agent of embodiment C54c, wherein TLR7 is detected in monocytes by intracellular staining with a signal to noise ratio of about 4 or greater.

C55. The anti-TLR7 agent of any one of embodiments C1 to C54f, wherein TLR7 is not significantly detected in other immune cells in the population, wherein the other immune cells comprise one or more of CD3⁻CD19⁻ lymphocytes and CD3⁺CD19⁻ T cells.

C56. The anti-TLR7 agent of any one of embodiments C1 to C55, wherein the agent is isolated.

C57. The anti-TLR7 agent of any one of embodiments C1 to C56, wherein the agent is non-naturally occurring.

C58. The anti-TLR7 agent of any one of embodiments C1 to C57, wherein the agent is an antibody, or antigen-binding fragment thereof.

C59. The anti-TLR7 agent of any one of embodiments C1 to C57, wherein the agent is an antibody, or derivative thereof.

C60. The anti-TLR7 agent of any one of embodiments C1 to C59, wherein the agent is a humanized antibody, or an antigen binding fragment thereof.

C61. The anti-TLR7 agent of any one of embodiments C1 to C59, wherein the agent is a derivative of a humanized antibody that binds TLR7.

C62. The anti-TLR7 agent of any one of embodiments C1 to C61, wherein the agent is comprises a detectable marker or label.

C63. The anti-TLR7 agent of any one of embodiments C1 to C62, wherein the agent is conjugated to a detectable marker or label.

C64. The anti-TLR7 agent of any one of embodiments C1 to C63, wherein the agent is non-diffusively immobilized on a solid support.

C65. A diagnostic reagent comprising the anti-TLR7 agent of any one of embodiments C1 to C64.

C66. A kit comprising the anti-TLR7 agent of any one of embodiments C1 to C64 or the diagnostic reagent of embodiment C65.

C67. A diagnostic kit configured to detect Toll-like Receptor 7 (TLR7) in a biological sample, wherein the kit comprises the anti-TLR7 agent of any one of embodiments C1 to C64 or the diagnostic reagent of embodiment C65.

C68. An isolated nucleic acid molecule comprising a nucleotide sequence that encodes an immunoglobulin heavy chain variable domain of the anti-TLR7 agent of any one of embodiments C1 to C64.

C69. An isolated nucleic acid molecule comprising a nucleotide sequence that encodes an immunoglobulin light chain variable domain of the anti-TLR7 agent of any one of embodiments C1 to C64.

C70. A recombinant expression vector comprising a first expression cassette and a second expression cassette, wherein the first expression cassette comprises a promoter and a nucleic acid molecule comprising a nucleotide sequence that encodes an immunoglobulin heavy chain variable domain of the anti-TLR7 agent of any one of embodiments C1 to C64, and the second expression cassette comprises a promoter and a nucleic acid molecule comprising a nucleotide sequence that encodes an immunoglobulin light chain variable domain of the anti-TLR7 agent of any one of embodiments C1 to C64.

C71. A recombinant host cell transfected with the recombinant expression vector of embodiment C70.

C72. A method of detecting TLR7, comprising contacting a sample known or suspected to contain TLR7 with the anti-TLR7 agent of any one of embodiments C1 to C64, and, if the sample contains TLR7, detecting TLR7: anti-TLR7 complexes.

C73. A method of detecting TLR7 in a heterogeneous population of immune cells, comprising contacting the population with an anti-TLR7 agent of any one of embodiments C1 to C64, and, if the population contains cells expressing TLR7, detecting TLR7: anti-TLR7 complexes.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

Modifications may be made to the foregoing without departing from the basic aspects of the technology. Although the technology has been described in substantial detail with reference to one or more specific embodiments, those of ordinary skill in the art will recognize that changes may be made to embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude nay equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2, and 3" refers to about 1, about 2, and about 3). For example, a weight of "about 100 grams" can include weights between 90 grams and 110 grams. Further, when a listing of values is described herein (e.g., about 50%, 60%, 70%, 80%, 85%, or 86%) the listing included all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

---

What is claimed is:

1. An anti-TLR7 agent that binds Toll-like Receptor 7 (TLR7), comprising an immunoglobulin heavy chain variable domain and an immunoglobulin light chain variable domain, wherein the immunoglobulin heavy chain variable domain comprises a set of CDRH1, CDRH2, and CDRH3 amino acid sequences and the immunoglobulin light chain variable domain comprises a set of CDRL1, CDRL2, and CDRL3 amino acid sequences, wherein the amino acid sequences for the immunoglobulin heavy chain variable domain and the immunoglobulin light chain variable domain comprise sequences selected from one of sets 1-6:

| set | CDRH1 (SEQ ID NO:) | CDRH2 (SEQ ID NO:) | CDRH3 (SEQ ID NO:) | CDRL1 (SEQ ID NO:) | CDRL2 (SEQ ID NO:) | CDRL3 (SEQ ID NO:) |
|---|---|---|---|---|---|---|
| 1 | DYWMS (1) | DIKYDGSFID YAPSLKN (6) | DLTTVVDGFAY (12) | RASQSLSTSI H (19) | YASQPIS (24) | QQSYSSPYT (29) |
| 2 | DYWMS (1) | DIKYDGTFI DYAPSLKN (7) | DLTTVVDGFAY (12) | RASQSLSTSI H (19) | YASQPIS (24) | QQSYSSPYT (29) |
| 3 | NYYMA (2) | SITNSGRTTY YRDSVKG (8) | EGGDLYYSN YNYVRFAY (13) | LPSEDIYNN LA (18) | YASNLQD (23) | LQDSDYPFT (28) |

-continued

| set | CDRH1 (SEQ ID NO:) | CDRH2 (SEQ ID NO:) | CDRH3 (SEQ ID NO:) | CDRL1 (SEQ ID NO:) | CDRL2 (SEQ ID NO:) | CDRL3 (SEQ ID NO:) |
|---|---|---|---|---|---|---|
| 4 | DYYMA (3) | SISYEGSSTH YGDSVKA (9) | HGGYPNWYFDF (14) | RASEDIYNE LA (17) | NANSLHT (22) | QQYYDYPW T (27) |
| 5 | DYCVH (4) | YINPYSGYT NYNEKFKS (10) | GPYGGYSGDGFDY (15) | RASEDIYNV LA (16) | NANRLHN (20) | QQYYDYPN T (25) |
| 6 | DYYIH (5) | FINPDSGYT NYNEKFKT | GPYGGYSGDGFDY (15) | RASEDIYNV LA (16) | NANNLHT (21) | QQYYDYPH T (26) | and wherein all CDR amino acid sequences are from the same set.

2. The anti-TLR7 agent of claim 1, wherein the amino acid sequences for the immunoglobulin heavy chain variable domain and the immunoglobulin light chain variable domain are selected from set 1.

3. The anti-TLR7 agent of claim 1, wherein the amino acid sequences for the immunoglobulin heavy chain variable domain and the immunoglobulin light chain variable domain are selected from set 2.

4. The anti-TLR7 agent of claim 1, wherein the amino acid sequences for the immunoglobulin heavy chain variable domain and the immunoglobulin light chain variable domain are selected from set 3.

5. The anti-TLR7 agent of claim 1, wherein the immunoglobulin heavy chain variable domain (VH) comprises at least 90% identity to the sequence set forth in any one of SEQ ID NOS: 36-41.

6. The anti-TLR7 agent of claim 1, wherein the immunoglobulin heavy chain variable domain (VH) comprises at least 90% identity to the sequence set forth in SEQ ID NO:41.

7. The anti-TLR7 agent of claim 1, wherein the immunoglobulin light chain variable region comprises at least 90% identity to a sequence set forth in any of SEQ ID NOS: 42-47.

8. The anti-TLR7 agent of claim 1, wherein the immunoglobulin light chain variable region comprises at least 90% identity to a sequence set forth in SEQ ID NO:47.

9. The anti-TLR7 agent of claim 1, comprising two immunoglobulin heavy chain variable domains and two immunoglobulin light chain variable domains.

10. The anti-TLR7 agent of claim 1, wherein the agent comprises an antibody, or antigen-binding fragment thereof.

11. The anti-TLR7 agent of claim 1, wherein the agent comprises a humanized antibody, or a humanized antigen binding fragment thereof.

12. The anti-TLR7 agent of claim 1, further comprising one or more human framework regions.

13. The anti-TLR7 agent of claim 1, wherein the agent is conjugated to a detectable marker or label.

14. The anti-TLR7 agent of claim 1, wherein the agent is non-diffusively immobilized on a solid support.

15. A diagnostic reagent comprising the anti-TLR7 agent of claim 1.

16. A kit comprising the anti-TLR7 agent of claim 1.

17. The anti-TLR7 agent of claim 1, wherein the amino acid sequences for the immunoglobulin heavy chain variable domain and the immunoglobulin light chain variable domain are selected from set 4.

18. The anti-TLR7 agent of claim 1, wherein the amino acid sequences for the immunoglobulin heavy chain variable domain and the immunoglobulin light chain variable domain are selected from set 5.

19. The anti-TLR7 agent of claim 1, wherein the amino acid sequences for the immunoglobulin heavy chain variable domain and the immunoglobulin light chain variable domain are selected from set 6.

* * * * *